United States Patent [19]
Takashima et al.

[11] Patent Number: 6,037,335
[45] Date of Patent: *Mar. 14, 2000

[54] PHOSPHONATE-NUCLEOTIDE ESTER DERIVATIVES

[75] Inventors: Hideaki Takashima; Naoko Inoue; Masaru Ubasawa; Kouichi Sekiya; Shingo Yabuuchi, all of Kanagawa-ken, Japan

[73] Assignee: Mitsubishi Chemical Corporation, Tokyo, Japan

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/942,490

[22] Filed: Oct. 2, 1997

Related U.S. Application Data

[63] Continuation of application No. 08/779,623, Jan. 7, 1997, abandoned, which is a continuation of application No. 08/266,637, Jun. 28, 1994, abandoned.

[30] Foreign Application Priority Data

Jun. 29, 1993 [JP] Japan ..................... 5-159693

[51] Int. Cl.[7] ..................... A61K 31/675; C07F 9/6512
[52] U.S. Cl. ..................... 514/80; 514/81; 544/244
[58] Field of Search ..................... 544/244; 514/81, 514/80

[56] References Cited

U.S. PATENT DOCUMENTS 5,663,159  9/1997  Starrett, Jr. et al. ............ 514/81
5,840,716  11/1998  Ubasawa et al. .............. 514/75

FOREIGN PATENT DOCUMENTS 0 481 214  4/1992  European Pat. Off. .
WO92/09611  6/1992  WIPO .

OTHER PUBLICATIONS

*Drug Evaluations* by American Medical Association p 1861–1862 (1993).

*Primary Examiner*—Emily Bernhardt
*Attorney, Agent, or Firm*—Wenderoth, Lind & Ponack, L.L.P.

[57] ABSTRACT

Phosphonate-nucleotide ester compounds of the formula (I) have excellent antiviral activity and antineoplastic activity. Further, they can be orally administered.

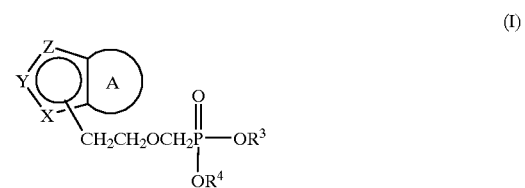

wherein ring A represents

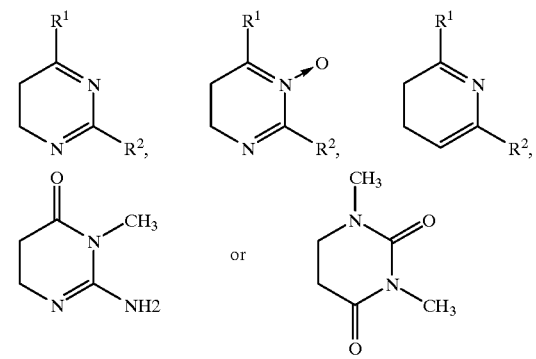

wherein $R^1$ and $R^2$ independently represent hydrogen, halogen, hydroxyl, mercapto, $C_6$–$C_{10}$ arylthio or amino; $R^3$ represents $C_1$–$C_4$ alkyl or ethyl having one or more substituents selected from the group consisting of fluorine, $C_1$–$C_4$ alkoxy, phenoxy, $C_7$–$C_{10}$ phenylalkoxy and $C_2$–$C_5$ acyloxy; $R^4$ represents ethyl having one or more substituents selected from the group consisting of fluorine, $C_1$–$C_4$ alkoxy, phenoxy, $C_7$–$C_{10}$ phenylalkoxy and $C_2$–$C_5$ acyloxy; X, Y and Z independently represent methyne or nitrogen atom; or a pharmaceutically acceptable salt thereof.

7 Claims, No Drawings

PHOSPHONATE-NUCLEOTIDE ESTER DERIVATIVES

This application is continuation of now abandoned application Ser. No 08/779,623, filed Jan. 7, 1997, which application is a continuation of now abandoned application, Ser. No. 08/266,637, filed Jun. 28, 1994.

BACKGROUND OF THE INVENTION

1. Field of the Invention

This invention relates to novel phosphonate-nucleotide ester derivatives or pharmaceutically acceptable salts thereof. More particularly, it relates to novel phosphonate-nucleotide ester derivatives or pharmaceutically acceptable salts thereof which can be orally administered as antiviral agents.

2. Background of the Invention

Infectious viral diseases have been recognized as medically important problems. For treatment of such diseases, drugs having antiviral activity but no inhibitory activity on growth of normal cell lines have been developed. For example, 9-(2-phosphonylmethoxy)ethyladenine (PMEA), 9-(2-phosphonylmethoxy)ethyl-2,6-diaminopurine (PMDAP) etc. have been reported to be effective on herpes simplex viruses type-I and II (HSV-1 and HSV-2), human immunodeficiency virus (HIV), hepatitis B virus (Yokota et al., Antimicrob. Agents Chemother., 35, 394 (1991); Votruba et al., Mol. Pharmacol., 32, 524 (1987)].

The problems of these nucleotides and ionic organophosphate esters are their deficiency of oral absorptivity [see, De Clercq et al., Antimicrob. Agents Chemother., 33, 185 (1989)]. Therefore, these compounds should be parenterally administered, for example, by intravenous or intramuscular injection, to attain sufficient blood concentration to elicit their effect.

However, it is difficult to apply treatment utilizing parenteral administration unless the subject is in a hospital. Accordingly, it is not a preferred method to treat subjects suffering from altricious diseases such as AIDS and HBV diseases. Accordingly, there required development of drugs which have antiviral activity and can be parenterally administered. Up to date, no drugs have been put into practical use.

SUMMARY OF THE INVENTION

The present inventors have studied intensively to solve the above problems. As the results, we have found that the object can be attained using a certain kind of phosphonate-nucleotide esters, and have attained the present invention.

That is, the point of the present invention resides in phosphonatenucleotide ester derivatives of the following general formula (I):

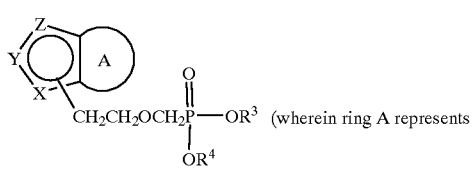 (I)

(wherein ring A represents

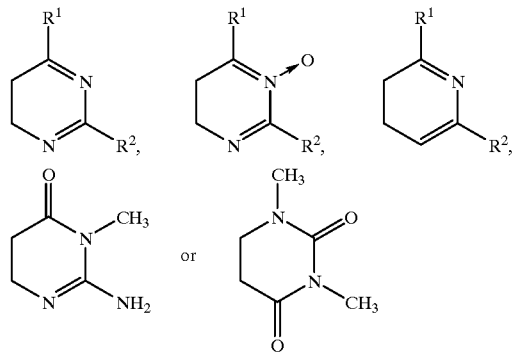

(wherein $R^1$ and $R^2$ independently represent hydrogen, halogen, hydroxyl, mercapto, $C_6$–$C_{10}$ arylthio or amino), $R^3$ represents $C_1$–$C_4$ alkyl or ethyl having one or more substituents selected from the group consisting of fluorine, $C_1$–$C_4$ alkoxy, phenoxy, $C_7$–$C_{10}$ phenylalkoxy and $C_2$–$C_5$ acyloxy; $R^4$ represents ethyl having one or more substituents selected from the group consisting of fluorine, $C_1$–$C_4$ alkoxy, phenoxy, $C_7$–$C_{10}$ phenylalkoxy and $C_2$–$C_5$ acyloxy; X, Y and Z independently represent methyne or nitrogen atom); or pharmaceutically acceptable salts thereof.

DETAILED DESCRIPTION OF THE INVENTION

The present invention will be explained in detail.

Phosphonate-nucleotide ester derivatives of the present invention are represented by the above general formula (I). In the above general formula (I), halogen atoms in $R^1$ and $R^2$ include, for example, fluorine, chlorine, bromine, inodine; $C_6$–$C_{10}$ arylthio includes, for example, phenylthio, tolylthio, naphthylthio. $C_1$–$C_4$ alkyl in $R^3$ includes, for example, methyl, ethyl, n-propyl, i-propyl, n-butyl, i-butyl, sec-butyl, tert-butyl. $C_1$–$C_4$ alkoxy as a substituent on ethyl in $R^3$ includes, for example, methoxy, ethoxy, n-propoxy, i-propoxy, butoxy. $C_7$–$C_{10}$ phenylalkoxy includes, for example, phenyl-$C_1$–$C_4$ alkoxy such as benzyloxy, phenethyloxy, phenylpropoxy. $C_2$–$C_5$ acyloxy includes, for example, acetoxy, propionyloxy, butyryloxy, i-butyryloxy, valeryloxy. $C_1$–$C_4$ alkoxy, $C_7$–$C_{10}$ phenylalkoxy and $C_2$–$C_5$ acyloxy as substituents on ethyl in $R^4$ include those on ethyl in $R^3$.

A preferred ring A in the above general formula (I) includes:

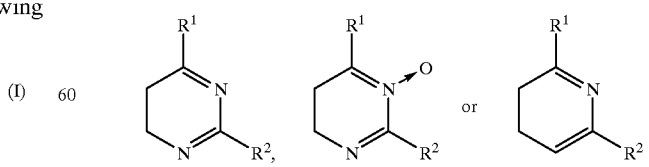

(wherein $R^1$ and $R^2$ independently represent hydrogen, halogen, hydroxyl, mercapto, $C_6$–$C_{10}$ arylthio or amino).

A particularly preferred A is

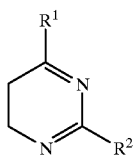

(wherein $R^1$ represents hydrogen, chlorine, hydroxyl, mercapto, tolylthio or amino; $R^2$ represents hydrogen, chlorine, iodine, hydroxyl or amino);

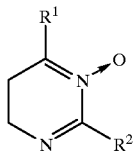

(wherein $R^1$ represents amino; $R^2$ represents hydrogen); or

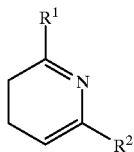

(wherein $R^1$ and $R^2$ represent amino).

$R^3$ is preferably $C_1$–$C_3$ alkyl, 2,2,2-trifluoroethyl or an ethyl group having a substituent selected from a group consisting of $C_1$–$C_3$ alkoxy, phenoxy, $C_7$–$C_{10}$ phenylalkoxy and $C_2$–$C_5$ acyloxy. Particularly, $C_1$–$C_3$ alkyl or 2,2,2-trifluoroethyl is preferred.

$R^4$ is preferably 2,2,2-trifluoroethyl or an ethyl group having a substituent selected from a group consisting of $C_1$–$C_3$ alkoxy, phenoxy, $C_7$–$C_{10}$ phenylalkoxy and $C_2$–$C_5$ acyloxy. Particularly, 2,2,2-trifluoroethyl is preferred. When $R^3$ or $R^4$ represents a substituted ethyl group, such an ethyl group is preferably substituted at 2-position. Further, at least one of $R^3$ and $R^4$ is preferably 2,2,2-trifluoroethyl. X and Z are preferably nitrogen atoms.

Phosphonate-nucleotide ester derivatives of the present invention represented by the above general formula (I) can form pharmaceutically acceptable salts thereof. Examples of such salt include, for example, in the presence of acidic groups, metal salt such as lithium, sodium, potassium, magnesium, calcium salt, ammonium salt such as methylammonium, dimethylammonium, trimethylammonium, dicyclohexylammonium; in the presence of basic groups, mineral salts such as hydrochloride, hydrobromide, sulfate, nitrate, phosphate, organic salts such as methanesulfonate, benzenesulfonate, paratoluenesulfonate, acetate, propionate, tartrate, fumarate, maleate, malate, oxalate, succinate, citrate, benzoate, mandelate, cinnamate, lactate.

Compounds of the present invention may form tautomers such as keto-enol tautomers depending on the substituents. Such tautomers are also included in the present invention.

Examples of the present compounds are shown in the following tables 1 to 7 (in the tables, P.S. indicates the position of the substituent:

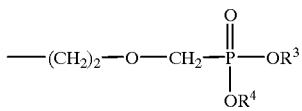

as X, Y or Z; and C for X, Y or Z represents —CH=).

TABLE 1

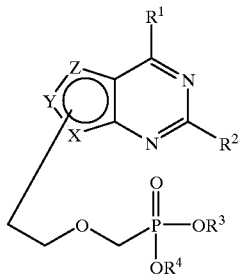

| Comp. No. | $R^1$ | $R^2$ | $R^3$ | $R^4$ | X | Y | Z | P.S. |
|---|---|---|---|---|---|---|---|---|
| 1 | —H | —H | —CH₃ | —CF₂CF₃ | N | C | N | X |
| 2 | —H | —H | —CH₃ | —CF₂CF₃ | N | C | N | Z |
| 3 | —H | —H | —CH₃ | —CH₂CF₃ | N | C | N | X |
| 4 | —H | —H | —CH₃ | —CH₂CF₃ | N | C | N | Z |
| 5 | —H | —H | —CF₂CF₃ | —CF₂CF₃ | N | C | N | X |
| 6 | —H | —H | —CF₂CF₃ | —CF₂CF₃ | N | C | N | Z |
| 7 | —H | —H | —CF₂CF₃ | —CH₂CF₃ | N | C | N | X |
| 8 | —H | —H | —CF₂CF₃ | —CH₂CF₃ | N | C | N | Z |
| 9 | —H | —H | —CH₂CF₃ | —CH₂CF₃ | N | C | N | X |
| 10 | —H | —H | —CH₂CF₃ | —CH₂CF₃ | N | C | N | Z |
| 11 | —H | —H | —CH₂CH₂OCH₃ | —CH₂CF₃ | N | C | N | X |
| 12 | —H | —H | —CH₂CH₂OCH₃ | —CH₂CF₃ | N | C | N | Z |
| 13 | —H | —H | —CH₂CH₂OCH₃ | —CH₂CH₂OCH₃ | N | C | N | X |
| 14 | —H | —H | —CH₂CH₂OCH₃ | —CH₂CH₂OCH₃ | N | C | N | Z |
| 15 | —H | —H | —CH₂CH₂OC₂H₅ | —CH₂CH₂OC₂H₅ | N | C | N | X |
| 16 | —H | —H | —CH₂CH₂OC₂H₅ | —CH₂CH₂OC₂H₅ | N | C | N | Z |

TABLE 1-continued

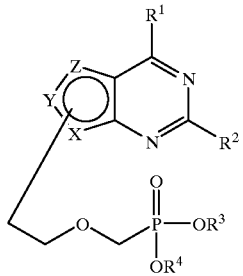

| Comp. No. | R$^1$ | R$^2$ | R$^3$ | R$^4$ | X | Y | Z | P.S. |
|---|---|---|---|---|---|---|---|---|
| 17 | —H | —H | —CH$_2$CH$_2$OC$_3$H$_7$ | —CH$_2$CH$_2$OC$_3$H$_7$ | N | C | N | X |
| 18 | —H | —H | —CH$_2$CH$_2$OC$_3$H$_7$ | —CH$_2$CH$_2$OC$_3$H$_7$ | N | C | N | Z |
| 19 | —H | —H | —CH$_2$CH$_2$OC$_6$H$_5$ | —CH$_2$CF$_3$ | N | C | N | X |
| 20 | —H | —H | —CH$_2$CH$_2$OC$_6$H$_5$ | —CH$_2$CF$_3$ | N | C | N | Z |
| 21 | —H | —H | —CH$_2$CH$_2$OC$_6$H$_5$ | —CH$_2$CH$_2$OCH$_3$ | N | C | N | X |
| 22 | —H | —H | —CH$_2$CH$_2$OC$_6$H$_5$ | —CH$_2$CH$_2$OCH$_3$ | N | C | N | Z |
| 23 | —H | —H | —CH$_2$CH$_2$OC$_6$H$_5$ | —CH$_2$CH$_2$OC$_6$H$_5$ | N | C | N | X |
| 24 | —H | —H | —CH$_2$CH$_2$OC$_6$H$_5$ | —CH$_2$CH$_2$OC$_6$H$_5$ | N | C | N | Z |
| 25 | —H | —H | —CH$_2$CH$_2$OCH$_2$C$_6$H$_5$ | —CH$_2$CF$_3$ | N | C | N | X |
| 26 | —H | —H | —CH$_2$CH$_2$OCH$_2$C$_6$H$_5$ | —CH$_2$CF$_3$ | N | C | N | Z |
| 27 | —H | —H | —CH$_2$CH$_2$OCH$_2$C$_6$H$_5$ | —CH$_2$CH$_2$OCH$_3$ | N | C | N | X |
| 28 | —H | —H | —CH$_2$CH$_2$OCH$_2$C$_6$H$_5$ | —CH$_2$CH$_2$OCH$_3$ | N | C | N | Z |
| 29 | —H | —H | —CH$_2$CH$_2$OCH$_2$C$_6$H$_5$ | —CH$_2$CH$_2$OC$_6$H$_5$ | N | C | N | X |
| 30 | —H | —H | —CH$_2$CH$_2$OCH$_2$C$_6$H$_5$ | —CH$_2$CH$_2$OC$_6$H$_5$ | N | C | N | Z |
| 31 | —H | —H | —CH$_2$CH$_2$OCH$_2$C$_6$H$_5$ | —CH$_2$CH$_2$OCH$_2$C$_6$H$_5$ | N | C | N | X |
| 32 | —H | —H | —CH$_2$CH$_2$OCH$_2$C$_6$H$_5$ | —CH$_2$CH$_2$OCH$_2$C$_6$H$_5$ | N | C | N | Z |
| 33 | —H | —H | —CH$_2$CH$_2$OC$_2$H$_4$C$_6$H$_5$ | —CH$_2$CH$_2$OC$_2$H$_4$C$_6$H$_5$ | N | C | N | X |
| 34 | —H | —H | —CH$_2$CH$_2$OC$_2$H$_4$C$_6$H$_5$ | —CH$_2$CH$_2$OC$_2$H$_4$C$_6$H$_5$ | N | C | N | Z |
| 35 | —H | —H | —CH$_2$CH$_2$OC(O)CH$_3$ | —CH$_2$CF$_3$ | N | C | N | X |
| 36 | —H | —H | —CH$_2$CH$_2$OC(O)CH$_3$ | —CH$_2$CF$_3$ | N | C | N | Z |
| 37 | —H | —H | —CH$_2$CH$_2$OC(O)CH$_3$ | —CH$_2$CH$_2$OCH$_3$ | N | C | N | X |
| 38 | —H | —H | —CH$_2$CH$_2$OC(O)CH$_3$ | —CH$_2$CH$_2$OCH$_3$ | N | C | N | Z |
| 39 | —H | —H | —CH$_2$CH$_2$OC(O)CH$_3$ | —CH$_2$CH$_2$OC$_6$H$_5$ | N | C | N | X |
| 40 | —H | —H | —CH$_2$CH$_2$OC(O)CH$_3$ | —CH$_2$CH$_2$OC$_6$H$_5$ | N | C | N | Z |
| 41 | —H | —H | —CH$_2$CH$_2$OC(O)CH$_3$ | —CH$_2$CH$_2$OCH$_2$C$_6$H$_5$ | N | C | N | X |
| 42 | —H | —H | —CH$_2$CH$_2$OC(O)CH$_3$ | —CH$_2$CH$_2$OCH$_2$C$_6$H$_5$ | N | C | N | Z |
| 43 | —H | —H | —CH$_2$CH$_2$OC(O)CH$_3$ | —CH$_2$CH$_2$OC(O)CH$_3$ | N | C | N | X |
| 44 | —H | —H | —CH$_2$CH$_2$OC(O)CH$_3$ | —CH$_2$CH$_2$OC(O)CH$_3$ | N | C | N | Z |
| 45 | —H | —H | —CH$_2$CH$_2$OC(O)C$_2$H$_5$ | —CH$_2$CH$_2$OC(O)C$_2$H$_5$ | N | C | N | X |
| 46 | —H | —H | —CH$_2$CH$_2$OC(O)C$_2$H$_5$ | —CH$_2$CH$_2$OC(O)C$_2$H$_5$ | N | C | N | Z |
| 47 | —H | —H | —CH$_2$CH$_2$OC(O)C$_3$H$_7$ | —CH$_2$CH$_2$OC(O)C$_3$H$_7$ | N | C | N | X |
| 48 | —H | —H | —CH$_2$CH$_2$OC(O)C$_3$H$_7$ | —CH$_2$CH$_2$OC(O)C$_3$H$_7$ | N | C | N | Z |
| 49 | —H | —H | —CH$_2$CH$_2$OC(O)C$_4$H$_9$ | —CH$_2$CH$_2$OC(O)C$_4$H$_9$ | N | C | N | X |
| 50 | —H | —H | —CH$_2$CH$_2$OC(O)C$_4$H$_9$ | —CH$_2$CH$_2$OC(O)C$_4$H$_9$ | N | C | N | Z |
| 51 | —H | —OH | —CH$_3$ | —CF$_2$CF$_3$ | N | C | N | X |
| 52 | —H | —OH | —CH$_3$ | —CF$_2$CF$_3$ | N | C | N | Z |
| 53 | —H | —OH | —CH$_3$ | —CH$_2$CF$_3$ | N | C | N | X |
| 54 | —H | —OH | —CH$_3$ | —CH$_2$CF$_3$ | N | C | N | Z |
| 55 | —H | —OH | —CF$_2$CF$_3$ | —CF$_2$CF$_3$ | N | C | N | X |
| 56 | —H | —OH | —CF$_2$CF$_3$ | —CF$_2$CF$_3$ | N | C | N | Z |
| 57 | —H | —OH | —CF$_2$CF$_3$ | —CH$_2$CF$_3$ | N | C | N | X |
| 58 | —H | —OH | —CF$_2$CF$_3$ | —CH$_2$CF$_3$ | N | C | N | Z |
| 59 | —H | —OH | —CH$_2$CF$_3$ | —CH$_2$CF$_3$ | N | C | N | X |
| 60 | —H | —OH | —CH$_2$CF$_3$ | —CH$_2$CF$_3$ | N | C | N | Z |
| 61 | —H | —OH | —CH$_2$CH$_2$OCH$_3$ | —CH$_2$CF$_3$ | N | C | N | X |
| 62 | —H | —OH | —CH$_2$CH$_2$OCH$_3$ | —CH$_2$CF$_3$ | N | C | N | Z |
| 63 | —H | —OH | —CH$_2$CH$_2$OCH$_3$ | —CH$_2$CH$_2$OCH$_3$ | N | C | N | X |
| 64 | —H | —OH | —CH$_2$CH$_2$OCH$_3$ | —CH$_2$CH$_2$OCH$_3$ | N | C | N | Z |
| 65 | —H | —OH | —CH$_2$CH$_2$OC$_2$H$_5$ | —CH$_2$CH$_2$OC$_2$H$_5$ | N | C | N | X |
| 66 | —H | —OH | —CH$_2$CH$_2$OC$_2$H$_5$ | —CH$_2$CH$_2$OC$_2$H$_5$ | N | C | N | Z |
| 67 | —H | —OH | —CH$_2$CH$_2$OC$_3$H$_7$ | —CH$_2$CH$_2$OC$_3$H$_7$ | N | C | N | X |
| 68 | —H | —OH | —CH$_2$CH$_2$OC$_3$H$_7$ | —CH$_2$CH$_2$OC$_3$H$_7$ | N | C | N | Z |
| 69 | —H | —OH | —CH$_2$CH$_2$OC$_6$H$_5$ | —CH$_2$CF$_3$ | N | C | N | X |
| 70 | —H | —OH | —CH$_2$CH$_2$OC$_6$H$_5$ | —CH$_2$CF$_3$ | N | C | N | Z |
| 71 | —H | —OH | —CH$_2$CH$_2$OC$_6$H$_5$ | —CH$_2$CH$_2$OCH$_3$ | N | C | N | X |
| 72 | —H | —OH | —CH$_2$CH$_2$OC$_6$H$_5$ | —CH$_2$CH$_2$OCH$_3$ | N | C | N | Z |
| 73 | —H | —OH | —CH$_2$CH$_2$OC$_6$H$_5$ | —CH$_2$CH$_2$OC$_6$H$_5$ | N | C | N | X |
| 74 | —H | —OH | —CH$_2$CH$_2$OC$_6$H$_5$ | —CH$_2$CH$_2$OC$_6$H$_5$ | N | C | N | Z |
| 75 | —H | —OH | —CH$_2$CH$_2$OCH$_2$C$_6$H$_5$ | —CH$_2$CF$_3$ | N | C | N | X |
| 76 | —H | —OH | —CH$_2$CH$_2$OCH$_2$C$_6$H$_5$ | —CH$_2$CF$_3$ | N | C | N | Z |
| 77 | —H | —OH | —CH$_2$CH$_2$OCH$_2$C$_6$H$_5$ | —CH$_2$CH$_2$OCH$_3$ | N | C | N | X |

TABLE 1-continued

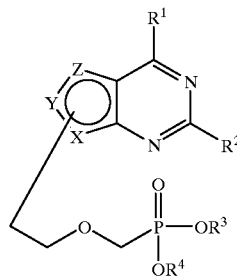

| Comp. No. | R¹ | R² | R³ | R⁴ | X | Y | Z | P.S. |
|---|---|---|---|---|---|---|---|---|
| 78 | —H | —OH | —CH₂CH₂OCH₂C₆H₅ | —CH₂CH₂OCH₃ | N | C | N | Z |
| 79 | —H | —OH | —CH₂CH₂OCH₂C₆H₅ | —CH₂CH₂OC₆H₅ | N | C | N | X |
| 80 | —H | —OH | —CH₂CH₂OCH₂C₆H₅ | —CH₂CH₂OC₆H₅ | N | C | N | Z |
| 81 | —H | —OH | —CH₂CH₂OCH₂C₆H₅ | —CH₂CH₂OCH₂C₆H₅ | N | C | N | X |
| 82 | —H | —OH | —CH₂CH₂OCH₂C₆H₅ | —CH₂CH₂OCH₂C₆H₅ | N | C | N | Z |
| 83 | —H | —OH | —CH₂CH₂OC₂H₄C₆H₅ | —CH₂CH₂OC₂H₄C₆H₅ | N | C | N | X |
| 84 | —H | —OH | —CH₂CH₂OC₂H₄C₆H₅ | —CH₂CH₂OC₂H₄C₆H₅ | N | C | N | Z |
| 85 | —H | —OH | —CH₂CH₂OC(O)CH₃ | —CH₂CF₃ | N | C | N | X |
| 86 | —H | —OH | —CH₂CH₂OC(O)CH₃ | —CH₂CF₃ | N | C | N | Z |
| 87 | —H | —OH | —CH₂CH₂OC(O)CH₃ | —CH₂CH₂OCH₃ | N | C | N | X |
| 88 | —H | —OH | —CH₂CH₂OC(O)CH₃ | —CH₂CH₂OCH₃ | N | C | N | Z |
| 89 | —H | —OH | —CH₂CH₂OC(O)CH₃ | —CH₂CH₂OC₆H₅ | N | C | N | X |
| 90 | —H | —OH | —CH₂CH₂OC(O)CH₃ | —CH₂CH₂OC₆H₅ | N | C | N | Z |
| 91 | —H | —OH | —CH₂CH₂OC(O)CH₃ | —CH₂CH₂OCH₂C₆H₅ | N | C | N | X |
| 92 | —H | —OH | —CH₂CH₂OC(O)CH₃ | —CH₂CH₂OCH₂C₆H₅ | N | C | N | Z |
| 93 | —H | —OH | —CH₂CH₂OC(O)CH₃ | —CH₂CH₂OC(O)CH₃ | N | C | N | X |
| 94 | —H | —OH | —CH₂CH₂OC(O)CH₃ | —CH₂CH₂OC(O)CH₃ | N | C | N | Z |
| 95 | —H | —OH | —CH₂CH₂OC(O)C₂H₅ | —CH₂CH₂OC(O)C₂H₅ | N | C | N | X |
| 96 | —H | —OH | —CH₂CH₂OC(O)C₂H₅ | —CH₂CH₂OC(O)C₂H₅ | N | C | N | Z |
| 97 | —H | —OH | —CH₂CH₂OC(O)C₃H₇ | —CH₂CH₂OC(O)C₃H₇ | N | C | N | X |
| 98 | —H | —OH | —CH₂CH₂OC(O)C₃H₇ | —CH₂CH₂OC(O)C₃H₇ | N | C | N | Z |
| 99 | —H | —OH | —CH₂CH₂OC(O)C₄H₆ | —CH₂CH₂OC(O)C₄H₉ | N | C | N | X |
| 100 | —H | —OH | —CH₂CH₂OC(O)C₄H₉ | —CH₂CH₂OC(O)C₄H₉ | N | C | N | Z |
| 101 | —H | —NH₂ | —CH₃ | —CF₂CF₃ | N | C | N | X |
| 102 | —H | —NH₂ | —CH₃ | —CF₂CF₃ | N | C | N | Z |
| 103 | —H | —NH₂ | —CH₃ | —CH₂CF₃ | N | C | N | X |
| 104 | —H | —NH₂ | —CH₃ | —CH₂CF₃ | N | C | N | Z |
| 105 | —H | —NH₂ | —CF₂CF₃ | —CF₂CF₃ | N | C | N | X |
| 106 | —H | —NH₂ | —CF₂CF₃ | —CF₂CF₃ | N | C | N | Z |
| 107 | —H | —NH₂ | —CF₂Cf3 | —CH₂CF₃ | N | C | N | X |
| 108 | —H | —NH₂ | —CF₂CF₃ | —CH₂CF₃ | N | C | N | Z |
| 109 | —H | —NH₂ | —CH₂CF₃ | —CH₂CF₃ | N | C | N | X |
| 110 | —H | —NH₂ | —CH₂CF₃ | —CH₂CF₃ | N | C | N | Z |
| 111 | —H | —NH₂ | —CH₂CH₂OCH₃ | —CH₂CF₃ | N | C | N | X |
| 112 | —H | —NH₂ | —CH₂CH₂OCH₃ | —CH₂CF₃ | N | C | N | Z |
| 113 | —H | —NH₂ | —CH₂CH₂OCH₃ | —CH₂CH₂OCH₃ | N | C | N | X |
| 114 | —H | —NH₂ | —CH₂CH₂OCH₃ | —CH₂CH₂OCH₃ | N | C | N | Z |
| 115 | —H | —NH₂ | —CH₂CH₂OC₂H₅ | —CH₂CH₂OC₂H₅ | N | C | N | X |
| 116 | —H | —NH₂ | —CH₂CH₂OC₂H₅ | —CH₂CH₂OC₂H₅ | N | C | N | Z |
| 117 | —H | —NH₂ | —CH₂CH₂OC₃H₇ | —CH₂CH₂OC₃H₇ | N | C | N | X |
| 118 | —H | —NH₂ | —CH₂CH₂OC₃H₇ | —CH₂CH₂OC₃H₇ | N | C | N | Z |
| 119 | —H | —NH₂ | —CH₂CH₂OC₆H₅ | —CH₂CF₃ | N | C | N | X |
| 120 | —H | —NH₂ | —CH₂CH₂OC₆H₅ | —CH₂CF₃ | N | C | N | Z |
| 121 | —H | —NH₂ | —CH₂CH₂OC₆H₅ | —CH₂CH₂OCH₃ | N | C | N | X |
| 122 | —H | —NH₂ | —CH₂CH₂OC₆H₅ | —CH₂CH₂OCH₃ | N | C | N | Z |
| 123 | —H | —NH₂ | —CH₂CH₂OC₆H₅ | —CH₂CH₂OC₆H₅ | N | C | N | X |
| 124 | —H | —NH₂ | —CH₂CH₂OC₆H₅ | —CH₂CH₂OC₆H₅ | N | C | N | Z |
| 125 | —H | —NH₂ | —CH₂CH₂OCH₂C₆H₅ | —CH₂CF₃ | N | C | N | X |
| 126 | —H | —NH₂ | —CH₂CH₂OCH₂C₆H₅ | —CH₂CF₃ | N | C | N | Z |
| 127 | —H | —NH₂ | —CH₂CH₂OCH₂C₆H₅ | —CH₂CH₂OCH₃ | N | C | N | X |
| 128 | —H | —NH₂ | —CH₂CH₂OCH₂C₆H₅ | —CH₂CH₂OCH₃ | N | C | N | Z |
| 129 | —H | —NH₂ | —CH₂CH₂OCH₂C₆H₅ | —CH₂CH₂OC₆H₅ | N | C | N | X |
| 130 | —H | —NH₂ | —CH₂CH₂OCH₂C₆H₅ | —CH₂CH₂OC₆H₅ | N | C | N | Z |
| 131 | —H | —NH₂ | —CH₂CH₂OCH₂C₆H₅ | —CH₂CH₂OCH₂C₆H₅ | N | C | N | X |
| 132 | —H | —NH₂ | —CH₂CH₂OCH₂C₆H₅ | —CH₂CH₂OCH₂C₆H₅ | N | C | N | Z |
| 133 | —H | —NH₂ | —CH₂CH₂OC₂H₄C₆H₅ | —CH₂CH₂OC₂H₄C₆H₅ | N | C | N | X |
| 134 | —H | —NH₂ | —CH₂CH₂OC₂H₄C₆H₅ | —CH₂CH₂OC₂H₄C₆H₅ | N | C | N | Z |
| 135 | —H | —NH₂ | —CH₂CH₂OC(O)CH₃ | —CH₂CF₃ | N | C | N | X |
| 136 | —H | —NH₂ | —CH₂CH₂OC(O)CH₃ | —CH₂CF₃ | N | C | N | Z |
| 137 | —H | —NH₂ | —CH₂CH₂OC(O)CH₃ | —CH₂CH₂OCH₃ | N | C | N | X |
| 138 | —H | —NH₂ | —CH₂CH₂OC(O)CH₃ | —CH₂CH₂OCH₃ | N | C | N | Z |

TABLE 1-continued

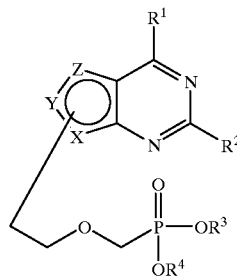

| Comp. No. | R¹ | R² | R³ | R⁴ | X | Y | Z | P.S. |
|---|---|---|---|---|---|---|---|---|
| 139 | —H | —NH₂ | —CH₂CH₂OC(O)CH₃ | —CH₂CH₂OC₆H₅ | N | C | N | X |
| 140 | —H | —NH₂ | —CH₂CH₂OC(O)CH₃ | —CH₂CH₂OC₆H₅ | N | C | N | Z |
| 141 | —H | —NH₂ | —CH₂CH₂OC(O)CH₃ | —CH₂CH₂OCH₂C₆H₅ | N | C | N | X |
| 142 | —H | —NH₂ | —CH₂CH₂OC(O)CH₃ | —CH₂CH₂OCH₂C₆H₅ | N | C | N | Z |
| 143 | —H | —NH₂ | —CH₂CH₂OC(O)CH₃ | —CH₂CH₂OC(O)CH₃ | N | C | N | X |
| 144 | —H | —NH₂ | —CH₂CH₂OC(O)CH₃ | —CH₂CH₂OC(O)CH₃ | N | C | N | Z |
| 145 | —H | —NH₂ | —CH₂CH₂OC(O)C₂H₅ | —CH₂CH₂OC(O)C₂H₅ | N | C | N | X |
| 146 | —H | —NH₂ | —CH₂CH₂OC(O)C₂H₅ | —CH₂CH₂OC(O)C₂H₅ | N | C | N | Z |
| 147 | —H | —NH₂ | —CH₂CH₂OC(O)C₃H₇ | —CH₂CH₂OC(O)C₃H₇ | N | C | N | X |
| 148 | —H | —NH₂ | —CH₂CH₂OC(O)C₃H₇ | —CH₂CH₂OC(O)C₃H₇ | N | C | N | Z |
| 149 | —H | —NH₂ | —CH₂CH₂OC(O)C₄H₉ | —CH₂CH₂OC(O)C₄H₉ | N | C | N | X |
| 150 | —H | —NH₂ | —CH₂CH₂OC(O)C₄H₉ | —CH₂CH₂OC(O)C₄H₉ | N | C | N | Z |
| 151 | —OH | —H | —CH₃ | —CF₂CF₃ | N | C | N | X |
| 152 | —OH | —H | —CH₃ | —CF₂CF₃ | N | C | N | Z |
| 153 | —OH | —H | —CH₃ | —CH₂CF₃ | N | C | N | X |
| 154 | —OH | —H | —CH₃ | —CH₂CF₃ | N | C | N | Z |
| 155 | —OH | —H | —CF₂CF₃ | —CF₂CF₃ | N | C | N | X |
| 156 | —OH | —H | —CF₂CF₃ | —CF₂CF₃ | N | C | N | Z |
| 157 | —OH | —H | —CF₂CF₃ | —CH₂CF₃ | N | C | N | X |
| 158 | —OH | —H | —CF₂CF₃ | —CH₂CF₃ | N | C | N | Z |
| 159 | —OH | —H | —CH₂CF₃ | —CH₂CF₃ | N | C | N | X |
| 160 | —OH | —H | —CH₂CF₃ | —CH₂CF₃ | N | C | N | Z |
| 161 | —OH | —H | —CH₂CH₂OCH₃ | —CH₂CF₃ | N | C | N | X |
| 162 | —OH | —H | —CH₂CH₂OCH₃ | —CH₂CF₃ | N | C | N | Z |
| 163 | —OH | —H | —CH₂CH₂OCH₃ | —CH₂CH₂OCH₃ | N | C | N | X |
| 164 | —OH | —H | —CH₂CH₂OCH₃ | —CH₂CH₂OCH₃ | N | C | N | Z |
| 165 | —OH | —H | —CH₂CH₂OC₂H₅ | —CH₂CH₂OC₂H₅ | N | C | N | X |
| 166 | —OH | —H | —CH₂CH₂OC₂H₅ | —CH₂CH₂OC₂H₅ | N | C | N | Z |
| 167 | —OH | —H | —CH₂CH₂OC₃H₇ | —CH₂CH₂OC₃H₇ | N | C | N | X |
| 168 | —OH | —H | —CH₂CH₂OC₃H₇ | —CH₂CH₂OC₃H₇ | N | C | N | Z |
| 169 | —OH | —H | —CH₂CH₂OC₆H₅ | —CH₂CF₃ | N | C | N | X |
| 170 | —OH | —H | —CH₂CH₂OC₆H₅ | —CH₂CF₃ | N | C | N | Z |
| 171 | —OH | —H | —CH₂CH₂OC₆H₅ | —CH₂CH₂OCH₃ | N | C | N | X |
| 172 | —OH | —H | —CH₂CH₂OC₆H₅ | —CH₂CH₂OCH₃ | N | C | N | Z |
| 173 | —OH | —H | —CH₂CH₂OC₆H₅ | —CH₂CH₂OC₆H₅ | N | C | N | X |
| 174 | —OH | —H | —CH₂CH₂OC₆H₅ | —CH₂CH₂OC₆H₅ | N | C | N | Z |
| 175 | —OH | —H | —CH₂CH₂OCH₂C₆H₅ | —CH₂CF₃ | N | C | N | X |
| 176 | —OH | —H | —CH₂CH₂OCH₂C₆H₅ | —CH₂CF₃ | N | C | N | Z |
| 177 | —OH | —H | —CH₂CH₂OCH₂C₆H₅ | —CH₂CH₂OCH₃ | N | C | N | X |
| 178 | —OH | —H | —CH₂CH₂OCH₂C₆H₅ | —CH₂CH₂OCH₃ | N | C | N | Z |
| 179 | —OH | —H | —CH₂CH₂OCH₂C₆H₅ | —CH₂CH₂OC₆H₅ | N | C | N | X |
| 180 | —OH | —H | —CH₂CH₂OCH₂C₆H₅ | —CH₂CH₂OC₆H₅ | N | C | N | Z |
| 181 | —OH | —H | —CH₂CH₂OCH₂C₆H₅ | —CH₂CH₂OCH₂C₆H₅ | N | C | N | X |
| 182 | —OH | —H | —CH₂CH₂OCH₂C₆H₅ | —CH₂CH₂OCH₂C₆H₅ | N | C | N | Z |
| 183 | —OH | —H | —CH₂CH₂OC₂H₄C₆H₅ | —CH₂CH₂OC₂H₄C₆H₅ | N | C | N | X |
| 184 | —OH | —H | —CH₂CH₂OC₂H₄C₆H₅ | —CH₂CH₂OC₂H₄C₆H₅ | N | C | N | Z |
| 185 | —OH | —H | —CH₂CH₂OC(O)CH₃ | —CH₂CF₃ | N | C | N | X |
| 186 | —OH | —H | —CH₂CH₂OC(O)CH₃ | —CH₂CF₃ | N | C | N | Z |
| 187 | —OH | —H | —CH₂CH₂OC(O)CH₃ | —CH₂CH₂OCH₃ | N | C | N | X |
| 188 | —OH | —H | —CH₂CH₂OC(O)CH₃ | —CH₂CH₂OCH₃ | N | C | N | Z |
| 189 | —OH | —H | —CH₂CH₂OC(O)CH₃ | —CH₂CH₂OC₆H₅ | N | C | N | X |
| 190 | —OH | —H | —CH₂CH₂OC(O)CH₃ | —CH₂CH₂OC₆H₅ | N | C | N | Z |
| 191 | —OH | —H | —CH₂CH₂OC(O)CH₃ | —CH₂CH₂OCH₂C₆H₅ | N | C | N | X |
| 192 | —OH | —H | —CH₂CH₂OC(O)CH₃ | —CH₂CH₂OCH₂C₆H₅ | N | C | N | Z |
| 193 | —OH | —H | —CH₂CH₂OC(O)CH₃ | —CH₂CH₂OC(O)CH₃ | N | C | N | X |
| 194 | —OH | —H | —CH₂CH₂OC(O)CH₃ | —CH₂CH₂OC(O)CH₃ | N | C | N | Z |
| 195 | —OH | —H | —CH₂CH₂OC(O)C₂H₅ | —CH₂CH₂OC(O)C₂H₅ | N | C | N | X |
| 196 | —OH | —H | —CH₂CH₂OC(O)C₂H₅ | —CH₂CH₂OC(O)C₂H₅ | N | C | N | Z |
| 197 | —OH | —H | —CH₂CH₂OC(O)C₃H₇ | —CH₂CH₂OC(O)C₃H₇ | N | C | N | X |
| 198 | —OH | —H | —CH₂CH₂OC(O)C₃H₇ | —CH₂CH₂OC(O)C₃H₇ | N | C | N | Z |
| 199 | —OH | —H | —CH₂CH₂OC(O)C₄H₉ | —CH₂CH₂OC(O)C₄H₉ | N | C | N | X |

TABLE 1-continued

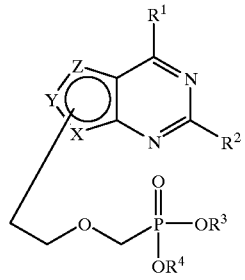

| Comp. No. | R¹ | R² | R³ | R⁴ | X | Y | Z | P.S. |
|---|---|---|---|---|---|---|---|---|
| 200 | —OH | —H | —CH$_2$CH$_2$OC(O)C$_4$H$_9$ | —CH$_2$CH$_2$OC(O)C$_4$H$_9$ | N | C | N | Z |
| 201 | —OH | —OH | —CH$_3$ | —CF$_2$CF$_3$ | N | C | N | X |
| 202 | —OH | —OH | —CH$_3$ | —CF$_2$CF$_3$ | N | C | N | Z |
| 203 | —OH | —OH | —CH$_3$ | —CH$_2$CF$_3$ | N | C | N | X |
| 204 | —OH | —OH | —CH$_3$ | —CH$_2$CF$_3$ | N | C | N | Z |
| 205 | —OH | —OH | —CF$_2$CF$_3$ | —CF$_2$CF$_3$ | N | C | N | X |
| 206 | —OH | —OH | —CF$_2$CF$_3$ | —CF$_2$CF$_3$ | N | C | N | Z |
| 207 | —OH | —OH | —CF$_2$CF$_3$ | —CH$_2$CF$_3$ | N | C | N | X |
| 208 | —OH | —OH | —CF$_2$CF$_3$ | —CH$_2$CF$_3$ | N | C | N | Z |
| 209 | —OH | —OH | —CH$_2$CF$_3$ | —CH$_2$CF$_3$ | N | C | N | X |
| 210 | —OH | —OH | —CH$_2$CF$_3$ | —CH$_2$CF$_3$ | N | C | N | Z |
| 211 | —OH | —OH | —CH$_2$CH$_2$OCH$_3$ | —CH$_2$CF$_3$ | N | C | N | X |
| 212 | —OH | —OH | —CH$_2$CH$_2$OCH$_3$ | —CH$_2$CF$_3$ | N | C | N | Z |
| 213 | —OH | —OH | —CH$_2$CH$_2$OCH$_3$ | —CH$_2$CH$_2$OCH$_3$ | N | C | N | X |
| 214 | —OH | —OH | —CH$_2$CH$_2$OCH$_3$ | —CH$_2$CH$_2$OCH$_3$ | N | C | N | Z |
| 215 | —OH | —OH | —CH$_2$CH$_2$OC$_2$H$_5$ | —CH$_2$CH$_2$OC$_2$H$_5$ | N | C | N | X |
| 216 | —OH | —OH | —CH$_2$CH$_2$OC$_2$H$_5$ | —CH$_2$CH$_2$OC$_2$H$_5$ | N | C | N | Z |
| 217 | —OH | —OH | —CH$_2$CH$_2$OC$_3$H$_7$ | —CH$_2$CH$_2$OC$_3$H$_7$ | N | C | N | X |
| 218 | —OH | —OH | —CH$_2$CH$_2$OC$_3$H$_7$ | —CH$_2$CH$_2$OC$_3$H$_7$ | N | C | N | Z |
| 219 | —OH | —OH | —CH$_2$CH$_2$OC$_6$H$_5$ | —CH$_2$CF$_3$ | N | C | N | X |
| 220 | —OH | —OH | —CH$_2$CH$_2$OC$_6$H$_5$ | —CH$_2$CF$_3$ | N | C | N | Z |
| 221 | —OH | —OH | —CH$_2$CH$_2$OC$_6$H$_5$ | —CH$_2$CH$_2$OCH$_3$ | N | C | N | X |
| 222 | —OH | —OH | —CH$_2$CH$_2$OC$_6$H$_5$ | —CH$_2$CH$_2$OCH$_3$ | N | C | N | Z |
| 223 | —OH | —OH | —CH$_2$CH$_2$OC$_6$H$_5$ | —CH$_2$CH$_2$OC$_6$H$_5$ | N | C | N | X |
| 224 | —OH | —OH | —CH$_2$CH$_2$OC$_6$H$_5$ | —CH$_2$CH$_2$OC$_6$H$_5$ | N | C | N | Z |
| 225 | —OH | —OH | —CH$_2$CH$_2$OCH$_2$C$_6$H$_5$ | —CH$_2$CF$_3$ | N | C | N | X |
| 226 | —OH | —OH | —CH$_2$CH$_2$OCH$_2$C$_6$H$_5$ | —CH$_2$CF$_3$ | N | C | N | Z |
| 227 | —OH | —OH | —CH$_2$CH$_2$OCH$_2$C$_6$H$_5$ | —CH$_2$CH$_2$OCH$_3$ | N | C | N | X |
| 228 | —OH | —OH | —CH$_2$CH$_2$OCH$_2$C$_6$H$_5$ | —CH$_2$CH$_2$OCH$_3$ | N | C | N | Z |
| 229 | —OH | —OH | —CH$_2$CH$_2$OCH$_2$C$_6$H$_5$ | —CH$_2$CH$_2$OC$_6$H$_5$ | N | C | N | X |
| 230 | —OH | —OH | —CH$_2$CH$_2$OCH$_2$C$_6$H$_5$ | —CH$_2$CH$_2$OC$_6$H$_5$ | N | C | N | Z |
| 231 | —OH | —OH | —CH$_2$CH$_2$OCH$_2$C$_6$H$_5$ | —CH$_2$CH$_2$OCH$_2$C$_6$H$_5$ | N | C | N | X |
| 232 | —OH | —OH | —CH$_2$CH$_2$OCH$_2$C$_6$H$_5$ | —CH$_2$CH$_2$OCH$_2$C$_6$H$_5$ | N | C | N | Z |
| 233 | —OH | —OH | —CH$_2$CH$_2$OC$_2$H$_4$C$_6$H$_5$ | —CH$_2$CH$_2$OC$_2$H$_4$C$_6$H$_5$ | N | C | N | X |
| 234 | —OH | —OH | —CH$_2$CH$_2$OC$_2$H$_4$C$_6$H$_5$ | —CH$_2$CH$_2$OC$_2$H$_4$C$_6$H$_5$ | N | C | N | Z |
| 235 | —OH | —OH | —CH$_2$CH$_2$OC(O)CH$_3$ | —CH$_2$CF$_3$ | N | C | N | X |
| 236 | —OH | —OH | —CH$_2$CH$_2$OC(O)CH$_3$ | —CH$_2$CF$_3$ | N | C | N | Z |
| 237 | —OH | —OH | —CH$_2$CH$_2$OC(O)CH$_3$ | —CH$_2$CH$_2$OCH$_3$ | N | C | N | X |
| 238 | —OH | —OH | —CH$_2$CH$_2$OC(O)CH$_3$ | —CH$_2$CH$_2$OCH$_3$ | N | C | N | Z |
| 239 | —OH | —OH | —CH$_2$CH$_2$OC(O)CH$_3$ | —CH$_2$CH$_2$OC$_6$H$_5$ | N | C | N | X |
| 240 | —OH | —OH | —CH$_2$CH$_2$OC(O)CH$_3$ | —CH$_2$CH$_2$OC$_6$H$_5$ | N | C | N | Z |
| 241 | —OH | —OH | —CH$_2$CH$_2$OC(O)CH$_3$ | —CH$_2$CH$_2$OCH$_2$C$_6$H$_5$ | N | C | N | X |
| 242 | —OH | —OH | —CH$_2$CH$_2$OC(O)CH$_3$ | —CH$_2$CH$_2$OCH$_2$C$_6$H$_5$ | N | C | N | Z |
| 243 | —OH | —OH | —CH$_2$CH$_2$OC(O)CH$_3$ | —CH$_2$CH$_2$OC(O)CH$_3$ | N | C | N | X |
| 244 | —OH | —OH | —CH$_2$CH$_2$OC(O)CH$_3$ | —CH$_2$CH$_2$OC(O)CH$_3$ | N | C | N | Z |
| 245 | —OH | —OH | —CH$_2$CH$_2$OC(O)C$_2$H$_5$ | —CH$_2$CH$_2$OC(O)C$_2$H$_5$ | N | C | N | X |
| 246 | —OH | —OH | —CH$_2$CH$_2$OC(O)C$_2$H$_5$ | —CH$_2$CH$_2$OC(O)C$_2$H$_5$ | N | C | N | Z |
| 247 | —OH | —OH | —CH$_2$CH$_2$OC(O)C$_3$H$_7$ | —CH$_2$CH$_2$OC(O)C$_3$H$_7$ | N | C | N | X |
| 248 | —OH | —OH | —CH$_2$CH$_2$OC(O)C$_3$H$_7$ | —CH$_2$CH$_2$OC(O)C$_3$H$_7$ | N | C | N | Z |
| 249 | —OH | —OH | —CH$_2$CH$_2$OC(O)C$_4$H$_9$ | —CH$_2$CH$_2$OC(O)C$_4$H$_9$ | N | C | N | X |
| 250 | —OH | —OH | —CH$_2$CH$_2$OC(O)C$_4$H$_9$ | —CH$_2$CH$_2$OC(O)C$_4$H$_9$ | N | C | N | Z |
| 251 | —OH | —NH$_2$ | —CH$_3$ | —CF$_2$CF$_3$ | N | C | N | X |
| 252 | —OH | —NH$_2$ | —CH$_3$ | —CF$_2$CF$_3$ | N | C | N | Z |
| 253 | —OH | —NH$_2$ | —CH$_3$ | —CH$_2$CF$_3$ | N | C | N | X |
| 254 | —OH | —NH$_2$ | —CH$_3$ | —CH$_2$CF$_3$ | N | C | N | Z |
| 255 | —OH | —NH$_2$ | —CF$_2$CF$_3$ | —CF$_2$CF$_3$ | N | C | N | X |
| 256 | —OH | —NH$_2$ | —CF$_2$CF$_3$ | —CF$_2$CF$_3$ | N | C | N | Z |
| 257 | —OH | —NH$_2$ | —CF$_2$CF$_3$ | —CH$_2$CF$_3$ | N | C | N | X |
| 258 | —OH | —NH$_2$ | —CF$_2$CF$_3$ | —CH$_2$CF$_3$ | N | C | N | Z |
| 259 | —OH | —NH$_2$ | —CH$_2$CF$_3$ | —CH$_2$CF$_3$ | N | C | N | X |
| 260 | —OH | —NH$_2$ | —CH$_2$CF$_3$ | —CH$_2$CF$_3$ | N | C | N | Z |

TABLE 1-continued

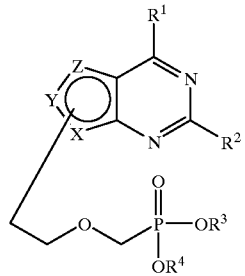

| Comp. No. | R¹ | R² | R³ | R⁴ | X | Y | Z | P.S. |
|---|---|---|---|---|---|---|---|---|
| 261 | —OH | —NH₂ | —CH₂CH₂OCH₃ | —CH₂CF₃ | N | C | N | X |
| 262 | —OH | —NH₂ | —CH₂CH₂OCH₃ | —CH₂CF₃ | N | C | N | Z |
| 263 | —OH | —NH₂ | —CH₂CH₂OCH₃ | —CH₂CH₂OCH₃ | N | C | N | X |
| 264 | —OH | —NH₂ | —CH₂CH₂OCH₃ | —CH₂CH₂OCH₃ | N | C | N | Z |
| 265 | —OH | —NH₂ | —CH₂CH₂OC₂H₅ | —CH₂CH₂OC₂H₅ | N | C | N | X |
| 26& | —OH | —NH₂ | —CH₂CH₂OC₂H₅ | —CH₂CH₂OC₂H₅ | N | C | N | Z |
| 267 | —OH | —NH₂ | —CH₂CH₂OC₃H₇ | —CH₂CH₂OC₃H₇ | N | C | N | X |
| 268 | —OH | —NH₂ | —CH₂CH₂OC₃H₇ | —CH₂CH₂OC₃H₇ | N | C | N | Z |
| 269 | —OH | —NH₂ | —CH₂CH₂OC₆H₅ | —CH₂CF₃ | N | C | N | X |
| 270 | —OH | —NH₂ | —CH₂CH₂OC₆H₅ | —CH₂CF₃ | N | C | N | Z |
| 271 | —OH | —NH₂ | —CH₂CH₂OC₆H₅ | —CH₂CH₂OCH₃ | N | C | N | X |
| 272 | —OH | —NH₂ | —CH₂CH₂OC₆H₅ | —CH₂CH₂OCH₃ | N | C | N | Z |
| 273 | —OH | —NH₂ | —CH₂CH₂OC₆H₅ | —CH₂CH₂OC₆H₅ | N | C | N | X |
| 274 | —OH | —NH₂ | —CH₂CH₂OC₆H₅ | —CH₂CH₂OC₆H₅ | N | C | N | Z |
| 275 | —OH | —NH₂ | —CH₂CH₂OCH₂C₆H₅ | —CH₂CF₃ | N | C | N | X |
| 276 | —OH | —NH₂ | —CH₂CH₂OCH₂C₆H₅ | —CH₂CF₃ | N | C | N | Z |
| 277 | —OH | —NH₂ | —CH₂CH₂OCH₂C₆H₅ | —CH₂CH₂OCH₃ | N | C | N | X |
| 278 | —OH | —NH₂ | —CH₂CH₂OCH₂C₆H₅ | —CH₂CH₂OCH₃ | N | C | N | Z |
| 279 | —OH | —NH₂ | —CH₂CH₂OCH₂C₆H₅ | —CH₂CH₂OC₆H₅ | N | C | N | X |
| 280 | —OH | —NH₂ | —CH₂CH₂OCH₂C₆H₅ | —CH₂CH₂OC₆H₅ | N | C | N | Z |
| 281 | —OH | —NH₂ | —CH₂CH₂OCH₂C₆H₅ | —CH₂CH₂OCH₂C₆H₅ | N | C | N | X |
| 282 | —OH | —NH₂ | —CH₂CH₂OCH₂C₆H₅ | —CH₂CH₂OCH₂C₆H₅ | N | C | N | Z |
| 283 | —OH | —NH₂ | —CH₂CH₂OC₂H₄C₆H₅ | —CH₂CH₂OC₂H₄C₆H₅ | N | C | N | X |
| 284 | —OH | —NH₂ | —CH₂CH₂OC₂H₄C₆H₅ | —CH₂CH₂OC₂H₄C₆H₅ | N | C | N | Z |
| 285 | —OH | —NH₂ | —CH₂CH₂OC(O)CH₃ | —CH₂CF₃ | N | C | N | X |
| 286 | —OH | —NH₂ | —CH₂CH₂OC(O)CH₃ | —CH₂CF₃ | N | C | N | Z |
| 287 | —OH | —NH₂ | —CH₂CH₂OC(O)CH₃ | —CH₂CH₂OCH₃ | N | C | N | X |
| 288 | —OH | —NH₂ | —CH₂CH₂OC(O)CH₃ | —CH₂CH₂OCH₃ | N | C | N | Z |
| 289 | —OH | —NH₂ | —CH₂CH₂OC(O)CH₃ | —CH₂CH₂OC₆H₅ | N | C | N | X |
| 290 | —OH | —NH₂ | —CH₂CH₂OC(O)CH₃ | —CH₂CH₂OC₆H₅ | N | C | N | Z |
| 291 | —OH | —NH₂ | —CH₂CH₂OC(O)CH₃ | —CH₂CH₂OCH₂C₆H₅ | N | C | N | X |
| 292 | —OH | —NH₂ | —CH₂CH₂OC(O)CH₃ | —CH₂CH₂OCH₂C₆H₅ | N | C | N | Z |
| 293 | —OH | —NH₂ | —CH₂CH₂OC(O)CH₃ | —CH₂CH₂OC(O)CH₃ | N | C | N | X |
| 294 | —OH | —NH₂ | —CH₂CH₂OC(O)CH₃ | —CH₂CH₂OC(O)CH₃ | N | C | N | Z |
| 295 | —OH | —NH₂ | —CH₂CH₂OC(O)C₂H₅ | —CH₂CH₂OC(O)C₂H₅ | N | C | N | X |
| 296 | —OH | —NH₂ | —CH₂CH₂OC(O)C₂H₅ | —CH₂CH₂OC(O)C₂H₅ | N | C | N | Z |
| 297 | —OH | —NH₂ | —CH₂CH₂OC(O)C₃H₇ | —CH₂CH₂OC(O)C₃H₇ | N | C | N | X |
| 298 | —OH | —NH₂ | —CH₂CH₂OC(O)C₃H₇ | —CH₂CH₂OC(O)C₃H₇ | N | C | N | Z |
| 299 | —OH | —NH₂ | —CH₂CH₂OC(O)C₄H₆ | —CH₂CH₂OC(O)C₄H₉ | N | C | N | X |
| 300 | —OH | —NH₂ | —CH₂CH₂OC(O)C₄H₆ | —CH₂CH₂OC(O)C₄H₆ | N | C | N | Z |
| 301 | —NH₂ | —H | —CH₃ | —CF₂CF₃ | N | C | N | X |
| 302 | —NH₂ | —H | —CH₃ | —CF₂CF₃ | N | C | N | Z |
| 303 | —NH₂ | —H | —CH₃ | —CH₂CF₃ | N | C | N | X |
| 304 | —NH₂ | —H | —CH₃ | —CH₂CF₃ | N | C | N | z |
| 305 | —NH₂ | —H | —CF₂CF₃ | —CF₂CF₃ | N | C | N | X |
| 306 | —NH₂ | —H | —CF₂CF₃ | —CF₂CF₃ | N | C | N | Z |
| 307 | —NH₂ | —H | —CF₂CF₃ | —CH₂CF₃ | N | C | N | X |
| 308 | —NH₂ | —H | —CF₂CF₃ | —CH₂CF₃ | N | C | N | Z |
| 309 | —NH₂ | —H | —CH₂CF₃ | —CH₂CF₃ | N | C | N | X |
| 310 | —NH₂ | —H | —CH₂CF₃ | —CH₂CF₃ | N | C | N | Z |
| 311 | —NH₂ | —H | —CH₂CH₂OCH₃ | —CH₂CF₃ | N | C | N | X |
| 312 | —NH₂ | —H | —CH₂CH₂OCH₃ | —CH₂CF₃ | N | C | N | Z |
| 313 | —NH₂ | —H | —CH₂CH₂OCH₃ | —CH₂CH₂OCH₃ | N | C | N | X |
| 314 | —NH₂ | —H | —CH₂CH₂OCH₃ | —CH₂CH₂OCH₃ | N | C | N | Z |
| 315 | —NH₂ | —H | —CH₂CH₂OC₂H₅ | —CH₂CH₂OC₂H₅ | N | C | N | X |
| 316 | —NH₂ | —H | —CH₂CH₂OC₂H₅ | —CH₂CH₂OC₂H₅ | N | C | N | Z |
| 317 | —NH₂ | —H | —CH₂CH₂OC₃H₇ | —CH₂CH₂OC₃H₇ | N | C | N | X |
| 318 | —NH₂ | —H | —CH₂CH₂OC₃H₇ | —CH₂CH₂OC₃H₇ | N | C | N | Z |
| 319 | —NH₂ | —H | —CH₂CH₂OC₆H₅ | —CH₂CF₃ | N | C | N | X |
| 320 | —NH₂ | —H | —CH₂CH₂OC₆H₅ | —CH₂CF₃ | N | C | N | Z |
| 321 | —NH₂ | —H | —CH₂CH₂OC₆H₅ | —CH₂CH₂OCH₃ | N | C | N | X |

TABLE 1-continued

| Comp. No. | R¹ | R² | R³ | R⁴ | X | Y | Z | P.S. |
|---|---|---|---|---|---|---|---|---|
| 322 | —NH₂ | —H | —CH₂CH₂OC₆H₅ | —CH₂CH₂OCH₃ | N | C | N | Z |
| 323 | —NH₂ | —H | —CH₂CH₂OC₆H₅ | —CH₂CH₂OC₆H₅ | N | C | N | X |
| 324 | —NH₂ | —H | —CH₂CH₂OC₆H₅ | —CH₂CH₂OC₆H₅ | N | C | N | Z |
| 325 | —NH₂ | —H | —CH₂CH₂OCH₂C₆H₅ | —CH₂CF₃ | N | C | N | X |
| 326 | —NH₂ | —H | —CH₂CH₂OCH₂C₆H₅ | —CH₂CF₃ | N | C | N | Z |
| 327 | —NH₂ | —H | —CH₂CH₂OCH₂C₆H₅ | —CH₂CH₂OCH₃ | N | C | N | X |
| 328 | —NH₂ | —H | —CH₂CH₂OCH₂C₆H₅ | —CH₂CH₂OCH₃ | N | C | N | Z |
| 329 | —NH₂ | —H | —CH₂CH₂OCH₂C₆H₅ | —CH₂CH₂OC₆H₅ | N | C | N | X |
| 330 | —NH₂ | —H | —CH₂CH₂OCH₂C₆H₅ | —CH₂CH₂OC₆H₅ | N | C | N | Z |
| 331 | —NH₂ | —H | —CH₂CH₂OCH₂C₆H₅ | —CH₂CH₂OCH₂C₆H₅ | N | C | N | X |
| 332 | —NH₂ | —H | —CH₂CH₂OCH₂C₆H₅ | —CH₂CH₂OCH₂C₆H₅ | N | C | N | Z |
| 333 | —NH₂ | —H | —CH₂CH₂OC₂H₄C₆H₅ | —CH₂CH₂OC₂H₄C₆H₅ | N | C | N | X |
| 334 | —NH₂ | —H | —CH₂CH₂OC₂H₄C₆H₅ | —CH₂CH₂OC₂H₄C₆H₅ | N | C | N | Z |
| 335 | —NH₂ | —H | —CH₂CH₂OC(O)CH₃ | —CH₂CF₃ | N | C | N | X |
| 336 | —NH₂ | —H | —CH₂CH₂OC(O)CH₃ | —CH₂CF₃ | N | C | N | Z |
| 337 | —NH₂ | —H | —CH₂CH₂OC(O)CH₃ | —CH₂CH₂OCH₃ | N | C | N | X |
| 338 | —NH₂ | —H | —CH₂CH₂OC(O)CH₃ | —CH₂CH₂OCH₃ | N | C | N | Z |
| 339 | —NH₂ | —H | —CH₂CH₂OC(O)CH₃ | —CH₂CH₂OC₆H₅ | N | C | N | X |
| 340 | —NH₂ | —H | —CH₂CH₂OC(O)CH₃ | —CH₂CH₂OC₆H₅ | N | C | N | Z |
| 341 | —NH₂ | —H | —CH₂CH₂OC(O)CH₃ | —CH₂CH₂OCH₂C₆H₅ | N | C | N | X |
| 342 | —NH₂ | —H | —CH₂CH₂OC(O)CH₃ | —CH₂CH₂OCH₂C₆H₅ | N | C | N | Z |
| 343 | —NH₂ | —H | —CH₂CH₂OC(O)CH₃ | —CH₂CH₂OC(O)CH₃ | N | C | N | X |
| 344 | —NH₂ | —H | —CH₂CH₂OC(O)CH₃ | —CH₂CH₂OC(O)CH₃ | N | C | N | Z |
| 345 | —NH₂ | —H | —CH₂CH₂OC(O)C₂H₅ | —CH₂CH₂OC(O)C₂H₅ | N | C | N | X |
| 346 | —NH₂ | —H | —CH₂CH₂OC(O)C₂H₅ | —CH₂CH₂OC(O)C₂H₅ | N | C | N | Z |
| 347 | —NH₂ | —H | —CH₂CH₂OC(O)C₃H₇ | —CH₂CH₂OC(O)C₃H₇ | N | C | N | X |
| 348 | —NH₂ | —H | —CH₂CH₂OC(O)C₃H₇ | —CH₂CH₂OC(O)C₃H₇ | N | C | N | Z |
| 349 | —NH₂ | —H | —CH₂CH₂OC(O)C₄H₉ | —CH₂CH₂OC(O)C₄H₉ | N | C | N | X |
| 350 | —NH₂ | —H | —CH₂CH₂OC(O)C₄H₉ | —CH₂CH₂OC(O)C₄H₉ | N | C | N | Z |
| 351 | —NH₂ | —I | —CH₃ | —CF₂CF₃ | N | C | N | X |
| 352 | —NH₂ | —I | —CH₃ | —CF₂CF₃ | N | C | N | Z |
| 353 | —NH₂ | —I | —CH₃ | —CH₂CF₃ | N | C | N | X |
| 354 | —NH₂ | —I | —CH₃ | —CH₂CF₃ | N | C | N | Z |
| 355 | —NH₂ | —I | —CF₂CF₃ | —CF₂CF₃ | N | C | N | X |
| 356 | —NH₂ | —I | —CF₂CF₃ | —CF₂CF₃ | N | C | N | Z |
| 357 | —NH₂ | —I | —CF₂CF₃ | —CH₂CF₃ | N | C | N | X |
| 358 | —NH₂ | —I | —CF₂CF₃ | —CH₂CF₃ | N | C | N | Z |
| 359 | —NH₂ | —I | —CH₂CF₃ | —CH₂CF₃ | N | C | N | X |
| 360 | —NH₂ | —I | —CH₂CF₃ | —CH₂CF₃ | N | C | N | Z |
| 361 | —NH₂ | —I | —CH₂CH₂OCH₃ | —CH₂CF₃ | N | C | N | X |
| 362 | —NH₂ | —I | —CH₂CH₂OCH₃ | —CH₂CF₃ | N | C | N | Z |
| 368 | —NH₂ | —I | —CH₂CH₂OCH₃ | —CH₂CH₂OCH₃ | N | C | N | X |
| 364 | —NH₂ | —I | —CH₂CH₂OCH₃ | —CH₂CH₂OCH₃ | N | C | N | Z |
| 365 | —NH₂ | —I | —CH₂CH₂OC₂H₅ | —CH₂CH₂OC₂H₅ | N | C | N | X |
| 366 | —NH₂ | —I | —CH₂CH₂OC₂H₅ | —CH₂CH₂OC₂H₅ | N | C | N | Z |
| 367 | —NH₂ | —I | —CH₂CH₂OC₃H₇ | —CH₂CH₂OC₃H₇ | N | C | N | X |
| 368 | —NH₂ | —I | —CH₂CH₂OC₃H₇ | —CH₂CH₂OC₃H₇ | N | C | N | Z |
| 369 | —NH₂ | —I | —CH₂CH₂OC₆H₅ | —CH₂CF₃ | N | C | N | X |
| 370 | —NH₂ | —I | —CH₂CH₂OC₆H₅ | —CH₂CF₃ | N | C | N | Z |
| 371 | —NH₂ | —I | —CH₂CH₂OC₆H₅ | —CH₂CH₂OCH₃ | N | C | N | X |
| 372 | —NH₂ | —I | —CH₂CH₂OC₆H₅ | —CH₂CH₂OCH₃ | N | C | N | Z |
| 373 | —NH₂ | —I | —CH₂CH₂OC₆H₅ | —CH₂CH₂OC₆H₅ | N | C | N | X |
| 374 | —NH₂ | —I | —CH₂CH₂OC₆H₅ | —CH₂CH₂OC₆H₅ | N | C | N | Z |
| 375 | —NH₂ | —I | —CH₂CH₂OCH₂C₆H₅ | —CH₂CF₃ | N | C | N | X |
| 376 | —NH₂ | —I | —CH₂CH₂OCH₂C₆H₅ | —CH₂CF₃ | N | C | N | Z |
| 377 | —NH₂ | —I | —CH₂CH₂OCH₂C₆H₅ | —CH₂CH₂OCH₃ | N | C | N | X |
| 378 | —NH₂ | —I | —CH₂CH₂OCH₂C₆H₅ | —CH₂CH₂OCH₃ | N | C | N | Z |
| 379 | —NH₂ | —I | —CH₂CH₂OCH₂C₆H₅ | —CH₂CH₂OC₆H₅ | N | C | N | X |
| 380 | —NH₂ | —I | —CH₂CH₂OCH₂C₆H₅ | —CH₂CH₂OC₆H₅ | N | C | N | Z |
| 381 | —NH₂ | —I | —CH₂CH₂OCH₂C₆H₅ | —CH₂CH₂OCH₂C₆H₅ | N | C | N | X |
| 382 | —NH₂ | —I | —CH₂CH₂OCH₂C₆H₅ | —CH₂CH₂OCH₂C₆H₅ | N | C | N | Z |

TABLE 1-continued

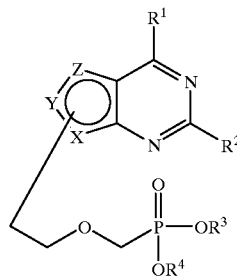

| Comp. No. | R¹ | R² | R³ | R⁴ | X | Y | Z | P.S. |
|---|---|---|---|---|---|---|---|---|
| 383 | —NH₂ | —I | —CH₂CH₂OC₂H₄C₆H₅ | —CH₂CH₂OC₂H₄C₆H₅ | N | C | N | X |
| 384 | —NH₂ | —I | —CH₂CH₂OC₂H₄C₆H₅ | —CH₂CH₂OC₂H₄C₆H₅ | N | C | N | Z |
| 385 | —NH₂ | —I | —CH₂CH₂OC(O)CH₃ | —CH₂CF₃ | N | C | N | X |
| 386 | —NH₂ | —I | —CH₂CH₂OC(O)CH₃ | —CH₂CF₃ | N | C | N | Z |
| 387 | —NH₂ | —I | —CH₂CH₂OC(O)CH₃ | —CH₂CH₂OCH₃ | N | C | N | X |
| 388 | —NH₂ | —I | —CH₂CH₂OC(O)CH₃ | —CH₂CH₂OCH₃ | N | C | N | Z |
| 389 | —NH₂ | —I | —CH₂CH₂OC(O)CH₃ | —CH₂CH₂OC₆H₅ | N | C | N | X |
| 390 | —NH₂ | —I | —CH₂CH₂OC(O)CH₃ | —CH₂CH₂OC₆H₅ | N | C | N | Z |
| 391 | —NH₂ | —I | —CH₂CH₂OC(O)CH₃ | —CH₂CH₂OCH₂C₆H₅ | N | C | N | X |
| 392 | —NH₂ | —I | —CH₂CH₂OC(O)CH₃ | —CH₂CH₂OCH₂C₆H₅ | N | C | N | Z |
| 393 | —NH₂ | —I | —CH₂CH₂OC(O)CH₃ | —CH₂CH₂CC(O)CH₃ | N | C | N | X |
| 394 | —NH₂ | —I | —CH₂CH₂OC(O)CH₃ | —CH₂CH₂OC(O)CH₃ | N | C | N | Z |
| 395 | —NH₂ | —I | —CH₂CH₂OC(O)C₂H₅ | —CH₂CH₂OC(O)C₂H₅ | N | C | N | X |
| 396 | —NH₂ | —I | —CH₂CH₂OC(O)C₂H₅ | —CH₂CH₂OC(O)C₂H₅ | N | C | N | Z |
| 397 | —NH₂ | —I | —CH₂CH₂OC(O)C₃H₇ | —CH₂CH₂OC(O)C₃H₇ | N | C | N | X |
| 398 | —NH₂ | —I | —CH₂CH₂OC(O)C₃H₇ | —CH₂CH₂OC(O)C₃H₇ | N | C | N | Z |
| 399 | —NH₂ | —I | —CH₂CH₂OC(O)C₄H₉ | —CH₂CH₂OC(O)C₄H₉ | N | C | N | X |
| 400 | —NH₂ | —I | —CH₂CH₂OC(O)C₄H₉ | —CH₂CH₂OC(O)C₄H₉ | N | C | N | Z |
| 401 | —NH₂ | —OH | —CH₃ | —CF₂CF₃ | N | C | N | X |
| 402 | —NH₂ | —OH | —CH₃ | —CF₂CF₃ | N | C | N | Z |
| 403 | —NH₂ | —OH | —CH₃ | —CH₂CF₃ | N | C | N | X |
| 404 | —NH₂ | —OH | —CH₃ | —CH₂CF₃ | N | C | N | Z |
| 405 | —NH₂ | —OH | —CF₂CF₃ | —CF₂CF₃ | N | C | N | X |
| 406 | —NH₂ | —OH | —CF₂CF₃ | —CF₂CF₃ | N | C | N | Z |
| 407 | —NH₂ | —OH | —CF₂CF₃ | —CH₂CF₃ | N | C | N | X |
| 408 | —NH₂ | —OH | —CF₂CF₃ | —CH₂CF₃ | N | C | N | Z |
| 409 | —NH₂ | —OH | —CH₂CF₃ | —CH₂CF₃ | N | C | N | X |
| 410 | —NH₂ | —OH | —CH₂CF₃ | —CH₂CF₃ | N | C | N | Z |
| 411 | —NH₂ | —OH | —CH₂CH₂OCH₃ | —CH₂CF₃ | N | C | N | X |
| 412 | —NH₂ | —OH | —CH₂CH₂OCH₃ | —CH₂CF₃ | N | C | N | Z |
| 413 | —NH₂ | —OH | —CH₂CH₂OCH₃ | —CH₂CH₂OCH₃ | N | C | N | X |
| 414 | —NH₂ | —OH | —CH₂CH₂OCH₃ | —CH₂CH₂OCH₃ | N | C | N | Z |
| 415 | —NH₂ | —OH | —CH₂CH₂OC₂H₅ | —CH₂CH₂OC₂H₅ | N | C | N | X |
| 416 | —NH₂ | —OH | —CH₂CH₂OC₂H₅ | —CH₂CH₂OC₂H₅ | N | C | N | z |
| 417 | —NH₂ | —OH | —CH₂CH₂OC₃H₇ | —CH₂CH₂OC₃H₇ | N | C | N | X |
| 418 | —NH₂ | —OH | —CH₂CH₂OC₃H₇ | —CH₂CH₂OC₃H₇ | N | C | N | Z |
| 419 | —NH₂ | —OH | —CH₂CH₂OC₆H₅ | —CH₂CF₃ | N | C | N | X |
| 420 | —NH₂ | —OH | —CH₂CH₂OC₆H₅ | —CH₂CF₃ | N | C | N | Z |
| 421 | —NH₂ | —OH | —CH₂CH₂OC₆H₅ | —CH₂CH₂OCH₃ | N | C | N | X |
| 422 | —NH₂ | —OH | —CH₂CH₂OC₆H₅ | —CH₂CH₂OCH₃ | N | C | N | Z |
| 423 | —NH₂ | —OH | —CH₂CH₂OC₆H₅ | —CH₂CH₂OC₆H₅ | N | C | N | X |
| 424 | —NH₂ | —OH | —CH₂CH₂OC₆H₅ | —CH₂CH₂OC₆H₅ | N | C | N | Z |
| 425 | —NH₂ | —OH | —CH₂CH₂OCH₂C₆H₅ | —CH₂CF₃ | N | C | N | X |
| 426 | —NH₂ | —OH | —CH₂CH₂OCH₂C₆H₅ | —CH₂CF₃ | N | C | N | Z |
| 427 | —NH₂ | —OH | —CH₂CH₂OCH₂C₆H₅ | —CH₂CH₂OCH₃ | N | C | N | X |
| 428 | —NH₂ | —OH | —CH₂CH₂OCH₂C₆H₅ | —CH₂CH₂OCH₃ | N | C | N | Z |
| 429 | —NH₂ | —OH | —CH₂CH₂OCH₂C₆H₅ | —CH₂CH₂OC₆H₅ | N | C | N | X |
| 430 | —NH₂ | —OH | —CH₂CH₂OCH₂C₆H₅ | —CH₂CH₂OC₆H₅ | N | C | N | Z |
| 431 | —NH₂ | —OH | —CH₂CH₂OCH₂C₆H₅ | —CH₂CH₂OCH₂C₆H₅ | N | C | N | X |
| 432 | —NH₂ | —OH | —CH₂CH₂OCH₂C₆H₅ | —CH₂CH₂OCH₂C₆H₅ | N | C | N | Z |
| 433 | —NH₂ | —OH | —CH₂CH₂OC₂H₄C₆H₅ | —CH₂CH₂OC₂H₄C₆H₅ | N | C | N | X |
| 434 | —NH₂ | —OH | —CH₂CH₂OC₂H₄C₆H₅ | —CH₂CH₂OC₂H₄C₆H₅ | N | C | N | Z |
| 435 | —NH₂ | —OH | —CH₂CH₂OC(O)CH₃ | —CH₂CF₃ | N | C | N | X |
| 436 | —NH₂ | —OH | —CH₂CH₂OC(O)CH₃ | —CH₂CF₃ | N | C | N | Z |
| 437 | —NH₂ | —OH | —CH₂CH₂OC(O)CH₃ | —CH₂CH₂OCH₃ | N | C | N | X |
| 438 | —NH₂ | —OH | —CH₂CH₂OC(O)CH₃ | —CH₂CH₂OCH₃ | N | C | N | Z |
| 439 | —NH₂ | —OH | —CH₂CH₂OC(O)CH₃ | —CH₂CH₂OC₆H₅ | N | C | N | X |
| 440 | —NH₂ | —OH | —CH₂CH₂OC(O)CH₃ | —CH₂CH₂OC₆H₅ | N | C | N | Z |
| 441 | —NH₂ | —OH | —CH₂CH₂OC(O)CH₃ | —CH₂CH₂OCH₂C₆H₅ | N | C | N | X |
| 442 | —NH₂ | —OH | —CH₂CH₂OC(O)CH₃ | —CH₂CH₂OCH₂C₆H₅ | N | C | N | Z |
| 443 | —NH₂ | —OH | —CH₂CH₂OC(O)CH₃ | —CH₂CH₂OC(O)CH₃ | N | C | N | X |

TABLE 1-continued

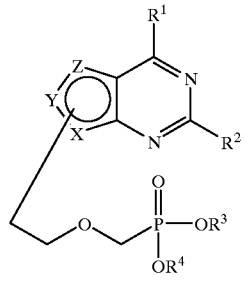

| Comp. No. | R¹ | R² | R³ | R⁴ | X | Y | Z | P.S. |
|---|---|---|---|---|---|---|---|---|
| 444 | —NH₂ | —OH | —CH₂CH₂OC(O)CH₃ | —CH₂CH₂OC(O)CH₃ | N | C | N | Z |
| 445 | —NH₂ | —OH | —CH₂CH₂OC(O)C₂H₅ | —CH₂CH₂OC(O)C₂H₅ | N | C | N | X |
| 446 | —NH₂ | —OH | —CH₂CH₂OC(O)C₂H₅ | —CH₂CH₂OC(O)C₂H₅ | N | C | N | Z |
| 447 | —NH₂ | —OH | —CH₂CH₂OC(O)C₃H₇ | —CH₂CH₂OC(O)C₃H₇ | N | C | N | X |
| 448 | —NH₂ | —OH | —CH₂CH₂OC(O)C₃H₇ | —CH₂CH₂OC(O)C₃H₇ | N | C | N | Z |
| 449 | —NH₂ | —OH | —CH₂CH₂OC(O)C₄H₉ | —CH₂CH₂OC(O)C₄H₉ | N | C | N | X |
| 450 | —NH₂ | —OH | —CH₂CH₂OC(O)C₄H₉ | —CH₂CH₂OC(O)C₄H₉ | N | C | N | Z |
| 451 | —NH₂ | —NH₂ | —CH₃ | —CF₂CF₃ | N | C | N | X |
| 452 | —NH₂ | —NH₂ | —CH₃ | —CF₂CF₃ | N | C | N | Z |
| 453 | —NH₂ | —NH₂ | —CH₃ | —CH₂CF₃ | N | C | N | X |
| 454 | —NH₂ | —NH₂ | —CH₃ | —CH₂CF₃ | N | C | N | Z |
| 455 | —NH₂ | —NH₂ | —CF₂CF₃ | —CF₂CF₃ | N | C | N | X |
| 456 | —NH₂ | —NH₂ | —CF₂CF₃ | —CF₂CF₃ | N | C | N | Z |
| 457 | —NH₂ | —NH₂ | —CF₂CF₃ | —CH₂CF₃ | N | C | N | X |
| 458 | —NH₂ | —NH₂ | —CF₂CF₃ | —CH₂CF₃ | N | C | N | Z |
| 459 | —NH₂ | —NH₂ | —CH₂CF₃ | —CH₂CF₃ | N | C | N | X |
| 460 | —NH₂ | —NH₂ | —CH₂CF₃ | —CH₂CF₃ | N | C | N | Z |
| 461 | —NH₂ | —NH₂ | —CH₂CH₂OCH₃ | —CH₂CF₃ | N | C | N | X |
| 462 | —NH₂ | —NH₂ | —CH₂CH₂OCH₃ | —CH₂CF₃ | N | C | N | Z |
| 463 | —NH₂ | —NH₂ | —CH₂CH₂OCH₃ | —CH₂CH₂OCH₃ | N | C | N | X |
| 464 | —NH₂ | —NH₂ | —CH₂CH₂OCH₃ | —CH₂CH₂OCH₃ | N | C | N | Z |
| 465 | —NH₂ | —NH₂ | —CH₂CH₂OC₂H₅ | —CH₂CH₂OC₂H₅ | N | C | N | X |
| 466 | —NH₂ | —NH₂ | —CH₂CH₂OC₂H₅ | —CH₂CH₂OC₂H₅ | N | C | N | Z |
| 467 | —NH₂ | —NH₂ | —CH₂CH₂OC₃H₇ | —CH₂CH₂OC₃H₇ | N | C | N | X |
| 468 | —NH₂ | —NH₂ | —CH₂CH₂OC₃H₇ | —CH₂CH₂OC₃H₇ | N | C | N | Z |
| 469 | —NH₂ | —NH₂ | —CH₂CH₂OC₆H₅ | —CH₂CF₃ | N | C | N | X |
| 470 | —NH₂ | —NH₂ | —CH₂CH₂OC₆H₅ | —CH₂CF₃ | N | C | N | Z |
| 471 | —NH₂ | —NH₂ | —CH₂CH₂OC₆H₅ | —CH₂CH₂OCH₃ | N | C | N | X |
| 472 | —NH₂ | —NH₂ | —CH₂CH₂OC₆H₅ | —CH₂CH₂OCH₃ | N | C | N | Z |
| 473 | —NH₂ | —NH₂ | —OH₂CH₂OC₆H₅ | —CH₂CH₂OC₆H₅ | N | C | N | X |
| 474 | —NH₂ | —NH₂ | —CH₂CH₂OC₆H₅ | —CH₂CH₂OC₆H₅ | N | C | N | Z |
| 475 | —NH₂ | —NH₂ | —CH₂CH₂OCH₂C₆H₅ | —CH₂CF₃ | N | C | N | X |
| 476 | —NH₂ | —NH₂ | —CH₂CH₂OCH₂C₆H₅ | —CH₂CF₃ | N | C | N | Z |
| 477 | —NH₂ | —NH₂ | —CH₂CH₂OCH₂C₆H₅ | —CH₂CH₂OCH₃ | N | C | N | X |
| 478 | —NH₂ | —NH₂ | —CH₂CH₂OCH₂C₆H₅ | —CH₂CH₂OCH₃ | N | C | N | Z |
| 479 | —NH₂ | —NH₂ | —CH₂CH₂OCH₂C₆H₅ | —CH₂CH₂OC₆H₅ | N | C | N | X |
| 480 | —NH₂ | —NH₂ | —CH₂CH₂OCH₂C₆H₅ | —CH₂CH₂OC₆H₅ | N | C | N | Z |
| 481 | —NH₂ | —NH₂ | —CH₂CH₂OCH₂C₆H₅ | —CH₂CH₂OCH₂C₆H₅ | N | C | N | X |
| 482 | —NH₂ | —NH₂ | —CH₂CH₂OCH₂C₆H₅ | —CH₂CH₂OCH₂C₆H₅ | N | C | N | Z |
| 483 | —NH₂ | —NH₂ | —CH₂CH₂OC₂H₄C₆H₅ | —CH₂CH₂OC₂H₄C₆H₅ | N | C | N | X |
| 484 | —NH₂ | —NH₂ | —CH₂CH₂OC₂H₄C₆H₅ | —CH₂CH₂OC₂H₄C₆H₅ | N | C | N | Z |
| 485 | —NH₂ | —NH₂ | —CH₂CH₂OC(O)CH₃ | —CH₂CF₃ | N | C | N | X |
| 486 | —NH₂ | —NH₂ | —CH₂CH₂OC(O)CH₃ | —CH₂CF₃ | N | C | N | Z |
| 487 | —NH₂ | —NH₂ | —CH₂CH₂OC(O)CH₃ | —CH₂CH₂OCH₃ | N | C | N | X |
| 488 | —NH₂ | —NH₂ | —CH₂CH₂OC(O)CH₃ | —CH₂CH₂OCH₃ | N | C | N | Z |
| 489 | —NH₂ | —NH₂ | —CH₂CH₂OC(O)CH₃ | —CH₂CH₂OC₆H₅ | N | C | N | X |
| 490 | —NH₂ | —NH₂ | —CH₂CH₂OC(O)CH₃ | —CH₂CH₂OC₆H₅ | N | C | N | Z |
| 491 | —NH₂ | —NH₂ | —CH₂CH₂OC(O)CH₃ | —CH₂CH₂OCH₂C₆H₅ | N | C | N | X |
| 492 | —NH₂ | —NH₂ | —CH₂CH₂OC(O)CH₃ | —CH₂CH₂OCH₂C₆H₅ | N | C | N | Z |
| 493 | —NH₂ | —NH₂ | —CH₂CH₂OC(O)CH₃ | —CH₂CH₂O(O)CH₃ | N | C | N | X |
| 494 | —NH₂ | —NH₂ | —CH₂CH₂OC(O)CH₃ | —CH₂CH₂OC(O)CH₃ | N | C | N | Z |
| 495 | —NH₂ | —NH₂ | —CH₂CH₂OC(O)C₂H₅ | —CH₂CH₂OC(O)C₂H₅ | N | C | N | X |
| 496 | —NH₂ | —NH₂ | —CH₂CH₂OC(O)C₂H₅ | —CH₂CH₂OC(O)C₂H₅ | N | C | N | Z |
| 497 | —NH₂ | —NH₂ | —CH₂CH₂OC(O)C₃H₇ | —CH₂CH₂OC(O)C₃H₇ | N | C | N | X |
| 498 | —NH₂ | —NH₂ | —CH₂CH₂OC(O)C₃H₇ | —CH₂CH₂OC(O)C₃H₇ | N | C | N | Z |
| 499 | —NH₂ | —NH₂ | —CH₂CH₂OC(O)C₄H₉ | —CH₂CH₂OC(O)C₄H₉ | N | C | N | X |
| 500 | —NH₂ | —NH₂ | —CH₂CH₂OC(O)C₄H₉ | —CH₂CH₂OC(O)C₄H₉ | N | C | N | Z |
| 501 | —Cl | —NH₂ | —CH₃ | —CF₂CF₃ | N | C | N | X |
| 502 | —Cl | —NH₂ | —CH₃ | —CF₂CF₃ | N | C | N | Z |
| 503 | —Cl | —NH₂ | —CH₃ | —CH₂CF₃ | N | C | N | X |
| 504 | —Cl | —NH₂ | —CH₃ | —CH₂CF₃ | N | C | N | Z |

TABLE 1-continued

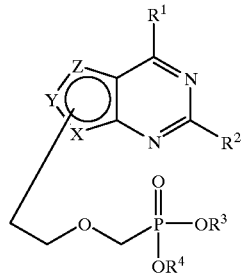

| Comp. No. | R¹ | R² | R³ | R⁴ | X | Y | Z | P.S. |
|---|---|---|---|---|---|---|---|---|
| 505 | —Cl | —NH₂ | —CF₂CF₃ | —CF₂CF₃ | N | C | N | X |
| 506 | —Cl | —NH₂ | —CF₂CF₃ | —CF₂CF₃ | N | C | N | Z |
| 507 | —Cl | —NH₂ | —CF₂CF₃ | —CH₂CF₃ | N | C | N | X |
| 508 | —Cl | —NH₂ | —CF₂CF₃ | —CH₂CF₃ | N | C | N | Z |
| 509 | —Cl | —NH₂ | —CH₂CF₃ | —CH₂CF₃ | N | C | N | X |
| 510 | —Cl | —NH₂ | —CH₂CF₃ | —CH₂CF₃ | N | C | N | Z |
| 511 | —Cl | —NH₂ | —CH₂CH₂OCH₃ | —CH₂CF₃ | N | C | N | X |
| 512 | —Cl | —NH₂ | —CH₂CH₂OCH₃ | —CH₂CF₃ | N | C | N | Z |
| 513 | —Cl | —NH₂ | —CH₂CH₂OCH₃ | —CH₂CH₂OCH₃ | N | C | N | X |
| 514 | —Cl | —NH₂ | —CH₂CH₂OCH₃ | —CH₂CH₂OCH₃ | N | C | N | Z |
| 515 | —Cl | —NH₂ | —CH₂CH₂OC₂H₅ | —CH₂CH₂OC₂H₅ | N | C | N | X |
| 516 | —Cl | —NH₂ | —CH₂CH₂OC₂H₅ | —CH₂CH₂OC₂H₅ | N | C | N | z |
| 517 | —Cl | —NH₂ | —CH₂CH₂OC₃H₇ | —CH₂CH₂OC₃H₇ | N | C | N | X |
| 518 | —Cl | —NH₂ | —CH₂CH₂OC₃H₇ | —CH₂CH₂OC₃H₇ | N | C | N | Z |
| 519 | —Cl | —NH₂ | —CH₂CH₂OC₆H₅ | —CH₂CF₃ | N | C | N | X |
| 520 | —Cl | —NH₂ | —CH₂CH₂OC₆H₅ | —CH₂CF₃ | N | C | N | Z |
| 521 | —Cl | —NH₂ | —CH₂CH₂OC₆H₅ | —CH₂CH₂OCH₃ | N | C | N | X |
| 522 | —Cl | —NH₂ | —CH₂CH₂OC₆H₅ | —CH₂CH₂OCH₃ | N | C | N | Z |
| 523 | —Cl | —NH₂ | —CH₂CH₂OC₆H₅ | —CH₂CH₂OC₆H₅ | N | C | N | X |
| 524 | —Cl | —NH₂ | —CH₂CH₂OC₆H₅ | —CH₂CH₂OC₆H₅ | N | C | N | Z |
| 525 | —Cl | —NH₂ | —CH₂CH₂OCH₂C₆H₅ | —CH₂CF₃ | N | C | N | X |
| 526 | —Cl | —NH₂ | —CH₂CH₂OCH₂C₆H₅ | —CH₂CF₃ | N | C | N | Z |
| 527 | —Cl | —NH₂ | —CH₂CH₂OCH₂C₆H₅ | —CH₂CH₂OCH₃ | N | C | N | X |
| 528 | —Cl | —NH₂ | —CH₂CH₂OCH₂C₆H₅ | —CH₂CH₂OCH₃ | N | C | N | Z |
| 529 | —Cl | —NH₂ | —CH₂CH₂OCH₂C₆H₅ | —CH₂CH₂OC₆H₅ | N | C | N | X |
| 530 | —Cl | —NH₂ | —CH₂CH₂OCH₂C₆H₅ | —CH₂CH₂OC₆H₅ | N | C | N | Z |
| 531 | —Cl | —NH₂ | —CH₂CH₂OCH₂C₆H₅ | —CH₂CH₂OCH₂C₆H₅ | N | C | N | X |
| 532 | —Cl | —NH₂ | —CH₂CH₂OCH₂C₆H₅ | —CH₂CH₂OCH₂C₆H₅ | N | C | N | Z |
| 583 | —Cl | —NH₂ | —CH₂CH₂OC₂H₄C₆H₅ | —CH₂CH₂OC₂H₄C₆H₅ | N | C | N | X |
| 534 | —Cl | —NH₂ | —CH₂CH₂OC₂H₄C₆H₅ | —CH₂CH₂OC₂H₄C₆H₅ | N | C | N | Z |
| 535 | —Cl | —NH₂ | —CH₂CH₂OC(O)CH₃ | —CH₂CF₃ | N | C | N | X |
| 536 | —Cl | —NH₂ | —CH₂CH₂OC(O)CH₃ | —CH₂CF₃ | N | C | N | Z |
| 537 | —Cl | —NH₂ | —CH₂CH₂OC(O)CH₃ | —CH₂CH₂OCH₃ | N | C | N | X |
| 538 | —Cl | —NH₂ | —CH₂CH₂OC(O)CH₃ | —CH₂CH₂OCH₃ | N | C | N | Z |
| 539 | —Cl | —NH₂ | —CH₂CH₂OC(O)CH₃ | —CH₂CH₂OC₆H₅ | N | C | N | X |
| 540 | —Cl | —NH₂ | —CH₂CH₂OC(O)CH₃ | —CH₂CH₂OC₆H₅ | N | C | N | Z |
| 541 | —Cl | —NH₂ | —CH₂CH₂OC(O)CH₃ | —CH₂CH₂OCH₂C₆H₅ | N | C | N | X |
| 542 | —Cl | —NH₂ | —CH₂CH₂OC(O)CH₃ | —CH₂CH₂OCH₂C₆H₅ | N | C | N | Z |
| 543 | —Cl | —NH₂ | —CH₂CH₂OC(O)CH₃ | —CH₂CH₂OC(O)CH₃ | N | C | N | X |
| 544 | —Cl | —NH₂ | —CH₂CH₂OC(O)CH₃ | —CH₂CH₂OC(O)CH₃ | N | C | N | Z |
| 545 | —Cl | —NH₂ | —CH₂CH₂OC(O)C₂H₅ | —CH₂CH₂OC(O)C₂H₅ | N | C | N | X |
| 546 | —Cl | —NH₂ | —CH₂CH₂OC(O)C₂H₅ | —CH₂CH₂OC(O)C₂H₅ | N | C | N | Z |
| 547 | —Cl | —NH₂ | —CH₂CH₂OC(O)C₃H₇ | —CH₂CH₂OC(O)C₃H₇ | N | C | N | X |
| 548 | —Cl | —NH₂ | —CH₂CH₂OC(O)C₃H₇ | —CH₂CH₂OC(O)C₃H₇ | N | C | N | Z |
| 549 | —Cl | —NH₂ | —CH₂CH₂OC(O)C₄H₉ | —CH₂CH₂OC(O)C₄H₉ | N | C | N | X |
| 550 | —Cl | —NH₂ | —CH₂CH₂OC(O)C₄H₉ | —CH₂CH₂OC(O)C₄H₉ | N | C | N | Z |
| 551 | —Cl | —Cl | —CH₃ | —CF₂CF₃ | N | C | N | X |
| 552 | —Cl | —Cl | —CH₃ | —CF₂CF₃ | N | C | N | Z |
| 553 | —Cl | —Cl | —CH₃ | —CH₂CF₃ | N | C | N | X |
| 554 | —Cl | —Cl | —CH₃ | —CH₂CF₃ | N | C | N | Z |
| 555 | —Cl | —Cl | —CF₂CF₃ | —CF₂CF₃ | N | C | N | X |
| 556 | —Cl | —Cl | —CF₂CF₃ | —CF₂CF₃ | N | C | N | Z |
| 557 | —Cl | —Cl | —CF₂CF₃ | —CH₂CF₃ | N | C | N | X |
| 558 | —Cl | —Cl | —CF₂CF₃ | —CH₂CF₃ | N | C | N | Z |
| 559 | —Cl | —Cl | —CH₂CF₃ | —CH₂CF₃ | N | C | N | X |
| 560 | —Cl | —Cl | —CH₂CF₃ | —CH₂CF₃ | N | C | N | Z |
| 561 | —Cl | —Cl | —CH₂CH₂OCH₃ | —CH₂CF₃ | N | C | N | X |
| 562 | —Cl | —Cl | —CH₂CH₂OCH₃ | —CH₂CF₃ | N | C | N | Z |
| 563 | —Cl | —Cl | —CH₂CH₂OCH₃ | —CH₂CH₂OCH₃ | N | C | N | X |
| 564 | —Cl | —Cl | —CH₂CH₂OCH₃ | —CH₂CH₂OCH₃ | N | C | N | Z |
| 565 | —Cl | —Cl | —CH₂CH₂OC₂H₅ | —CH₂CH₂OC₂H₅ | N | C | N | X |

TABLE 1-continued

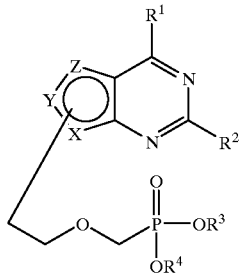

| Comp. No. | R¹ | R² | R³ | R⁴ | X | Y | Z | P.S. |
|---|---|---|---|---|---|---|---|---|
| 566 | —Cl | —Cl | —CH₂CH₂OC₂H₅ | —CH₂CH₂OC₂H₅ | N | C | N | Z |
| 567 | —Cl | —Cl | —CH₂CH₂OC₃H₇ | —CH₂CH₂OC₃H₇ | N | C | N | X |
| 568 | —Cl | —Cl | —CH₂CH₂OC₃H₇ | —CH₂CH₂OC₃H₇ | N | C | N | Z |
| 569 | —Cl | —Cl | —CH₂CH₂OC₆H₅ | —CH₂CF₃ | N | C | N | X |
| 570 | —Cl | —Cl | —CH₂CH₂OC₆H₅ | —CH₂CF₃ | N | C | N | Z |
| 571 | —Cl | —Cl | —CH₂CH₂OC₆H₅ | —CH₂CH₂OCH₃ | N | C | N | X |
| 572 | —Cl | —Cl | —CH₂CH₂OC₆H₅ | —CH₂CH₂OCH₃ | N | C | N | Z |
| 573 | —Cl | —Cl | —CH₂CH₂OC₆H₅ | —CH₂CH₂OC₆H₅ | N | C | N | X |
| 574 | —Cl | —Cl | —CH₂CH₂OC₆H₅ | —CH₂CH₂OC₆H₅ | N | C | N | Z |
| 575 | —Cl | —Cl | —CH₂CH₂OCH₂C₆H₅ | —CH₂CF₃ | N | C | N | X |
| 576 | —Cl | —Cl | —CH₂CH₂OCH₂C₆H₅ | —CH₂CF₃ | N | C | N | Z |
| 577 | —Cl | —Cl | —CH₂CH₂OCH₂C₆H₅ | —CH₂CH₂OCH₃ | N | C | N | X |
| 578 | —Cl | —Cl | —CH₂CH₂OCH₂C₆H₅ | —CH₂CH₂OCH₃ | N | C | N | Z |
| 579 | —Cl | —Cl | —CH₂CH₂OCH₂C₆H₅ | —CH₂CH₂OC₆H₅ | N | C | N | X |
| 580 | —Cl | —Cl | —CH₂CH₂OCH₂C₆H₅ | —CH₂CH₂OC₆H₅ | N | C | N | Z |
| 581 | —Cl | —Cl | —CH₂CH₂OCH₂C₆H₅ | —CH₂CH₂OCH₂C₆H₅ | N | C | N | X |
| 582 | —Cl | —Cl | —CH₂CH₂OCH₂C₆H₅ | —CH₂CH₂OCH₂C₆H₅ | N | C | N | Z |
| 583 | —Cl | —Cl | —CH₂CH₂OC₂H₄C₆H₅ | —CH₂CH₂OC₂H₄C₆H₅ | N | C | N | X |
| 584 | —Cl | —Cl | —CH₂CH₂OC₂H₄C₆H₅ | —CH₂CH₂OC₂H₄C₆H₅ | N | C | N | Z |
| 585 | —Cl | —Cl | —CH₂CH₂OC(O)CH₃ | —CH₂CF₃ | N | C | N | X |
| 586 | —Cl | —Cl | —CH₂CH₂OC(O)CH₃ | —CH₂CF₃ | N | C | N | Z |
| 587 | —Cl | —Cl | —CH₂CH₂OC(O)CH₃ | —CH₂CH₂OCH₃ | N | C | N | X |
| 588 | —Cl | —Cl | —CH₂CH₂OC(O)CH₃ | —CH₂CH₂OCH₃ | N | C | N | Z |
| 589 | —Cl | —Cl | —CH₂CH₂OC(O)CH₃ | —CH₂CH₂OC₆H₅ | N | C | N | X |
| 590 | —Cl | —Cl | —CH₂CH₂OC(O)CH₃ | —CH₂CH₂OC₆H₅ | N | C | N | Z |
| 591 | —Cl | —Cl | —CH₂CH₂OC(O)CH₃ | —CH₂CH₂OCH₂C₆H₅ | N | C | N | X |
| 592 | —Cl | —Cl | —CH₂CH₂OC(O)CH₃ | —CH₂CH₂OCH₂C₆H₅ | N | C | N | Z |
| 593 | —Cl | —Cl | —CH₂CH₂OC(O)CH₃ | —CH₂CH₂OC(O)CH₃ | N | C | N | X |
| 594 | —Cl | —Cl | —CH₂CH₂OC(O)CH₃ | —CH₂CH₂OC(O)CH₃ | N | C | N | Z |
| 595 | —Cl | —Cl | —CH₂CH₂OC(O)C₂H₅ | —CH₂CH₂OC(O)C₂H₅ | N | C | N | X |
| 596 | —Cl | —Cl | —CH₂CH₂OC(O)C₂H₅ | —CH₂CH₂OC(O)C₂H₅ | N | C | N | Z |
| 597 | —Cl | —Cl | —CH₂CH₂OC(O)C₃H₇ | —CH₂CH₂OC(O)C₃H₇ | N | C | N | X |
| 598 | —Cl | —Cl | —CH₂CH₂OC(O)C₃H₇ | —CH₂CH₂OC(O)C₃H₇ | N | C | N | Z |
| 599 | —Cl | —Cl | —CH₂CH₂OC(O)C₄H₉ | —CH₂CH₂OC(O)C₄H₉ | N | C | N | X |
| 600 | —Cl | —Cl | —CH₂CH₂OC(O)C₄H₉ | —CH₂CH₂OC(O)C₄H₉ | N | C | N | Z |
| 601 | —SH | —NH₂ | —CH₃ | —CF₂CF₃ | N | C | N | X |
| 602 | —SH | —NH₂ | —CH₃ | —CF₂CF₃ | N | C | N | Z |
| 603 | —SH | —NH₂ | —CH₃ | —CH₂CF₃ | N | C | N | X |
| 604 | —SH | —NH₂ | —CH₃ | —CH₂CF₃ | N | C | N | Z |
| 605 | —SH | —NH₂ | —CF₂CF₃ | —CF₂CF₃ | N | C | N | X |
| 606 | —SH | —NH₂ | —CF₂CF₃ | —CF₂CF₃ | N | C | N | Z |
| 607 | —SH | —NH₂ | —CF₂CF₃ | —CH₂CF₃ | N | C | N | X |
| 608 | —SH | —NH₂ | —CF₂CF₃ | —CH₂CF₃ | N | C | N | Z |
| 609 | —SH | —NH₂ | —CH₂CF₃ | —CH₂CF₃ | N | C | N | X |
| 610 | —SH | —NH₂ | —CH₂CF₃ | —CH₂CF₃ | N | C | N | Z |
| 611 | —SH | —NH₂ | —CH₂CH₂OCH₃ | —CH₂CF₃ | N | C | N | X |
| 612 | —SH | —NH₂ | —CH₂CH₂OCH₃ | —CH₂CF₃ | N | C | N | Z |
| 613 | —SH | —NH₂ | —CH₂CH₂OCH₃ | —CH₂CH₂OCH₃ | N | C | N | X |
| 614 | —SH | —NH₂ | —CH₂CH₂OCH₃ | —CH₂CH₂OCH₃ | N | C | N | Z |
| 615 | —SH | —NH₂ | —CH₂CH₂OC₂H₅ | —CH₂CH₂OC₂H₅ | N | C | N | X |
| 616 | —SH | —NH₂ | —CH₂CH₂OC₂H₅ | —CH₂CH₂OC₂H₅ | N | C | N | Z |
| 617 | —SH | —NH₂ | —CH₂CH₂OC₃H₇ | —CH₂CH₂OC₃H₇ | N | C | N | X |
| 618 | —SH | —NH₂ | —CH₂CH₂OC₃H₇ | —CH₂CH₂OC₃H₇ | N | C | N | Z |
| 619 | —SH | —NH₂ | —CH₂CH₂OC₆H₅ | —CH₂CF₃ | N | C | N | X |
| 620 | —SH | —NH₂ | —CH₂CH₂OC₆H₅ | —CH₂CF₃ | N | C | N | Z |
| 621 | —SH | —NH₂ | —CH₂CH₂OC₆H₅ | —CH₂CH₂OCH₃ | N | C | N | X |
| 622 | —SH | —NH₂ | —CH₂CH₂OC₆H₅ | —CH₂CH₂OCH₃ | N | C | N | Z |
| 623 | —SH | —NH₂ | —CH₂CH₂OC₆H₅ | —CH₂CH₂OC₆H₅ | N | C | N | X |
| 624 | —SH | —NH₂ | —CH₂CH₂OC₆H₅ | —CH₂CH₂OC₆H₅ | N | C | N | Z |
| 625 | —SH | —NH₂ | —CH₂CH₂OCH₂C₆H₅ | —CH₂CF₃ | N | C | N | X |
| 626 | —SH | —NH₂ | —CH₂CH₂OCH₂C₆H₅ | —CH₂CF₃ | N | C | N | Z |

TABLE 1-continued

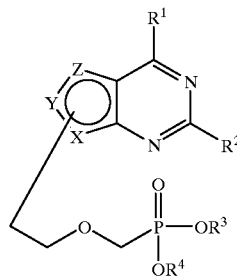

| Comp. No. | R¹ | R² | R³ | R⁴ | X | Y | Z | P.S. |
|---|---|---|---|---|---|---|---|---|
| 627 | —SH | —NH$_2$ | —CH$_2$CH$_2$OCH$_2$C$_6$H$_5$ | —CH$_2$CH$_2$OCH$_3$ | N | C | N | X |
| 628 | —SH | —NH$_2$ | —CH$_2$CH$_2$OCH$_2$C$_6$H$_5$ | —CH$_2$CH$_2$OCH$_3$ | N | C | N | Z |
| 629 | —SH | —NH$_2$ | —CH$_2$CH$_2$OCH$_2$C$_6$H$_5$ | —CH$_2$CH$_2$OC$_6$H$_5$ | N | C | N | X |
| 630 | —SH | —NH$_2$ | —CH$_2$CH$_2$OCH$_2$C$_6$H$_5$ | —CH$_2$CH$_2$OC$_6$H$_5$ | N | C | N | Z |
| 631 | —SH | —NH$_2$ | —CH$_2$CH$_2$OCH$_2$C$_6$H$_5$ | —CH$_2$CH$_2$OCH$_2$C$_6$H$_5$ | N | C | N | X |
| 632 | —SH | —NH$_2$ | —CH$_2$CH$_2$OCH$_2$C$_6$H$_5$ | —CH$_2$CH$_2$OCH$_2$C$_6$H$_5$ | N | C | N | Z |
| 633 | —SH | —NH$_2$ | —CH$_2$CH$_2$OC$_2$H$_4$C$_6$H$_5$ | —CH$_2$CH$_2$OC$_2$H$_4$C$_6$H$_5$ | N | C | N | X |
| 634 | —SH | —NH$_2$ | —CH$_2$CH$_2$OC$_2$H$_4$C$_6$H$_5$ | —CH$_2$CH$_2$OC$_2$H$_4$C$_6$H$_5$ | N | C | N | Z |
| 635 | —SH | —NH$_2$ | —CH$_2$CH$_2$OC(O)CH$_3$ | —CH$_2$CF$_3$ | N | C | N | X |
| 636 | —SH | —NH$_2$ | —CH$_2$CH$_2$OC(O)CH$_3$ | —CH$_2$CF$_3$ | N | C | N | Z |
| 637 | —SH | —NH$_2$ | —CH$_2$CH$_2$OC(O)CH$_3$ | —CH$_2$CH$_2$OCH$_3$ | N | C | N | X |
| 638 | —SH | —NH$_2$ | —CH$_2$CH$_2$OC(O)CH$_3$ | —CH$_2$CH$_2$OCH$_3$ | N | C | N | Z |
| 639 | —SH | —NH$_2$ | —CH$_2$CH$_2$OC(O)CH$_3$ | —CH$_2$CH$_2$OC$_6$H$_5$ | N | C | N | X |
| 640 | —SH | —NH$_2$ | —CH$_2$CH$_2$OC(O)CH$_3$ | —CH$_2$CH$_2$OC$_6$H$_5$ | N | C | N | Z |
| 641 | —SH | —NH$_2$ | —CH$_2$CH$_2$OC(O)CH$_3$ | —CH$_2$CH$_2$OCH$_2$C$_6$H$_5$ | N | C | N | X |
| 642 | —SH | —NH$_2$ | —CH$_2$CH$_2$OC(O)CH$_3$ | —CH$_2$CH$_2$OCH$_2$C$_6$H$_5$ | N | C | N | Z |
| 643 | —SH | —NH$_2$ | —CH$_2$CH$_2$OC(O)CH$_3$ | —CH$_2$CH$_2$OC(O)CH$_3$ | N | C | N | X |
| 644 | —SH | —NH$_2$ | —CH$_2$CH$_2$OC(O)CH$_3$ | —CH$_2$CH$_2$OC(O)CH$_3$ | N | C | N | Z |
| 645 | —SH | —NH$_2$ | —CH$_2$CH$_2$OC(O)C$_2$H$_5$ | —CH$_2$CH$_2$OC(O)C$_2$H$_5$ | N | C | N | X |
| 646 | —SH | —NH$_2$ | —CH$_2$CH$_2$OC(O)C$_2$H$_5$ | —CH$_2$CH$_2$OC(O)C$_2$H$_5$ | N | C | N | Z |
| 647 | —SH | —NH$_2$ | —CH$_2$CH$_2$OC(O)C$_3$H$_7$ | —CH$_2$CH$_2$OC(O)C$_3$H$_7$ | N | C | N | X |
| 648 | —SH | —NH$_2$ | —CH$_2$CH$_2$OC(O)C$_3$H$_7$ | —CH$_2$CH$_2$OC(O)C$_3$H$_7$ | N | C | N | Z |
| 649 | —SH | —NH$_2$ | —CH$_2$CH$_2$OC(O)C$_4$H$_9$ | —CH$_2$CH$_2$OC(O)C$_4$H$_9$ | N | C | N | X |
| 650 | —SH | —NH$_2$ | —CH$_2$CH$_2$OC(O)C$_4$H$_9$ | —CH$_2$CH$_2$OC(O)C$_4$H$_9$ | N | C | N | Z |
| 651 | —NH$_2$ | —NH$_2$ | —CH$_3$ | —CF$_2$CF$_3$ | N | N | N | X |
| 652 | —NH$_2$ | —NH$_2$ | —CH$_3$ | —CF$_2$CF$_3$ | N | N | N | Y |
| 653 | —NH$_2$ | —NH$_2$ | —CH$_3$ | —CF$_2$CF$_3$ | N | N | N | Z |
| 654 | —NH$_2$ | —NH$_2$ | —CH$_3$ | —CH$_2$CF$_3$ | N | N | N | X |
| 655 | —NH$_2$ | —NH$_2$ | —CH$_3$ | —CH$_2$CF$_3$ | N | N | N | Y |
| 656 | —NH$_2$ | —NH$_2$ | —CH$_3$ | —CH$_2$CF$_3$ | N | N | N | Z |
| 657 | —NH$_2$ | —NH$_2$ | —CF$_2$CF$_3$ | —CF$_2$CF$_3$ | N | N | N | X |
| 658 | —NH$_2$ | —NH$_2$ | —CF$_2$CF$_3$ | —CF$_2$CF$_3$ | N | N | N | Y |
| 659 | —NH$_2$ | —NH$_2$ | —CF$_2$CF$_3$ | —CF$_2$CF$_3$ | N | N | N | Z |
| 660 | —NH$_2$ | —NH$_2$ | —CF$_2$CF$_3$ | —CH$_2$CF$_3$ | N | N | N | X |
| 661 | —NH$_2$ | —NH$_2$ | —CF$_2$CF$_3$ | —CH$_2$CF$_3$ | N | N | N | Y |
| 662 | —NH$_2$ | —NH$_2$ | —CF$_2$CF$_3$ | —CH$_2$CF$_3$ | N | N | N | Z |
| 663 | —NH$_2$ | —NH$_2$ | —CH$_2$CF$_3$ | —CH$_2$CF$_3$ | N | N | N | X |
| 664 | —NH$_2$ | —NH$_2$ | —CH$_2$CF$_3$ | —CH$_2$CF$_3$ | N | N | N | Y |
| 665 | —NH$_2$ | —NH$_2$ | —CH$_2$CF$_3$ | —CH$_2$CF$_3$ | N | N | N | Z |
| 666 | —NH$_2$ | —NH$_2$ | —CH$_2$CH$_2$OCH$_3$ | —CH$_2$CF$_3$ | N | N | N | X |
| 667 | —NH$_2$ | —NH$_2$ | —CH$_2$CH$_2$OCH$_3$ | —CH$_2$CF$_3$ | N | N | N | Y |
| 668 | —NH$_2$ | —NH$_2$ | —CH$_2$CH$_2$OCH$_3$ | —CH$_2$CF$_3$ | N | N | N | Z |
| 669 | —NH$_2$ | —NH$_2$ | —CH$_2$CH$_2$OCH$_3$ | —CH$_2$CH$_2$OCH$_3$ | N | N | N | X |
| 670 | —NH$_2$ | —NH$_2$ | —CH$_2$CH$_2$OCH$_3$ | —CH$_2$CH$_2$OCH$_3$ | N | N | N | Y |
| 671 | —NH$_2$ | —NH$_2$ | —CH$_2$CH$_2$OCH$_3$ | —CH$_2$CH$_2$OCH$_3$ | N | N | N | Z |
| 672 | —NH$_2$ | —NH$_2$ | —CH$_2$CH$_2$OC$_2$H$_5$ | —CH$_2$CH$_2$OC$_2$H$_5$ | N | N | N | X |
| 673 | —NH$_2$ | —NH$_2$ | —CH$_2$CH$_2$OC$_2$H$_5$ | —CH$_2$CH$_2$OC$_2$H$_5$ | N | N | N | Y |
| 674 | —NH$_2$ | —NH$_2$ | —CH$_2$CH$_2$OC$_2$H$_5$ | —CH$_2$CH$_2$OC$_2$H$_5$ | N | N | N | Z |
| 675 | —NH$_2$ | —NH$_2$ | —CH$_2$CH$_2$OC$_3$H$_7$ | —CH$_2$CH$_2$OC$_3$H$_7$ | N | N | N | X |
| 676 | —NH$_2$ | —NH$_2$ | —CH$_2$CH$_2$OC$_3$H$_7$ | —CH$_2$CH$_2$OC$_3$H$_7$ | N | N | N | Y |
| 677 | —NH$_2$ | —NH$_2$ | —CH$_2$CH$_2$OC$_3$H$_7$ | —CH$_2$CH$_2$OC$_3$H$_7$ | N | N | N | Z |
| 678 | —NH$_2$ | —NH$_2$ | —CH$_2$CH$_2$OC$_6$H$_5$ | —CH$_2$CF$_3$ | N | N | N | X |
| 679 | —NH$_2$ | —NH$_2$ | —CH$_2$CH$_2$OC$_6$H$_5$ | —CH$_2$CF$_3$ | N | N | N | Y |
| 680 | —NH$_2$ | —NH$_2$ | —CH$_2$CH$_2$OC$_6$H$_5$ | —CH$_2$CF$_3$ | N | N | N | Z |
| 681 | —NH$_2$ | —NH$_2$ | —CH$_2$CH$_2$OC$_6$H$_5$ | —CH$_2$CH$_2$OCH$_3$ | N | N | N | X |
| 682 | —NH$_2$ | —NH$_2$ | —CH$_2$CH$_2$OC$_6$H$_5$ | —CH$_2$CH$_2$OCH$_3$ | N | N | N | Y |
| 683 | —NH$_2$ | —NH$_2$ | —CH$_2$CH$_2$OC$_6$H$_5$ | —CH$_2$CH$_2$OCH$_3$ | N | N | N | Z |
| 684 | —NH$_2$ | —NH$_2$ | —CH$_2$CH$_2$OC$_6$H$_5$ | —CH$_2$CH$_2$OC$_6$H$_5$ | N | N | N | X |
| 685 | —NH$_2$ | —NH$_2$ | —CH$_2$CH$_2$OC$_6$H$_5$ | —CH$_2$CH$_2$OC$_6$H$_5$ | N | N | N | Y |
| 686 | —NH$_2$ | —NH$_2$ | —CH$_2$CH$_2$OC$_6$H$_5$ | —CH$_2$CH$_2$OC$_6$H$_5$ | N | N | N | Z |
| 687 | —NH$_2$ | —NH$_2$ | —CH$_2$CH$_2$OCH$_2$C$_6$H$_5$ | —CH$_2$CF$_3$ | N | N | N | X |

TABLE 1-continued

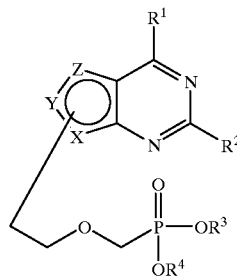

| Comp. No. | R¹ | R² | R³ | R⁴ | X | Y | Z | P.S. |
|---|---|---|---|---|---|---|---|---|
| 688 | —NH₂ | —NH₂ | —CH₂CH₂OCH₂C₆H₅ | —CH₂CF₃ | N | N | N | Y |
| 689 | —NH₂ | —NH₂ | —CH₂CH₂OCH₂C₆H₅ | —CH₂CF₃ | N | N | N | Z |
| 690 | —NH₂ | —NH₂ | —CH₂CH₂OCH₂C₆H₅ | —CH₂CH₂OCH₃ | N | N | N | X |
| 691 | —NH₂ | —NH₂ | —CH₂CH₂OCH₂C₆H₅ | —CH₂CH₂OCH₃ | N | N | N | Y |
| 692 | —NH₂ | —NH₂ | —CH₂CH₂OCH₂C₆H₅ | —CH₂CH₂OCH₃ | N | N | N | Z |
| 693 | —NH₂ | —NH₂ | —CH₂CH₂OCH₂C₆H₅ | —CH₂CH₂OC₆H₅ | N | N | N | X |
| 694 | —NH₂ | —NH₂ | —CH₂CH₂OCH₂C₆H₅ | —CH₂CH₂OC₆H₅ | N | N | N | Y |
| 695 | —NH₂ | —NH₂ | —CH₂CH₂OCH₂C₆H₅ | —CH₂CH₂OC₆H₅ | N | N | N | Z |
| 696 | —NH₂ | —NH₂ | —CH₂CH₂OCH₂C₆H₅ | —CH₂CH₂OCH₂C₆H₅ | N | N | N | X |
| 697 | —NH₂ | —NH₂ | —CH₂CH₂OCH₂C₆H₅ | —CH₂CH₂OCH₂C₆H₅ | N | N | N | Y |
| 698 | —NH₂ | —NH₂ | —CH₂CH₂OCH₂C₆H₅ | —CH₂CH₂OCH₂C₆H₅ | N | N | N | Z |
| 699 | —NH₂ | —NH₂ | —CH₂CH₂OC₂H₄C₆H₅ | —CH₂CH₂OC₂H₄C₆H₅ | N | N | N | X |
| 700 | —NH₂ | —NH₂ | —CH₂CH₂OC₂H₄C₆H₅ | —CH₂CH₂OC₂H₄C₆H₅ | N | N | N | Y |
| 701 | —NH₂ | —NH₂ | —CH₂CH₂OC₂H₄C₆H₅ | —CH₂CH₂OC₂H₄C₆H₅ | N | N | N | Z |
| 702 | —NH₂ | —NH₂ | —CH₂CH₂OC(O)CH₃ | —CH₂CF₃ | N | N | N | X |
| 703 | —NH₂ | —NH₂ | —CH₂CH₂OC(O)CH₃ | —CH₂CF₃ | N | N | N | Y |
| 704 | —NH₂ | —NH₂ | —CH₂CH₂OC(O)CH₃ | —CH₂CF₃ | N | N | N | Z |
| 705 | —NH₂ | —NH₂ | —CH₂CH₂OC(O)CH₃ | —CH₂CH₂OCH₃ | N | N | N | X |
| 706 | —NH₂ | —NH₂ | —CH₂CH₂OC(O)CH₃ | —CH₂CH₂OCH₃ | N | N | N | Y |
| 707 | —NH₂ | —NH₂ | —CH₂CH₂OC(O)CH₃ | —CH₂CH₂OCH₃ | N | N | N | Z |
| 708 | —NH₂ | —NH₂ | —CH₂CH₂OC(O)CH₃ | —CH₂CH₂OC₆H₅ | N | N | N | X |
| 709 | —NH₂ | —NH₂ | —CH₂CH₂OC(O)CH₃ | —CH₂CH₂OC₆H₅ | N | N | N | Y |
| 710 | —NH₂ | —NH₂ | —CH₂CH₂OC(O)CH₃ | —CH₂CH₂OC₆H₅ | N | N | N | Z |
| 711 | —NH₂ | —NH₂ | —CH₂CH₂OC(O)CH₃ | —CH₂CH₂OCH₂C₆H₅ | N | N | N | X |
| 712 | —NH₂ | —NH₂ | —CH₂CH₂OC(O)CH₃ | —CH₂CH₂OCH₂C₆H₅ | N | N | N | Y |
| 713 | —NH₂ | —NH₂ | —CH₂CH₂OC(O)CH₃ | —CH₂CH₂OCH₂C₆H₅ | N | N | N | |
| 714 | —NH₂ | —NH₂ | —CH₂CH₂OC(O)CH₃ | —CH₂CH₂OC(O)CH₃ | N | N | N | X |
| 715 | —NH₂ | —NH₂ | —CH₂CH₂OC(O)CH₃ | —CH₂CH₂OC(O)CH₃ | N | N | N | Y |
| 716 | —NH₂ | —NH₂ | —CH₂CH₂OC(O)CH₃ | —CH₂CH₂OC(O)CH₃ | N | N | N | Z |
| 717 | —NH₂ | —NH₂ | —CH₂CH₂OC(O)C₂H₅ | —CH₂CH₂OC(O)C₂H₅ | N | N | N | X |
| 718 | —NH₂ | —NH₂ | —CH₂CH₂OC(O)C₂H₅ | —CH₂CH₂OC(O)C₂H₅ | N | N | N | Y |
| 719 | —NH₂ | —NH₂ | —CH₂CH₂OC(O)C₂H₅ | —CH₂CH₂OC(O)C₂H₅ | N | N | N | Z |
| 720 | —NH₂ | —NH₂ | —CH₂CH₂OC(O)C₃H₇ | —CH₂CH₂OC(O)C₃H₇ | N | N | N | X |
| 721 | —NH₂ | —NH₂ | —CH₂CH₂OC(O)C₃H₇ | —CH₂CH₂OC(O)C₃H₇ | N | N | N | Y |
| 722 | —NH₂ | —NH₂ | —CH₂CH₂OC(O)C₃H₇ | —CH₂CH₂OC(O)C₃H₇ | N | N | N | Z |
| 723 | —NH₂ | —NH₂ | —CH₂CH₂OC(O)C₄H₉ | —CH₂CH₂OC(O)C₄H₉ | N | N | N | X |
| 724 | —NH₂ | —NH₂ | —CH₂CH₂OC(O)C₄H₉ | —CH₂CH₂OC(O)C₄H₉ | N | N | N | Y |
| 725 | —NH₂ | —NH₂ | —CH₂CH₂OC(O)C₄H₉ | —CH₂CH₂OC(O)C₄H₉ | N | N | N | Z |
| 726 | —NH₂ | —NH₂ | —CH₃ | —CF₂CF₃ | N | N | C | X |
| 727 | —NH₂ | —NH₂ | —CH₃ | —CF₂CF₃ | N | N | C | Y |
| 728 | —NH₂ | —NH₂ | —CH₃ | —CH₂CF₃ | N | N | C | X |
| 729 | —NH₂ | —NH₂ | —CH₃ | —CH₂CF₃ | N | N | C | Y |
| 730 | —NH₂ | —NH₂ | —CF₂CF₃ | —CF₂CF₃ | N | N | C | X |
| 731 | —NH₂ | —NH₂ | —CF₂CF₃ | —CF₂CF₃ | N | N | C | Y |
| 732 | —NH₂ | —NH₂ | —CF₂CF₃ | —CH₂CF₃ | N | N | C | X |
| 733 | —NH₂ | —NH₂ | —CF₂CF₃ | —CH₂CF₃ | N | N | C | Y |
| 734 | —NH₂ | —NH₂ | —CH₂CF₃ | —CH₂CF₃ | N | N | C | X |
| 735 | —NH₂ | —NH₂ | —CH₂CF₃ | —CH₂CF₃ | N | N | C | Y |
| 736 | —NH₂ | —NH₂ | —CH₂CH₂OCH₃ | —CH₂CF₃ | N | N | C | X |
| 737 | —NH₂ | —NH₂ | —CH₂CH₂OCH₃ | —CH₂CF₃ | N | N | C | Y |
| 738 | —NH₂ | —NH₂ | —CH₂CH₂OCH₃ | —CH₂CH₂OCH₃ | N | N | C | X |
| 739 | —NH₂ | —NH₂ | —CH₂CH₂OCH₃ | —CH₂CH₂OCH₃ | N | N | C | Y |
| 740 | —NH₂ | —NH₂ | —CH₂CH₂OC₂H₅ | —CH₂CH₂OC₂H₅ | N | N | C | X |
| 741 | —NH₂ | —NH₂ | —CH₂CH₂OC₂H₅ | —CH₂CH₂OC₂H₅ | N | N | C | Y |
| 742 | —NH₂ | —NH₂ | —CH₂CH₂OC₃H₇ | —CH₂CH₂OC₃H₇ | N | N | C | X |
| 743 | —NH₂ | —NH₂ | —CH₂CH₂OC₃H₇ | —CH₂CH₂OC₃H₇ | N | N | C | Y |
| 744 | —NH₂ | —NH₂ | —CH₂CH₂OC₆H₅ | —CH₂CF₃ | N | N | C | X |
| 745 | —NH₂ | —NH₂ | —CH₂CH₂OC₆H₅ | —CH₂CF₃ | N | N | C | Y |
| 746 | —NH₂ | —NH₂ | —CH₂CH₂OC₆H₅ | —CH₂CH₂OCH₃ | N | N | C | X |
| 747 | —NH₂ | —NH₂ | —CH₂CH₂OC₆H₅ | —CH₂CH₂OCH₃ | N | N | C | Y |
| 748 | —NH₂ | —NH₂ | —CH₂CH₂OC₆H₅ | —CH₂CH₂OC₆H₅ | N | N | C | X |

TABLE 1-continued

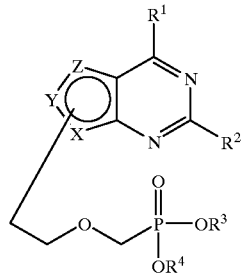

| Comp. No. | R¹ | R² | R³ | R⁴ | X | Y | Z | P.S. |
|---|---|---|---|---|---|---|---|---|
| 749 | —NH₂ | —NH₂ | —CH₂CH₂OC₆H₅ | —CH₂CH₂OC₆H₅ | N | N | C | Y |
| 750 | —NH₂ | —NH₂ | —CH₂CH₂OCH₂C₆H₅ | —CH₂CF₃ | N | N | C | X |
| 751 | —NH₂ | —NH₂ | —CH₂CH₂OCH₂C₆H₅ | —CH₂CF₃ | N | N | C | Y |
| 752 | —NH₂ | —NH₂ | —CH₂CH₂OCH₂C₆H₅ | —CH₂CH₂OCH₃ | N | N | C | X |
| 753 | —NH₂ | —NH₂ | —CH₂CH₂OCH₂C₆H₅ | —CH₂CH₂OCH₃ | N | N | C | Y |
| 754 | —NH₂ | —NH₂ | —CH₂CH₂OCH₂C₆H₅ | —CH₂CH₂OC₆H₅ | N | N | C | X |
| 755 | —NH₂ | —NH₂ | —CH₂CH₂OCH₂C₆H₅ | —CH₂CH₂OC₆H₅ | N | N | C | Y |
| 756 | —NH₂ | —NH₂ | —CH₂CH₂OCH₂C₆H₅ | —CH₂CH₂OCH₂C₆H₅ | N | N | C | X |
| 757 | —NH₂ | —NH₂ | —CH₂CH₂OCH₂C₆H₅ | —CH₂CH₂OCH₂C₆H₅ | N | N | C | Y |
| 758 | —NH₂ | —NH₂ | —CH₂CH₂OC₂H₄C₆H₅ | —CH₂CH₂OC₂H₄C₆H₅ | N | N | C | X |
| 759 | —NH₂ | —NH₂ | —CH₂CH₂OC₂H₄C₆H₅ | —CH₂CH₂OC₂H₄C₆H₅ | N | N | C | Y |
| 760 | —NH₂ | —NH₂ | —CH₂CH₂OC(O)CH₃ | —CH₂CF₃ | N | N | C | X |
| 761 | —NH₂ | —NH₂ | —CH₂CH₂OC(O)CH₃ | —CH₂CF₃ | N | N | C | Y |
| 762 | —NH₂ | —NH₂ | —CH₂CH₂OC(O)CH₃ | —CH₂CH₂OCH₃ | N | N | C | X |
| 763 | —NH₂ | —NH₂ | —CH₂CH₂OC(O)CH₃ | —CH₂CH₂OCH₃ | N | N | C | Y |
| 764 | —NH₂ | —NH₂ | —CH₂CH₂OC(O)CH₃ | —CH₂CH₂OC₆H₅ | N | N | C | x |
| 765 | —NH₂ | —NH₂ | —CH₂CH₂OC(O)CH₃ | —CH₂CH₂OC₆H₅ | N | N | C | Y |
| 766 | —NH₂ | —NH₂ | —CH₂CH₂OC(O)CH₃ | —CH₂CH₂OCH₂C₆H₅ | N | N | C | X |
| 767 | —NH₂ | —NH₂ | —CH₂CH₂OC(O)CH₃ | —CH₂CH₂OCH₂C₆H₅ | N | N | C | Y |
| 768 | —NH₂ | —NH₂ | —CH₂CH₂OC(O)CH₃ | —CH₂CH₂OC(O)CH₃ | N | N | C | X |
| 769 | —NH₂ | —NH₂ | —CH₂CH₂OC(O)CH₃ | —CH₂CH₂OC(O)CH₃ | N | N | C | Y |
| 770 | —NH₂ | —NH₂ | —CH₂CH₂OC(O)C₂H₅ | —CH₂CH₂OC(O)C₂H₅ | N | N | C | X |
| 771 | —NH₂ | —NH₂ | —CH₂CH₂OC(O)C₂H₅ | —CH₂CH₂OC(O)C₂H₅ | N | N | C | Y |
| 772 | —NH₂ | —NH₂ | —CH₂CH₂OC(O)C₃H₇ | —CH₂CH₂OC(O)C₃H₇ | N | N | C | X |
| 773 | —NH₂ | —NH₂ | —CH₂CH₂OC(O)C₃H₇ | —CH₂CH₂OC(O)C₃H₇ | N | N | C | Y |
| 774 | —NH₂ | —NH₂ | —CH₂CH₂OC(O)C₄H₉ | —CH₂CH₂OC(O)C₄H₉ | N | N | C | X |
| 775 | —NH₂ | —NH₂ | —CH₂CH₂OC(O)C₄H₉ | —CH₂CH₂OC(O)C₄H₉ | N | N | C | Y |

TABLE 2

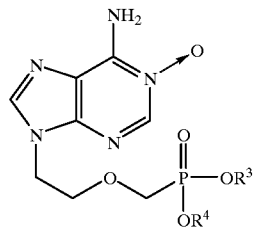

| Comp. No. | R² | R⁴ |
|---|---|---|
| 776 | —CH₃ | —CF₂CF₃ |
| 777 | —CH₃ | —CH₂CF₃ |
| 778 | —CF₂CF₃ | —CF₂CF₃ |
| 779 | —CF₂CF₃ | —CH₂CF₃ |
| 780 | —CH₂CF₃ | —CH₂CF₃ |
| 781 | —CH₂CH₂OCH₃ | —CH₂CF₃ |
| 782 | —CH₂CH₂OCH₃ | —CH₂CH₂OCH₃ |
| 783 | —CH₂CH₂OC₂H₅ | —CH₂CH₂OC₂H₅ |
| 784 | —CH₂CH₂OC₃H₇ | —CH₂CH₂OC₃H₇ |
| 785 | —CH₂CH₂OC₆H₅ | —CH₂CF₃ |
| 786 | —CH₂CH₂OC₆H₅ | —CH₂CH₂OCH₃ |
| 787 | —CH₂CH₂OC₆H₅ | —CH₂CH₂OC₆H₅ |
| 788 | —CH₂CH₂OCH₂C₆H₅ | —CH₂CF₃ |

TABLE 2-continued

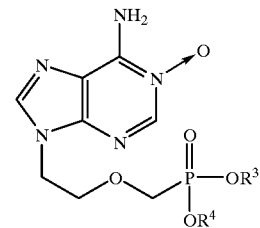

| Comp. No. | R² | R⁴ |
|---|---|---|
| 789 | —CH₂CH₂OCH₂C₆H₅ | —CH₂CH₂OCH₃ |
| 790 | —CH₂CH₂OCH₂C₆H₅ | —CH₂CH₂OC₆H₅ |
| 791 | —CH₂CH₂OCH₂C₆H₅ | —CH₂CH₂OCH₂C₆H₅ |
| 792 | —CH₂CH₂OC₂H₄C₆H₅ | —CH₂CH₂OC₂H₄C₆H₅ |
| 793 | —CH₂CH₂OC(O)CH₃ | —CH₂CF₃ |
| 794 | —CH₂CH₂OC(O)CH₃ | —CH₂CH₂OC₆H₅ |
| 795 | —CH₂CH₂OC(O)CH₃ | —CH₂CH₂OCH₂C₆H₅ |
| 796 | —CH₂CH₂OC(O)CH₃ | —CH₂CH₂OCH₂C₆H₅ |
| 797 | —CH₂CH₂OC(O)CH₃ | —CH₂CH₂OC(O)CH₃ |
| 798 | —CH₂CH₂OC(O)C₂H₅ | —CH₂CH₂OC(O)C₂H₅ |
| 799 | —CH₂CH₂OC(O)C₃H₇ | —CH₂CH₂OC(O)C₃H₇ |
| 800 | —CH₂CH₂OC(O)C₄H₉ | —CH₂CH₂OC(O)C₄H₉ |

TABLE 3

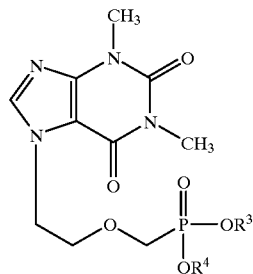

| Comp. No. | R² | R⁴ |
|---|---|---|
| 801 | —CH₃ | —CF₂CF₃ |
| 802 | —CH₃ | —CH₂CF₃ |
| 803 | —CF₂CF₃ | —CF₂CF₃ |
| 804 | —CF₂CF₃ | —CH₂CF₃ |
| 805 | —CH₂CF₃ | —CH₂CF₃ |
| 806 | —CH₂CH₂OCH₃ | —CH₂CF₃ |
| 807 | —CH₂CH₂OCH₃ | —CH₂CH₂OCH₃ |
| 808 | —CH₂CH₂OC₂H₅ | —CH₂CH₂OC₂H₅ |
| 809 | —CH₂CH₂OC₃H₇ | —CH₂CH₂OC₃H₇ |
| 810 | —CH₂CH₂OC₆H₅ | —CH₂CF₃ |
| 811 | —CH₂CH₂OC₆H₅ | —CH₂CH₂OCH₃ |
| 812 | —CH₂CH₂OC₆H₅ | —CH₂CH₂OC₆H₅ |

TABLE 3-continued

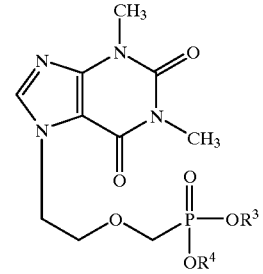

| Comp. No. | R² | R⁴ |
|---|---|---|
| 813 | —CH₂CH₂OCH₂C₆H₅ | —CH₂CF₃ |
| 814 | —CH₂CH₂OCH₂C₆H₅ | —CH₂CH₂OCH₃ |
| 815 | —CH₂CH₂OCH₂C₆H₅ | —CH₂CH₂C₆H₅ |
| 816 | —CH₂CH₂OCH₂C₆H₅ | —CH₂CH₂OCH₂C₆H₅ |
| 817 | —CH₂CH₂OC₂H₄C₆H₅ | —CH₂CH₂OC₂H₄C₆H₅ |
| 818 | —CH₂CH₂OC(O)CH₃ | —CH₂CF₃ |
| 819 | —CH₂CH₂OC(O)CH₃ | —CH₂CH₂OC₆H₅ |
| 820 | —CH₂CH₂OC(O)CH₃ | —CH₂CH₂OCH₂C₆H₅ |
| 821 | —CH₂CH₂OC(O)CH₃ | —CH₂CH₂OCH₂C₆H₅ |
| 822 | —CH₂CH₂OC(O)CH₃ | —CH₂CH₂OC(O)CH₃ |
| 823 | —CH₂CH₂OC(O)C₂H₅ | —CH₂CH₂OC(O)C₂H₅ |
| 824 | —CH₂CH₂OC(O)C₃H₇ | —CH₂CH₂OC(O)C₃H₇ |
| 825 | —CH₂CH₂OC(O)C₄H₉ | —CH₂CH₂OC(O)C₄H₉ |

TABLE 4

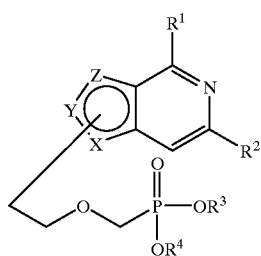

| Comp. No. | R¹ | R² | R³ | R⁴ | X | Y | Z | P.S. |
|---|---|---|---|---|---|---|---|---|
| 826 | —NH₂ | —NH₂ | —CH₃ | —CF₂CF₃ | N | N | N | X |
| 827 | —NH₂ | —NH₂ | —CH₃ | —CF₂CF₃ | N | N | N | Y |
| 828 | —NH₂ | —NH₂ | —CH₃ | —CF₂CF₃ | N | N | N | Z |
| 829 | —NH₂ | —NH₂ | —CH₃ | —CH₂CF₃ | N | N | N | X |
| 830 | —NH₂ | —NH₂ | —CH₃ | —CH₂CF₃ | N | N | N | Y |
| 831 | —NH₂ | —NH₂ | —CH₃ | —CH₂CF₃ | N | N | N | Z |
| 832 | —NH₂ | —NH₂ | —CF₂CF₃ | —CF₂CF₃ | N | N | N | X |
| 833 | —NH₂ | —NH₂ | —CF₂CF₃ | —CF₂CF₃ | N | N | N | Y |
| 834 | —NH₂ | —NH₂ | —CF₂CF₃ | —CF₂CF₃ | N | N | N | Z |
| 835 | —NH₂ | —NH₂ | —CF₂CF₃ | —CH₂CF₃ | N | N | N | X |
| 836 | —NH₂ | —NH₂ | —CF₂CF₃ | —CH₂CF₃ | N | N | N | Y |
| 837 | —NH₂ | —NH₂ | —CF₂CF₃ | —CH₂CF₃ | N | N | N | Z |
| 838 | —NH₂ | —NH₂ | —CH₂CF₃ | —CH₂CF₃ | N | N | N | X |
| 839 | —NH₂ | —NH₂ | —CH₂CF₃ | —CH₂CF₃ | N | N | N | Y |
| 840 | —NH₂ | —NH₂ | —CH₂CF₃ | —CH₂CF₃ | N | N | N | Z |
| 841 | —NH₂ | —NH₂ | —CH₂CH₂OCH₃ | —CH₂CF₃ | N | N | N | X |
| 842 | —NH₂ | —NH₂ | —CH₂CH₂OCH₃ | —CH₂CF₃ | N | N | N | Y |
| 843 | —NH₂ | —NH₂ | —CH₂CH₂OCH₃ | —CH₂CF₃ | N | N | N | Z |
| 844 | —NH₂ | —NH₂ | —CH₂CH₂OCH₃ | —CH₂CH₂OCH₃ | N | N | N | X |
| 845 | —NH₂ | —NH₂ | —CH₂CH₂OCH₃ | —CH₂CH₂OCH₃ | N | N | N | Y |
| 846 | —NH₂ | —NH₂ | —CH₂CH₂OCH₃ | —CH₂CH₂OCH₃ | N | N | N | Z |
| 847 | —NH₂ | —NH₂ | —CH₂CH₂OC₂H₅ | —CH₂CH₂OC₂H₅ | N | N | N | X |
| 848 | —NH₂ | —NH₂ | —CH₂CH₂OC₂H₅ | —CH₂CH₂OC₂H₅ | N | N | N | Y |

TABLE 4-continued

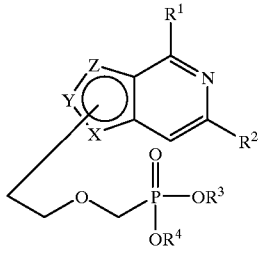

| Comp. No. | R¹ | R² | R³ | R⁴ | X | Y | Z | P.S. |
|---|---|---|---|---|---|---|---|---|
| 849 | —NH₂ | —NH₂ | —CH₂CH₂OC₂H₅ | —CH₂CH₂OC₂H₅ | N | N | N | Z |
| 850 | —NH₂ | —NH₂ | —CH₂CH₂OC₃H₇ | —CH₂CH₂OC₃H₇ | N | N | N | X |
| 851 | —NH₂ | —NH₂ | —CH₂CH₂OC₃H₇ | —CH₂CH₂OC₃H₇ | N | N | N | Y |
| 852 | —NH₂ | —NH₂ | —CH₂CH₂OC₃H₇ | —CH₂CH₂OC₃H₇ | N | N | N | Z |
| 853 | —NH₂ | —NH₂ | —CH₂CH₂OC₆H₅ | —CH₂CF₃ | N | N | N | X |
| 854 | —NH₂ | —NH₂ | —CH₂CH₂OC₆H₅ | —CH₂CF₃ | N | N | N | Y |
| 855 | —NH₂ | —NH₂ | —CH₂CH₂OC₆H₅ | —CH₂CF₃ | N | N | N | Z |
| 856 | —NH₂ | —NH₂ | —CH₂CH₂OC₆H₅ | —CH₂CH₂OCH₃ | N | N | N | X |
| 857 | —NH₂ | —NH₂ | —CH₂CH₂OC₆H₅ | —CH₂CH₂OCH₃ | N | N | N | Y |
| 858 | —NH₂ | —NH₂ | —CH₂CH₂OC₆H₅ | —CH₂CH₂OCH₃ | N | N | N | Z |
| 859 | —NH₂ | —NH₂ | —CH₂CH₂OC₆H₅ | —CH₂CH₂OC₆H₅ | N | N | N | X |
| 860 | —NH₂ | —NH₂ | —CH₂CH₂OC₆H₅ | —CH₂CH₂OC₆H₅ | N | N | N | Y |
| 861 | —NH₂ | —NH₂ | —CH₂CH₂OC₆H₅ | —CH₂CH₂OC₆H₅ | N | N | N | Z |
| 862 | —NH₂ | —NH₂ | —CH₂CH₂OCH₂C₆H₅ | —CH₂CF₃ | N | N | N | X |
| 863 | —NH₂ | —NH₂ | —CH₂CH₂OCH₂C₆H₅ | —CH₂CF₃ | N | N | N | Y |
| 864 | —NH₂ | —NH₂ | —CH₂CH₂OCH₂C₆H₅ | —CH₂CF₃ | N | N | N | Z |
| 865 | —NH₂ | —NH₂ | —CH₂CH₂OCH₂C₆H₅ | —CH₂CH₂OCH₃ | N | N | N | X |
| 866 | —NH₂ | —NH₂ | —CH₂CH₂OCH₂C₆H₅ | —CH₂CH₂OCH₃ | N | N | N | Y |
| 867 | —NH₂ | —NH₂ | —CH₂CH₂OCH₂C₆H₅ | —CH₂CH₂OCH₃ | N | N | N | Z |
| 868 | —NH₂ | —NH₂ | —CH₂CH₂OCH₂C₆H₅ | —CH₂CH₂OC₆H₅ | N | N | N | X |
| 869 | —NH₂ | —NH₂ | —CH₂CH₂OCH₂C₆H₅ | —CH₂CH₂OC₆H₅ | N | N | N | Y |
| 870 | —NH₂ | —NH₂ | —CH₂CH₂OCH₂C₆H₅ | —CH₂CH₂OC₆H₅ | N | N | N | Z |
| 871 | —NH₂ | —NH₂ | —CH₂CH₂OCH₂C₆H₅ | —CH₂CH₂OCH₂C₆H₅ | N | N | N | X |
| 872 | —NH₂ | —NH₂ | —CH₂CH₂OCH₂C₆H₅ | —CH₂CH₂OCH₂C₆H₅ | N | N | N | Y |
| 873 | —NH₂ | —NH₂ | —CH₂CH₂OCH₂C₆H₅ | —CH₂CH₂OCH₂C₆H₅ | N | N | N | Z |
| 874 | —NH₂ | —NH₂ | —CH₂CH₂OC₂H₄C₆H₅ | —CH₂CH₂OC₂H₄C₆H₅ | N | N | N | X |
| 875 | —NH₂ | —NH₂ | —CH₂CH₂OC₂H₄C₆H₅ | —CH₂CH₂OC₂H₄C₆H₅ | N | N | N | Y |
| 876 | —NH₂ | —NH₂ | —CH₂CH₂OC₂H₄C₆H₅ | —CH₂CH₂OC₂H₄C₆H₅ | N | N | N | Z |
| 817 | —NH₂ | —NH₂ | —CH₂CH₂OC(O)CH₃ | —CH₂CF₃ | N | N | N | X |
| 878 | —NH₂ | —NH₂ | —CH₂CH₂OC(O)CH₃ | —CH₂CF₃ | N | N | N | Y |
| 879 | —NH₂ | —NH₂ | —CH₂CH₂OC(O)CH₃ | —CH₂CF₃ | N | N | N | Z |
| 880 | —NH₂ | —NH₂ | —CH₂CH₂OC(O)CH₃ | —CH₂CH₂OCH₃ | N | N | N | X |
| 881 | —NH₂ | —NH₂ | —CH₂CH₂OC(O)CH₃ | —CH₂CH₂OCH₃ | N | N | N | Y |
| 882 | —NH₂ | —NH₂ | —CH₂CH₂OC(O)CH₃ | —CH₂CH₂OCH₃ | N | N | N | Z |
| 883 | —NH₂ | —NH₂ | —CH₂CH₂OC(O)CH₃ | —CH₂CH₂OC₆H₅ | N | N | N | X |
| 884 | —NH₂ | —NH₂ | —CH₂CH₂OC(O)CH₃ | —CH₂CH₂OC₆H₅ | N | N | N | Y |
| 885 | —NH₂ | —NH₂ | —CH₂CH₂OC(O)CH₃ | —CH₂CH₂OC₆H₅ | N | N | N | Z |
| 886 | —NH₂ | —NH₂ | —CH₂CH₂OC(O)CH₃ | —CH₂CH₂OCH₂C₆H₅ | N | N | N | X |
| 887 | —NH₂ | —NH₂ | —CH₂CH₂OC(O)CH₃ | —CH₂CH₂OCH₂C₆H₅ | N | N | N | Y |
| 888 | —NH₂ | —NH₂ | —CH₂CH₂OC(O)CH₃ | —CH₂CH₂OCH₂C₆H₅ | N | N | N | Z |
| 889 | —NH₂ | —NH₂ | —CH₂CH₂OC(O)CH₃ | —CH₂CH₂OC(O)CH₃ | N | N | N | X |
| 890 | —NH₂ | —NH₂ | —CH₂CH₂OC(O)CH₃ | —CH₂CH₂OC(O)CH₃ | N | N | N | Y |
| 891 | —NH₂ | —NH₂ | —CH₂CH₂OC(O)CH₃ | —CH₂CH₂OC(O)CH₃ | N | N | N | Z |
| 892 | —NH₂ | —NH₂ | —CH₂CH₂OC(O)C₂H₅ | —CH₂CH₂OC(O)C₂H₅ | N | N | N | X |
| 893 | —NH₂ | —NH₂ | —CH₂CH₂OC(O)C₂H₅ | —CH₂CH₂OC(O)C₂H₅ | N | N | N | Y |
| 894 | —NH₂ | —NH₂ | —CH₂CH₂OC(O)C₂H₅ | —CH₂CH₂OC(O)C₂H₅ | N | N | N | Z |
| 895 | —NH₂ | —NH₂ | —CH₂CH₂OC(O)C₃H₇ | —CH₂CH₂OC(O)C₃H₇ | N | N | N | X |
| 896 | —NH₂ | —NH₂ | —CH₂CH₂OC(O)C₃H₇ | —CH₂CH₂OC(O)C₃H₇ | N | N | N | Y |
| 897 | —NH₂ | —NH₂ | —CH₂CH₂OC(O)C₃H₇ | —CH₂CH₂OC(O)C₃H₇ | N | N | N | Z |
| 898 | —NH₂ | —NH₂ | —CH₂CH₂OC(O)C₄H₉ | —CH₂CH₂OC(O)C₄H₉ | N | N | N | X |
| 899 | —NH₂ | —NH₂ | —CH₂CH₂OC(O)C₄H₉ | —CH₂CH₂OC(O)C₄H₉ | N | N | N | Y |
| 900 | —NH₂ | —NH₂ | —CH₂CH₂OC(O)C₄H₉ | —CH₂CH₂OC(O)C₄H₉ | N | N | N | Z |
| 901 | —NH₂ | —NH₂ | —CH₃ | —CF₂CF₃ | N | N | C | X |
| 902 | —NH₂ | —NH₂ | —CH₃ | —CF₂CF₃ | N | N | C | Y |
| 903 | —NH₂ | —NH₂ | —CH₃ | —CH₂CF₃ | N | N | C | X |
| 904 | —NH₂ | —NH₂ | —CH₃ | —CH₂CF₃ | N | N | C | Y |
| 905 | —NH₂ | —NH₂ | —CF₂CF₃ | —CF₂CF₃ | N | N | C | X |
| 906 | —NH₂ | —NH₂ | —CF₂CF₃ | —CF₂CF₃ | N | N | C | Y |
| 907 | —NH₂ | —NH₂ | —CF₂CF₃ | —CH₂CF₃ | N | N | C | X |
| 908 | —NH₂ | —NH₂ | —CF₂CF₃ | —CH₂CF₃ | N | N | C | Y |
| 909 | —NH₂ | —NH₂ | —CH₂CF₃ | —CH₂CF₃ | N | N | C | X |
| 910 | —NH₂ | —NH₂ | —CH₂CF₃ | —CH₂CF₃ | N | N | C | Y |

TABLE 4-continued

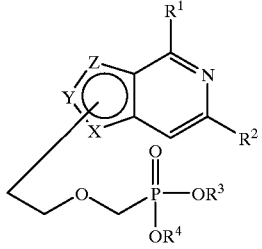

| Comp. No. | R¹ | R² | R³ | R⁴ | X | Y | Z | P.S. |
|---|---|---|---|---|---|---|---|---|
| 911 | —NH₂ | —NH₂ | —CH₂CH₂OCH₃ | —CH₂CF₃ | N | N | C | X |
| 912 | —NH₂ | —NH₂ | —CH₂CH₂OCH₃ | —CH₂CF₃ | N | N | C | Y |
| 913 | —NH₂ | —NH₂ | —CH₂CH₂OCH₃ | CH₂CH₂OCH₃ | N | N | C | X |
| 914 | —NH₂ | —NH₂ | —CH₂CH₂OCH₃ | —CH₂CH₂OCH₃ | N | N | C | Y |
| 915 | —NH₂ | —NH₂ | —CH₂CH₂OC₂H₅ | —CH₂CH₂OC₂H₅ | N | N | C | X |
| 916 | —NH₂ | —NH₂ | —CH₂CH₂OC₂H₅ | —CH₂CH₂OC₂H₅ | N | N | C | Y |
| 917 | —NH₂ | —NH₂ | —CH₂CH₂OC₃H₇ | —CH₂CH₂OC₃H₇ | N | N | C | X |
| 918 | —NH₂ | —NH₂ | —CH₂CH₂OC₃H₇ | —CH₂CH₂OC₃H₇ | N | N | C | Y |
| 919 | —NH₂ | —NH₂ | —CH₂CH₂OC₆H₅ | —CH₂CF₃ | N | N | C | X |
| 920 | —NH₂ | —NH₂ | —CH₂CH₂OC₆H₅ | —CH₂CF₃ | N | N | C | Y |
| 921 | —NH₂ | —NH₂ | —CH₂CH₂OC₆H₅ | —CH₂CH₂OCH₃ | N | N | C | X |
| 922 | —NH₂ | —NH₂ | —CH₂CH₂OC₆H₅ | —CH₂CH₂OCH₃ | N | N | C | Y |
| 923 | —NH₂ | —NH₂ | —CH₂CH₂OC₆H₅ | —CH₂CH₂OC₆H₅ | N | N | C | X |
| 924 | —NH₂ | —NH₂ | —CH₂CH₂OC₆H₅ | —CH₂CH₂OC₆H₅ | N | N | C | Y |
| 925 | —NH₂ | —NH₂ | —CH₂CH₂OCH₂C₆H₅ | —CH₂CF₃ | N | N | C | X |
| 926 | —NH₂ | —NH₂ | —CH₂CH₂OCH₂C₆H₅ | —CH₂CF₃ | N | N | C | Y |
| 927 | —NH₂ | —NH₂ | —CH₂CH₂OCH₂C₆H₅ | —CH₂CH₂OCH₃ | N | N | C | X |
| 928 | —NH₂ | —NH₂ | —CH₂CH₂OCH₂C₆H₅ | —CH₂CH₂OCH₃ | N | N | C | Y |
| 929 | —NH₂ | —NH₂ | —CH₂CH₂OCH₂C₆H₅ | —CH₂CH₂OC₆H₅ | N | N | C | X |
| 930 | —NH₂ | —NH₂ | —CH₂CH₂OCH₂C₆H₅ | —CH₂CH₂OC₆H₅ | N | N | C | Y |
| 931 | —NH₂ | —NH₂ | —CH₂CH₂OCH₂C₆H₅ | —CH₂CH₂OCH₂C₆H₅ | N | N | C | X |
| 932 | —NH₂ | —NH₂ | —CH₂CH₂OCH₂C₆H₅ | —CH₂CH₂OCH₂C₆H₅ | N | N | C | Y |
| 933 | —NH₂ | —NH₂ | —CH₂CH₂OC₂H₄C₆H₅ | —CH₂CH₂OC₂H₄C₆H₅ | N | N | C | X |
| 934 | —NH₂ | —NH₂ | —CH₂CH₂OC₂H₄C₆H₅ | —CH₂CH₂OC₂H₄C₆H₅ | N | N | C | Y |
| 935 | —NH₂ | —NH₂ | —CH₂CH₂OC(O)CH₃ | —CH₂CF₃ | N | N | C | X |
| 936 | —NH₂ | —NH₂ | —CH₂CH₂OC(O)CH₃ | —CH₂CF₃ | N | N | C | Y |
| 937 | —NH₂ | —NH₂ | —CH₂CH₂OC(O)CH₃ | —CH₂CH₂OCH₃ | N | N | C | X |
| 938 | —NH₂ | —NH₂ | —CH₂CH₂OC(O)CH₃ | —CH₂CH₂OCH₃ | N | N | C | Y |
| 939 | —NH₂ | —NH₂ | —CH₂CH₂OC(O)CH₃ | —CH₂CH₂OC₆H₅ | N | N | C | X |
| 940 | —NH₂ | —NH₂ | —CH₂CH₂OC(O)CH₃ | —CH₂CH₂OC₆H₅ | N | N | C | Y |
| 941 | —NH₂ | —NH₂ | —CH₂CH₂OC(O)CH₃ | —CH₂CH₂OCH₂C₆H₅ | N | N | C | X |
| 942 | —NH₂ | —NH₂ | —CH₂CH₂OC(O)CH₃ | —CH₂CH₂OCH₂C₆H₅ | N | N | C | Y |
| 943 | —NH₂ | —NH₂ | —CH₂CH₂OC(O)CH₃ | —CH₂CH₂OC(O)CH₃ | N | N | C | X |
| 944 | —NH₂ | —NH₂ | —CH₂CH₂OC(O)CH₃ | —CH₂CH₂OC(O)CH₃ | N | N | C | Y |
| 945 | —NH₂ | —NH₂ | —CH₂CH₂OC(O)C₂H₅ | —CH₂CH₂OC(O)C₂H₅ | N | N | C | X |
| 946 | —NH₂ | —NH₂ | —CH₂CH₂OC(O)C₂H₅ | —CH₂CH₂OC(O)C₂H₅ | N | N | C | Y |
| 947 | —NH₂ | —NH₂ | —CH₂CH₂OC(O)C₃H₇ | —CH₂CH₂OC(O)C₃H₇ | N | N | C | X |
| 948 | —NH₂ | —NH₂ | —CH₂CH₂OC(O)C₃H₇ | —CH₂CH₂OC(O)C₃H₇ | N | N | C | Y |
| 949 | —NH₂ | —NH₂ | —CH₂CH₂OC(O)C₄H₉ | —CH₂CH₂OC(O)C₄H₉ | N | N | C | X |
| 950 | —NH₂ | —NH₂ | —CH₂CH₂OC(O)C₄H₉ | —CH₂CH₂OC(O)C₄H₉ | N | N | C | Y |
| 951 | —NH₂ | —NH₂ | —CH₃ | —CF₂CF₃ | N | C | N | X |
| 952 | —NH₂ | —NH₂ | —CH₃ | —CF₂CF₃ | N | C | N | Z |
| 953 | —NH₂ | —NH₂ | —CH₃ | —CH₂CF₃ | N | C | N | X |
| 954 | —NH₂ | —NH₂ | —CH₃ | —CH₂CF₃ | N | C | N | Z |
| 955 | —NH₂ | —NH₂ | —CF₂CF₃ | —CF₂CF₃ | N | C | N | X |
| 956 | —NH₂ | —NH₂ | —CF₂CF₃ | —CF₂CF₃ | N | C | N | Z |
| 957 | —NH₂ | —NH₂ | —CF₂CF₃ | —CH₂CF₃ | N | C | N | X |
| 958 | —NH₂ | —NH₂ | —CF₂CF₃ | —CH₂CF₃ | N | C | N | Z |
| 959 | —NH₂ | —NH₂ | —CH₂CF₃ | —CH₂CF₃ | N | C | N | X |
| 960 | —NH₂ | —NH₂ | —CH₂CF₃ | —CH₂CF₃ | N | C | N | Z |
| 961 | —NH₂ | —NH₂ | —CH₂CH₂OCH₃ | —CH₂CF₃ | N | C | N | X |
| 962 | —NH₂ | —NH₂ | —CH₂CH₂OCH₃ | —CH₂CF₃ | N | C | N | Z |
| 963 | —NH₂ | —NH₂ | —CH₂CH₂OCH₃ | —CH₂CH₂OCH₃ | N | C | N | X |
| 964 | —NH₂ | —NH₂ | —CH₂CH₂OCH₃ | —CH₂CH₂OCH₃ | N | C | N | Z |
| 965 | —NH₂ | —NH₂ | —CH₂CH₂OC₂H₅ | —CH₂CH₂OC₂H₅ | N | C | N | X |
| 966 | —NH₂ | —NH₂ | —CH₂CH₂OC₂H₅ | —CH₂CH₂OC₂H₅ | N | C | N | Z |
| 967 | —NH₂ | —NH₂ | —CH₂CH₂OC₃H₇ | —CH₂CH₂OC₃H₇ | N | C | N | X |
| 968 | —NH₂ | —NH₂ | —CH₂CH₂OC₃H₇ | —CH₂CH₂OC₃H₇ | N | C | N | Z |
| 969 | —NH₂ | —NH₂ | —CH₂CH₂OC₆H₅ | —CH₂CF₃ | N | C | N | X |
| 970 | —NH₂ | —NH₂ | —CH₂CH₂OC₆H₅ | —CH₂CF₃ | N | C | N | Z |
| 971 | —NH₂ | —NH₂ | —CH₂CH₂OC₆H₅ | —CH₂CH₂OCH₃ | N | C | N | X |
| 972 | —NH₂ | —NH₂ | —CH₂CH₂OC₆H₅ | —CH₂CH₂OCH₃ | N | C | N | Z |

TABLE 4-continued

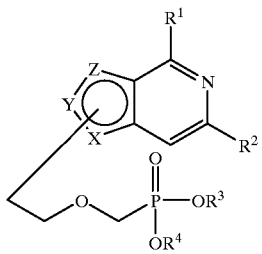

| Comp. No. | R¹ | R² | R³ | R⁴ | X | Y | Z | P.S. |
|---|---|---|---|---|---|---|---|---|
| 973 | —NH₂ | —NH₂ | —CH₂CH₂OC₆H₅ | —CH₂CH₂OC₆H₅ | N | C | N | X |
| 974 | —NH₂ | —NH₂ | —CH₂CH₂OC₆H₅ | —CH₂CH₂OC₆H₅ | N | C | N | Z |
| 975 | —NH₂ | —NH₂ | —CH₂CH₂OCH₂C₆H₅ | —CH₂CF₃ | N | C | N | X |
| 976 | —NH₂ | —NH₂ | —CH₂CH₂OCH₂C₆H₅ | —CH₂CF₃ | N | C | N | Z |
| 977 | —NH₂ | —NH₂ | —CH₂CH₂OCH₂C₆H₅ | —CH₂CH₂OCH₃ | N | C | N | X |
| 978 | —NH₂ | —NH₂ | —CH₂CH₂OCH₂C₆H₅ | —CH₂CH₂OCH₃ | N | C | N | Z |
| 979 | —NH₂ | —NH₂ | —CH₂CH₂OCH₂C₆H₅ | —CH₂CH₂OC₆H₅ | N | C | N | X |
| 980 | —NH₂ | —NH₂ | —CH₂CH₂OCH₂C₆H₅ | —CH₂CH₂OC₆H₅ | N | C | N | Z |
| 981 | —NH₂ | —NH₂ | —CH₂CH₂OCH₂C₆H₅ | —CH₂CH₂OCH₂C₆H₅ | N | C | N | X |
| 982 | —NH₂ | —NH₂ | —CH₂CH₂OCH₂C₆H₅ | —CH₂CH₂OCH₂C₆H₅ | N | C | N | Z |
| 983 | —NH₂ | —NH₂ | —CH₂CH₂OC₂H₄C₆H₅ | —CH₂CH₂OC₂H₄C₆H₅ | N | C | N | X |
| 984 | —NH₂ | —NH₂ | —CH₂CH₂OC₂H₄C₆H₅ | —CH₂CH₂OC₂H₄C₆H₅ | N | C | N | Z |
| 985 | —NH₂ | —NH₂ | —CH₂CH₂OC(O)CH₃ | —CH₂CF₃ | N | C | N | X |
| 986 | —NH₂ | —NH₂ | —CH₂CH₂OC(O)CH₃ | —CH₂CF₃ | N | C | N | Z |
| 987 | —NH₂ | —NH₂ | —CH₂CH₂OC(O)CH₃ | —CH₂CH₂OCH₃ | N | C | N | X |
| 988 | —NH₂ | —NH₂ | —CH₂CH₂OC(O)CH₃ | —CH₂CH₂OCH₃ | N | C | N | Z |
| 989 | —NH₂ | —NH₂ | —CH₂CH₂OC(O)CH₃ | —CH₂CH₂OC₆H₅ | N | C | N | X |
| 990 | —NH₂ | —NH₂ | —CH₂CH₂OC(O)CH₃ | —CH₂CH₂OC₆H₅ | N | C | N | Z |
| 991 | —NH₂ | —NH₂ | —CH₂CH₂OC(O)CH₃ | —CH₂CH₂OCH₂C₆H₅ | N | C | N | X |
| 992 | —NH₂ | —NH₂ | —CH₂CH₂OC(O)CH₃ | —CH₂CH₂OCH₂C₆H₅ | N | C | N | Z |
| 993 | —NH₂ | —NH₂ | —CH₂CH₂OC(O)CH₃ | —CH₂CH₂OC(O)CH₃ | N | C | N | X |
| 994 | —NH₂ | —NH₂ | —CH₂CH₂OC(O)CH₃ | —CH₂CH₂OC(O)CH₃ | N | C | N | Z |
| 995 | —NH₂ | —NH₂ | —CH₂CH₂OC(O)C₂H₅ | —CH₂CH₂OC(O)C₂H₅ | N | C | N | X |
| 996 | —NH₂ | —NH₂ | —CH₂CH₂OC(O)C₂H₅ | —CH₂CH₂OC(O)C₂H₅ | N | C | N | Z |
| 997 | —NH₂ | —NH₂ | —CH₂CH₂OC(O)C₃H₇ | —CH₂CH₂OC(O)C₃H₇ | N | C | N | X |
| 998 | —NH₂ | —NH₂ | —CH₂CH₂OC(O)C₃H₇ | —CH₂CH₂OC(O)C₃H₇ | N | C | N | Z |
| 999 | —NH₂ | —NH₂ | —CH₂CH₂OC(O)C₄H₉ | —CH₂CH₂OC(O)C₄H₉ | N | C | N | X |
| 1000 | —NH₂ | —NH₂ | —CH₂CH₂OC(O)C₄H₉ | —CH₂CH₂OC(O)C₄H₉ | N | C | N | Z |

TABLE 5

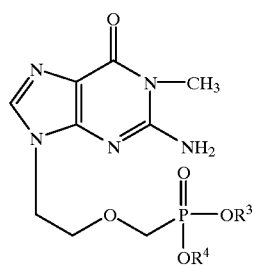

| Comp. No. | R³ | R⁴ |
|---|---|---|
| 1001 | —CH₃ | —CF₂CF₃ |
| 1002 | —CH₃ | —CH₂CF₃ |
| 1003 | —CF₂CF₃ | —CF₂CF₃ |
| 1004 | —CF₂CF₃ | —CH₂CF₃ |
| 1005 | —CH₂CF₃ | —CH₂CF₃ |
| 1006 | —CH₂CH₂OCH₃ | —CH₂CF₃ |
| 1007 | —CH₂CH₂OCH₃ | —CH₂CH₂OCH₃ |

TABLE 5-continued

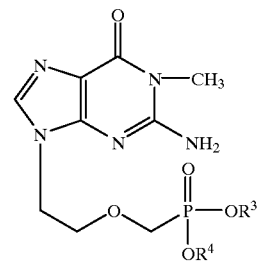

| Comp. No. | R³ | R⁴ |
|---|---|---|
| 1008 | —CH₂CH₂OC₂H₅ | —CH₂CH₂OC₂H₅ |
| 1009 | —CH₂CH₂OC₃H₇ | —CH₂CH₂OC₃H₇ |
| 1010 | —CH₂CH₂OC₆H₅ | —CH₂CF₃ |
| 1011 | —CH₂CH₂OC₆H₅ | —CH₂CH₂OCH₃ |
| 1012 | —CH₂CH₂OC₆H₅ | —CH₂CH₂OC₆H₅ |
| 1013 | —CH₂CH₂OCH₂C₆H₅ | —CH₂CF₃ |
| 1014 | —CH₂CH₂OCH₂C₆H₅ | —CH₂CH₂OCH₃ |

TABLE 5-continued

[Structure: 1-methyl guanine with N9-CH2CH2-O-CH2-P(=O)(OR³)(OR⁴)]

| Comp. No. | R³ | R⁴ |
|---|---|---|
| 1015 | —CH$_2$CH$_2$OCH$_2$C$_6$H$_5$ | —CH$_2$CH$_2$OC$_6$H$_5$ |
| 1016 | —CH$_2$CH$_2$OCH$_2$C$_6$H$_5$ | —CH$_2$CH$_2$OCH$_2$C$_6$H$_5$ |
| 1017 | —CH$_2$CH$_2$OC$_2$H$_4$C$_6$H$_5$ | —CH$_2$CH$_2$OC$_2$H$_4$C$_6$H$_5$ |
| 1018 | —CH$_2$CH$_2$OC(O)CH$_3$ | —CH$_2$CF$_3$ |
| 1019 | —CH$_2$CH$_2$OC(O)CH$_3$ | —CH$_2$CH$_2$OC$_6$H$_5$ |
| 1020 | —CH$_2$CH$_2$OC(O)CH$_3$ | —CH$_2$CH$_2$OCH$_2$C$_6$H$_5$ |
| 1021 | —CH$_2$CH$_2$OC(O)CH$_3$ | —CH$_2$CH$_2$OCH$_2$C$_6$H$_5$ |
| 1022 | —CH$_2$CH$_2$OC(O)CH$_3$ | —CH$_2$CH$_2$OC(O)CH$_3$ |
| 1023 | —CH$_2$CH$_2$OC(O)C$_2$H$_5$ | —CH$_2$CH$_2$OC(O)C$_2$H$_5$ |
| 1024 | —CH$_2$CH$_2$OC(O)C$_3$H$_7$ | —CH$_2$CH$_2$OC(O)C$_3$H$_7$ |
| 1025 | —CH$_2$CH$_2$OC(O)C$_4$H$_9$ | —CH$_2$CH$_2$OC(O)C$_4$H$_9$ |

TABLE 6

[Structure: 6-(4-methylphenylthio)-2-aminopurine with N9-CH2CH2-O-CH2-P(=O)(OR³)(OR⁴)]

| Comp. No. | R³ | R⁴ |
|---|---|---|
| 1026 | —CH$_3$ | —CF$_2$CF$_3$ |
| 1027 | —CH$_3$ | —CH$_2$CF$_3$ |
| 1028 | —CF$_2$CF$_3$ | —CF$_2$CF$_3$ |
| 1029 | —CF$_2$CF$_3$ | —CH$_2$CF$_3$ |
| 1030 | —CH$_2$CF$_3$ | —CH$_2$CF$_3$ |
| 1031 | —CH$_2$CH$_2$OCH$_3$ | —CH$_2$CF$_3$ |
| 1032 | —CH$_2$CH$_2$OCH$_3$ | —CH$_2$CH$_2$OCH$_3$ |
| 1033 | —CH$_2$CH$_2$OC$_2$H$_5$ | —CH$_2$CH$_2$OC$_2$H$_5$ |
| 1034 | —CH$_2$CH$_2$OC$_3$H$_7$ | —CH$_2$CH$_2$OC$_3$H$_7$ |
| 1035 | —CH$_2$CH$_2$OC$_6$H$_5$ | —CH$_2$CF$_3$ |
| 1036 | —CH$_2$CH$_2$OC$_6$H$_5$ | —CH$_2$CH$_2$OCH$_3$ |
| 1037 | —CH$_2$CH$_2$OC$_6$H$_5$ | —CH$_2$CH$_2$OC$_6$H$_5$ |
| 1038 | —CH$_2$CH$_2$OCH$_2$C$_6$H$_5$ | —CH$_2$CF$_3$ |
| 1039 | —CH$_2$CH$_2$OCH$_2$C$_6$H$_5$ | —CH$_2$CH$_2$OCH$_3$ |
| 1040 | —CH$_2$CH$_2$OCH$_2$C$_6$H$_5$ | —CH$_2$CH$_2$OC$_6$H$_5$ |
| 1041 | —CH$_2$CH$_2$OCH$_2$C$_6$H$_5$ | —CH$_2$CH$_2$OCH$_2$C$_6$H$_5$ |
| 1042 | —CH$_2$CH$_2$OC$_2$H$_4$C$_6$H$_5$ | —CH$_2$CH$_2$OC$_2$H$_4$C$_6$H$_5$ |
| 1043 | —CH$_2$CH$_2$OC(O)CH$_3$ | —CH$_2$CF$_3$ |
| 1044 | —CH$_2$CH$_2$OC(O)CH$_3$ | —CH$_2$CH$_2$OC$_6$H$_5$ |
| 1045 | —CH$_2$CH$_2$OC(O)CH$_3$ | —CH$_2$CH$_2$OCH$_2$C$_6$H$_5$ |
| 1046 | —CH$_2$CH$_2$OC(O)CH$_3$ | —CH$_2$CH$_2$OCH$_2$C$_6$H$_5$ |
| 1047 | —CH$_2$CH$_2$OC(O)CH$_3$ | —CH$_2$CH$_2$OC(O)CH$_3$ |

TABLE 6-continued

[Structure: 6-(4-methylphenylthio)-2-aminopurine with N9-CH2CH2-O-CH2-P(=O)(OR³)(OR⁴)]

| Comp. No. | R³ | R⁴ |
|---|---|---|
| 1048 | —CH$_2$CH$_2$OC(O)C$_2$H$_5$ | —CH$_2$CH$_2$OC(O)C$_2$H$_5$ |
| 1049 | —CH$_2$CH$_2$OC(O)C$_3$H$_7$ | —CH$_2$CH$_2$OC(O)C$_3$H$_7$ |
| 1050 | —CH$_2$CH$_2$OC(O)C$_4$H$_9$ | —CH$_2$CH$_2$OC(O)C$_4$H$_9$ |

TABLE 7

[Structure: 6-(4-methylphenylthio)-2-oxopurine with N9-CH2CH2-O-CH2-P(=O)(OR³)(OR⁴)]

| Comp. No. | R³ | R⁴ |
|---|---|---|
| 1051 | —CH$_3$ | —CF$_2$CF$_3$ |
| 1052 | —CH$_3$ | —CH$_2$CF$_3$ |
| 1053 | —CF$_2$CF$_3$ | —CF$_2$CF$_3$ |
| 1054 | —CF$_2$CF$_3$ | —CH$_2$CF$_3$ |
| 1055 | —CH$_2$CF$_3$ | —CH$_2$CF$_3$ |
| 1056 | —CH$_2$CH$_2$OCH$_3$ | —CH$_2$CF$_3$ |
| 1057 | —CH$_2$CH$_2$OCH$_3$ | —CH$_2$CH$_2$OCH$_3$ |
| 1058 | —CH$_2$CH$_2$OC$_2$H$_5$ | —CH$_2$CH$_2$OC$_2$H$_5$ |
| 1059 | —CH$_2$CH$_2$OC$_3$H$_7$ | —CH$_2$CH$_2$OC$_3$H$_7$ |
| 1060 | —CH$_2$CH$_2$OC$_6$H$_5$ | —CH$_2$CF$_3$ |
| 1061 | —CH$_2$CH$_2$OC$_6$H$_5$ | —CH$_2$CH$_2$OCH$_3$ |
| 1062 | —CH$_2$CH$_2$OC$_6$H$_5$ | —CH$_2$CH$_2$OC$_6$H$_5$ |
| 1063 | —CH$_2$CH$_2$OCH$_2$C$_6$H$_5$ | —CH$_2$CF$_3$ |
| 1064 | —CH$_2$CH$_2$OCH$_2$C$_6$H$_5$ | —CH$_2$CH$_2$OCH$_3$ |
| 1065 | —CH$_2$CH$_2$OCH$_2$C$_6$H$_5$ | —CH$_2$CH$_2$OC$_6$H$_5$ |
| 1066 | —CH$_2$CH$_2$OCH$_2$C$_6$H$_5$ | —CH$_2$CH$_2$OCH$_2$C$_6$H$_5$ |
| 1067 | —CH$_2$CH$_2$OC$_2$H$_4$C$_6$H$_5$ | —CH$_2$CH$_2$OC$_2$H$_4$C$_6$H$_5$ |
| 1068 | —CH$_2$CH$_2$OC(O)CH$_3$ | —CH$_2$CF$_3$ |
| 1069 | —CH$_2$CH$_2$OC(O)CH$_3$ | —CH$_2$CH$_2$OC$_6$H$_5$ |
| 1070 | —CH$_2$CH$_2$OC(O)CH$_3$ | —CH$_2$CH$_2$OCH$_2$C$_6$H$_5$ |
| 1071 | —CH$_2$CH$_2$OC(O)CH$_3$ | —CH$_2$CH$_2$OCH$_2$C$_6$H$_5$ |
| 1072 | —CH$_2$CH$_2$OC(O)CH$_3$ | —CH$_2$CH$_2$OC(O)CH$_3$ |
| 1073 | —CH$_2$CH$_2$OC(O)C$_2$H$_5$ | —CH$_2$CH$_2$OC(O)C$_2$H$_5$ |
| 1074 | —CH$_2$CH$_2$OC(O)C$_3$H$_7$ | —CH$_2$CH$_2$OC(O)C$_3$H$_7$ |
| 1075 | —CH$_2$CH$_2$OC(O)C$_4$H$_9$ | —CH$_2$CH$_2$OC(O)C$_4$H$_9$ |

TABLE 1

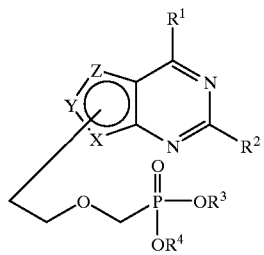

| Comp. No. | R¹ | R² | R³ | R⁴ | X | Y | Z | P.S. |
|---|---|---|---|---|---|---|---|---|
| 1076 | —Cl | —H | —CH$_3$ | —CF$_2$CF$_3$ | N | C | N | X |
| 1077 | —Cl | —H | —CH$_3$ | —CF$_2$CF$_3$ | N | C | N | Z |
| 1078 | —Cl | —H | —CH$_3$ | —CH$_2$CF$_3$ | N | C | N | X |
| 1079 | —Cl | —H | —CH$_3$ | —CH$_2$CF$_3$ | N | C | N | Z |
| 1080 | —Cl | —H | —CF$_2$CF$_3$ | —CF$_2$CF$_3$ | N | C | N | X |
| 1081 | —Cl | —H | —CF$_2$CF$_3$ | —CF$_2$CF$_3$ | N | C | N | Z |
| 1082 | —Cl | —H | —CF$_2$CF$_3$ | —CH$_2$CF$_3$ | N | C | N | X |
| 1083 | —Cl | —H | —CF$_2$CF$_3$ | —CH$_2$CF$_3$ | N | C | N | Z |
| 1084 | —Cl | —H | —CH$_2$CF$_3$ | —CH$_2$CF$_3$ | N | C | N | X |
| 1085 | —Cl | —H | —CH$_2$CF$_3$ | —CH$_2$CF$_3$ | N | C | N | Z |
| 1086 | —Cl | —H | —CH$_2$CH$_2$OCH$_3$ | —CH$_2$CF$_3$ | N | C | N | X |
| 1087 | —Cl | —H | —CH$_2$CH$_2$OCH$_3$ | —CH$_2$CF$_3$ | N | C | N | Z |
| 1088 | —Cl | —H | —CH$_2$CH$_2$OCH$_3$ | —CH$_2$CH$_2$OCH$_3$ | N | C | N | X |
| 1089 | —Cl | —H | —CH$_2$CH$_2$OCH$_3$ | —CH$_2$CH$_2$OCH$_3$ | N | C | N | Z |
| 1090 | —Cl | —H | —CH$_2$CH$_2$OC$_2$H$_5$ | —CH$_2$CH$_2$OC$_2$H$_5$ | N | C | N | X |
| 1091 | —Cl | —H | —CH$_2$CH$_2$OC$_2$H$_5$ | —CH$_2$CH$_2$OC$_2$H$_5$ | N | C | N | Z |
| 1092 | —Cl | —H | —CH$_2$CH$_2$OC$_3$H$_7$ | —CH$_2$CH$_2$OC$_3$H$_7$ | N | C | N | X |
| 1093 | —Cl | —H | —CH$_2$CH$_2$OC$_3$H$_7$ | —CH$_2$CH$_2$OC$_3$H$_7$ | N | C | N | Z |
| 1094 | —Cl | —H | —CH$_2$CH$_2$OC$_6$H$_5$ | —CH$_2$CF$_3$ | N | C | N | X |
| 1095 | —Cl | —H | —CH$_2$CH$_2$OC$_6$H$_5$ | —CH$_2$CF$_3$ | N | C | N | Z |
| 1096 | —Cl | —H | —CH$_2$CH$_2$OC$_6$H$_5$ | —CH$_2$CH$_2$OCH$_3$ | N | C | N | X |
| 1097 | —Cl | —H | —CH$_2$CH$_2$OC$_6$H$_5$ | —CH$_2$CH$_2$OCH$_3$ | N | C | N | Z |
| 1098 | —Cl | —H | —CH$_2$CH$_2$OC$_6$H$_5$ | —CH$_2$CH$_2$OC$_6$H$_5$ | N | C | N | X |
| 1099 | —Cl | —H | —CH$_2$CH$_2$OC$_6$H$_5$ | —CH$_2$CH$_2$OC$_6$H$_5$ | N | C | N | Z |
| 1100 | —Cl | —H | —CH$_2$CH$_2$OCH$_2$C$_6$H$_5$ | —CH$_2$CF$_3$ | N | C | N | X |
| 1101 | —Cl | —H | —CH$_2$CH$_2$OCH$_2$C$_6$H$_5$ | —CH$_2$CF$_3$ | N | C | N | Z |
| 1102 | —Cl | —H | —CH$_2$CH$_2$OCH$_2$C$_6$H$_5$ | —CH$_2$CH$_2$OCH$_3$ | N | C | N | X |
| 1103 | —Cl | —H | —CH$_2$CH$_2$OCH$_2$C$_6$H$_5$ | —CH$_2$CH$_2$OCH$_3$ | N | C | N | Z |
| 1104 | —Cl | —H | —CH$_2$CH$_2$OCH$_2$C$_6$H$_5$ | —CH$_2$CH$_2$OC$_6$H$_5$ | N | C | N | X |
| 1105 | —Cl | —H | —CH$_2$CH$_2$OCH$_2$C$_6$H$_5$ | —CH$_2$CH$_2$OC$_6$H$_5$ | N | C | N | Z |
| 1106 | —Cl | —H | —CH$_2$CH$_2$OCH$_2$C$_6$H$_5$ | —CH$_2$CH$_2$OCH$_2$C$_6$H$_5$ | N | C | N | X |
| 1107 | —Cl | —H | —CH$_2$CH$_2$OCH$_2$C$_6$H$_5$ | —CH$_2$CH$_2$OCH$_2$C$_6$H$_5$ | N | C | N | Z |
| 1108 | —Cl | —H | —CH$_2$CH$_2$OC$_2$H$_4$C$_6$H$_5$ | —CH$_2$CH$_2$OC$_2$H$_4$C$_6$H$_5$ | N | C | N | X |
| 1109 | —Cl | —H | —CH$_2$CH$_2$OC$_2$H$_4$C$_6$H$_5$ | —CH$_2$CH$_2$OC$_2$H$_4$C$_6$H$_5$ | N | C | N | Z |
| 1110 | —Cl | —H | —CH$_2$CH$_2$OC(O)CH$_3$ | —CH$_2$CF$_3$ | N | C | N | X |
| 1111 | —Cl | —H | —CH$_2$CH$_2$OC(O)CH$_3$ | —CH$_2$CF$_3$ | N | C | N | Z |
| 1112 | —Cl | —H | —CH$_2$CH$_2$OC(O)CH$_3$ | —CH$_2$CH$_2$OCH$_3$ | N | C | N | X |
| 1113 | —Cl | —H | —CH$_2$CH$_2$OC(O)CH$_3$ | —CH$_2$CH$_2$OCH$_3$ | N | C | N | Z |
| 1114 | —Cl | —H | —CH$_2$CH$_2$OC(O)CH$_3$ | —CH$_2$CH$_2$OC$_6$H$_5$ | N | C | N | X |
| 1115 | —Cl | —H | —CH$_2$CH$_2$OC(O)CH$_3$ | —CH$_2$CH$_2$OC$_6$H$_5$ | N | C | N | Z |
| 1116 | —Cl | —H | —CH$_2$CH$_2$OC(O)CH$_3$ | —CH$_2$CH$_2$OCH$_2$C$_6$H$_5$ | N | C | N | X |
| 1117 | —Cl | —H | —CH$_2$CH$_2$OC(O)CH$_3$ | —CH$_2$CH$_2$OCH$_2$C$_6$H$_5$ | N | C | N | Z |
| 1118 | —Cl | —H | —CH$_2$CH$_2$OC(O)CH$_3$ | —CH$_2$CH$_2$OC(O)CH$_3$ | N | C | N | X |
| 1119 | —Cl | —H | —CH$_2$CH$_2$OC(O)CH$_3$ | —CH$_2$CH$_2$OC(O)CH$_3$ | N | C | N | Z |
| 1120 | —Cl | —H | —CH$_2$CH$_2$OC(O)C$_2$H$_5$ | —CH$_2$CH$_2$OC(O)C$_2$H$_5$ | N | C | N | X |
| 1121 | —Cl | —H | —CH$_2$CH$_2$OC(O)C$_2$H$_5$ | —CH$_2$CH$_2$OC(O)C$_2$H$_5$ | N | C | N | Z |
| 1122 | —Cl | —H | —CH$_2$CH$_2$OC(O)C$_3$H$_7$ | —CH$_2$CH$_2$OC(O)C$_3$H$_7$ | N | C | N | X |
| 1123 | —Cl | —H | —CH$_2$CH$_2$OC(O)C$_3$H$_7$ | —CH$_2$CH$_2$OC(O)C$_3$H$_7$ | N | C | N | Z |
| 1124 | —Cl | —H | —CH$_2$CH$_2$OC(O)C$_4$H$_9$ | —CH$_2$CH$_2$OC(O)C$_4$H$_9$ | N | C | N | X |
| 1125 | —Cl | —H | —CH$_2$CH$_2$OC(O)C$_4$H$_9$ | —CH$_2$CH$_2$OC(O)C$_4$H$_9$ | N | C | N | Z |

The compound of the present invention may be synthesized according to the following reaction scheme (1) or (2):

Reaction Scheme (I):

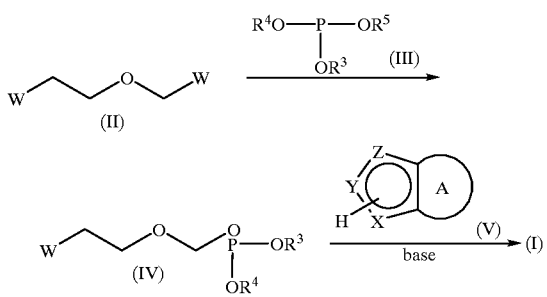

(wherein, $R^1$ to $R^4$, and a ring A are as defined above; $R^5$ is an ethyl group having one or more substituents selected from a group consisting of fluorine, $C_1$–$C_4$ alkoxy, phenoxy, $C_7$–$C_{10}$ phenylalkoxy, $C_2$–$C_5$ acyloxy, $C_1$–$C_4$ acylamino and hydroxyl; W is a leaving group such as halogen, paratoluenesulfonyloxy, methanesulfonyloxy, trifluoromethanesulfonyloxy).

A compound of Formula (II) is reacted with a compound of Formula (III) at 10–250° C., preferably at 130–180° C. for 0.1–20 hours, preferably for 3–15 hours.

A compound of Formula (IV) may be separated and purified, as needed, by the conventional means for separation and purification, for example, by distillation, adsorption, partition chromatography. A compound of Formula (IV) may be separated and purified as described above, but may be directly used in the subsequent reaction without purification.

Subsequently, a compound of Formula (IV) is reacted with a compound of Formula (V) in the presence of a base, for example, sodium carbonate, potassium carbonate, cesium carbonate, sodium hydride, potassium hydride, triethylamine, diazabicycloundecene in a solvent such as acetonitrile, tetrahydrofuran, dimethylsulfoxide, dimethylformamide, methylpyrrolidone at 10–200° C., preferably at 50–150° C., for 0.1 to 100 hours, preferably for 5–20 hours to give a compound (I).

Reaction Scheme (2):

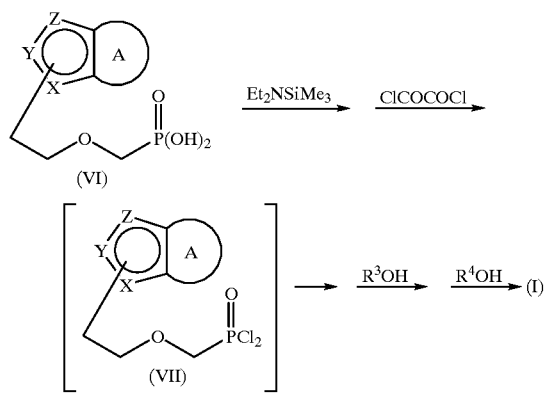

(wherein, $R^1$ to $R^4$, and a ring A are as defined above; Me is methyl and Et is ethyl)

A compound of Formula (VI) is reacted with trimethylsilyldiethylamine in a solvent, for example, in a chlorinated solvent such as dichloromethane, dichloroethane, chloroform at the temperature around room temperature for about an hour. In this case, two moles or more trimethylsilyldiethylamine is used based on one mole of a compound of Formula (VI).

Subsequently, after the reaction mixture is concentrated to dryness, the residue is dissolved in a chlorinated solvent such as dichloromethane, and two mole or more oxalyl chloride is added to 1 mole of the compound of Formula (VI), and the reaction is carried out in the presence of a catalytic amount of dimethylformamide under ice cooling for about an hour, then at the temperature around room temperature for about an hour.

After a solvent is distilled off, thus obtained compound of Formula (VII) without purification is usually reacted with $R^3OH$, $R^4OH$ in a solvent, for example, a chlorinated solvent such as dichloromethane or pyridine, acetonitrile, tetrahydrofuran, dimethylsulfoxide, dimethylformamide, methylpyrrolidone, etc. at 10–100° C., preferably at 20–30° C. for 0.1–100 hours, preferably for 5–24 hours to give a compound (I).

A compound of Formula (I) which may be obtained according to the above reaction scheme (1) or (2) may be separated and purified by properly selecting conventional means for separation and purification for nucleotide, for example, recrystallization, adsorption, ion-exchange, partition chromatography or the like, as needed. Various base derivatives may be derived from thus obtained compound of Formula (I) according to the known methods, as needed.

As the compound of Formula (II), (III) or (VI) in the above reaction schemes, those commercially available reagents may be purchased and used. Alternatively, those synthesized according to the known methods may be suitably used.

As shown in the following experimental examples, the compound of the present invention may be expected as antiviral agents which can be orally administered, and further expected to possess antineoplastic activity like other ionic phosphonate-nucleotide analogs. The viruses of interest may not be particularly limited, but include, for example, RNA viruses such as human immunodeficiency virus, influenza virus, hepatitis C virus; DNA viruses such as herpes simplex virus type-I, herpes simplex virus type-II, cytomegalovirus, herpes zoster, hepatitis B virus. More preferably, it is hepatitis B virus.

The compound of the present invention can be orally administered to a human patient. The dose is appropriately determined depending on, for example, the age, the conditions, the weight of the subject. Generally, 1–1,000 mg/kg, preferably 5–50 mg/kg is administered once or more daily.

The compound of the present invention is preferably used as a composition comprising pharmaceutically acceptable carrier such as conventional pharmaceutical carrier, excipient, etc. Such carrier may be either solid or liquid. Solid carrier includes, for example, lactose, kaolin, sucrose, crystalline cellulose, corn starch, talc, agar, pectin, stearic acid, magnesium stearate, lecithin, sodium chloride; and liquid carrier includes, for example, glycerin, peanut oil, polyvinyl pyrrolidone, olive oil, ethanol, benzyl alcohol, propylene glycol, physiological saline, water, etc.

Various dosage form may be employed, including tablets, powders, granules, troches, etc. when a solid carrier is used; and syrups, soft gelatin capsules, gels, pastes, etc. when a liquid carrier is used.

EXAMPLE

The present invention will be explained in detail in the following examples, which are not a limitation of the scope of the invention.

Example 1
Production of 9-[2-[bis(2,2,2-trifluoroethyl)phosphonylmethoxy]ethyl]adenine (compound No. 309 in Table 1)

2-Chloroethylchloromethylether (1.96 g, 15.2 mmol) was reacted with tris(2,2,2-trifluoroethyl)phosphite (5 g, 15.2 mmol) at 160° C. for 14 hours to quantitatively obtain 5.15 g of 2-[bis(2,2,2-trifluoroethyl)phosphonylmethoxy]ethyl chloride.

Adenine (2.07 g, 15.3 mmol) was suspended in dimethylformamide (30 ml) and reacted with sodium hydride (60% in mineral oil, 0.61 g) at 100° C. for an hour. Subsequently, 2-[bis(2,2,2-trifluoroethyl)phosphonylmethoxy]ethyl chloride (5.15 g) was added to the above reaction solution and reacted at 100° C. for 5 hours. After reaction was over, the product was cooled to room temperature and concentrated to dryness. The residue was dissolved in chloroform, adsorbed on silica gel column and eluted with 5% methanol/chloroform to give the title compound (2.77 g, 42%).

m.p.: 111–113° C. (ethyl acetate/hexane)

1H-NMR (CDCl3, δ): 3.91 (d, J=8.0 Hz, 2H) 3.94 (t, J=5.0 Hz, 2 H) 4.30–4.39 (m, 6H) 6.00 (br, 2H) 7.83 (s, 1H) 8.31 (s. 1H)

Example 2
Production of 9-[2-[bis(2,2,2-trifluoroethyl)phosphonylmethoxy]ethyl]-2,6-diaminopurine (compound No. 459 in Table 1)

The procedure in Example 1 was repeated, except that 2,6-diaminopurine was used instead of adenine, to obtain the title compound.

m.p.: 108° C. (ether)

1H-NMR (CDCl3, δ): 3.91–3.95 (m, 4H) 4.24 (t, J=5.1 Hz, 2H) 4.30–4.42 (m, 4H) 4.68 (br, 2H) 5.32 (br, 2H) 7.57 (s, 1H)

Example 3
Production of 9-[2-[bis(2,2,2-trifluoroethyl)phosphonylmethoxy]ethyl]-2-amino-6-chloropurine (compound No. 509 in Table 1)

The procedure in Example 1 was repeated, except that 2-amino-6-chloropurine was used instead of adenine, to obtain the title compound.

m.p.: 132° C. (ether)

1H-NMR (CDCl3, δ) :3.91 (t, J=4.7 Hz, 2H) 3.94 (d, J=7.6 Hz, 2H) 4.30 (t, J=4.7 Hz, 2H) 4.35–4.49 (m, 4H) 5.16 (br, 2H) 7.83 (s, 1H)

Example 4
Production of 7-[2-[bis(2,2,2-trifluoroethyl)phosphonylmethoxy]ethyl]-2-amino-6-chloropurine (compound No. 510 in Table 1)

The procedure in Example 1 was repeated, except that 2-amino-6-chloropurine was used instead of adenine, to obtain the title compound.

m.p.: amorphous

1H-NMR (CDCl3, δ): 3.93 (t, J=5.1 Hz, 2H) 3.94 (d, J=7.7 Hz, 2H) 4.24 (t, J=5.1 Hz, 2H) 4.31–4.42 (m, 4H) 4.66 (br, 2H) 5.27 (br, 2H) 7.56 (s, 1H)

Example 5
Production of 9-[2-[bis(2,2,2-trifluoroethyl)phosphonylmethoxy]ethyl]-8-aza-2,6-diaminopurine (compound No. 663 in Table 1)

The procedure in Example 1 was repeated, except that 8-aza-2,6-diaminopurine was used instead of adenine, to obtain the title compound.

m.p.: 169° C. (ethanol)

$^1$H-NMR (Me$_2$SO-d$_6$, δ) : 3.98 (t, J=5.1 Hz, 2H) 4.11 (d, J=7.8 Hz, 2H) 4.46–4.86 (m, 6H) 6.38 (br, 2H) 7.18–8.00 (m, 2H)

Example 6
Production of 8-[2-[bis(2,2,2-trifluoroethyl)phosphonylmethoxy]ethyl]-8-aza-2,6-diaminopurine (compound No. 664 in Table 1)

The procedure in Example 1 was repeated, except that 8-aza-2,6-diaminopurine was used instead of adenine, to obtain the title compound.

m.p.: 128° C. (diisopropyl ether)

1H-NMR (Me2SO-d6, δ): 4.03–4.15 (m, 4H) 4.55–4.71 (m, 4H) 6.05 (br, 2H) 7.50 (br, 2H)

Example 7
Production of 7-[2-[bis(2,2,2-trifluoroethyl)phosphonylmethoxy]ethyl]theophylline (compound No. 805 in Table 3)

The procedure in Example 1 was repeated, except that theophylline was used instead of adenine, to obtain the title compound.

m.p.: 77° C. (hexane)

1H-NMR (CDCl3, δ): 3.41 (s, 3H) 3.60 (s, 3H) 3.93 (d, J=8.1 Hz, 2H) 3.94 (t, J=5.0 Hz, 2H) 4.31–4.48 (m, 4H) 4.52 (t, J=5.0 Hz, 2H) 7.60 (s, 1H)

Example 8
Production of 9-[2-[bis(2,2,2-trifluoroethyl)phosphonylmethoxy]ethyl]-2,6-dichloropurine (compound No. 559 in Table 1)

The procedure in Example 1 was repeated, except that 2,6-dichloropurine was used instead of adenine, to obtain the title compound.

m.p.: 71–72° C. (ethyl acetate/hexane)

1H-NMR (CDCl3, δ) : 3.90–4.08 (m, 4H) 4.32–4.52 (m, 6H) 8.19 (s, 1H)

Example 9
Production of 9-[2-[bis(2,2,2-trifluoroethyl)phosphonylmethoxy]ethyl]-3-deaza-8-aza-2,6-diaminopurine (compound No. 838 in Table 4)

The procedure in Example 1 was repeated, except that 3-deaza-8-aza-2,6-diaminopurine was used instead of adenine, to obtain the title compound.

m.p.: 116–122° C. (ether)

$^1$H-NMR (Me$_2$SO-d$_6$, δ): 3.94 (t, J=5.2 Hz, 2H) 4.09 (d, J=7.7 Hz, 2H) 4.46–4.78 (m, 6H) 5.55 (s, 2H) 5.57 (s, 1H) 6.66 (s, 2H)

Example 10
Production of 9-[2-[bis(2,2,2-trifluoroethyl)phosphonylmethoxy]ethyl]-7-deaza-8-aza-2,6-diaminopurine (compound No. 734 in Table 1)

The procedure in Example 1 was repeated, except that 7-deaza-8-aza-2,6-diaminopurine was used instead of adenine, to obtain the title compound.

m.p.: 54–64° C. (ether)

$^1$H-NMR (Me$_2$SO-d$_6$, δ): 3.91 (t, J=5.3 Hz, 2H) 4.07 (d, J=8.0 Hz, 2H) 4.27 (t, J=5.3 Hz, 2H) 4.52–4.78 (m, 4H) 8.00 (s, 1H)

Example 11
Production of 9-[2-[bis(2,2,2-trifluoroethyl)phosphonylmethoxy]ethyl]-6-chloropurine (compound No. 1,084 in Table 1)

The procedure in Example 1 was repeated, except that 6-chloropurine was used instead of adenine, to obtain the title compound.

m.p.: oil
1H-NMR (CDCl$_3$, δ) 3.95 (d, J=7.8 Hz, 2H) 4.00 (t, J=4.9 Hz, 2H) 4.34–4.48 (m, 4H) 4.52 (t, J=4.9 Hz, 2H) 8.20 (s, 1H) 8.75 (s, 1H)

Example 12
Production of 9-[2-[methyl(2,2,2-trifluoloethyl) phosphonylmethoxy]ethyl]adenine (compound No. 303 in Table 1)

The compound obtained in Example 1 (1 g, 2.3 mmol) was dissolved in methanol (10 ml), to which was added silica gel (5 g). After reaction at 50° C. for 7 hours, the product was concentrated to dryness. The residue was eluted with 5% methanol/chloroform to obtain the title compound (0.75 g, 88%).

m.p.: 107–110° C. (ethyl acetate/hexane)

1H-NMR (CDCl3, δ): 3.74 (d, J=11.1 Hz, 3H) 3.83 (d, J=8.3 Hz, 2H) 3.93 (t, J=4.1 Hz, 2H) 4.30–4.39 (m, 4H) 5.65 (br, 2H) 7.86 (s, 1H) 8.33 (s. 1H)

Example 13
Production of 9-[2-[methyl(2,2,2-trifluoloethyl) phosphonylmethoxy]ethyl]-2,6-diaminopurine (compound No. 453 in Table 1)

The procedure in Example 9 was repeated, except that the compound obtained from Example 2 was used instead of that obtained from Example 1, to obtain the title compound.

m.p.: amorphous

1H-NMR (CDCl3, δ) : 3.77 (d, J=11.0 Hz, 3H) 3.86 (d, J=8.2 Hz, 2H) 3.91 (t, J=5.0 Hz, 2H) 4.24 (t, J=4.1 Hz, 2H) 4.25–4.42 (m, 2H) 4.69 (br, 2H) 5.35 (br, 2H) 7.6 0(s. 1H)

Example 14
Production of 9-[[2-[bis(2-methoxyethyl) phosphonylmethoxy]ethyl]adenine (compound No. 313 in Table 1)

9-[(2-Phosphonylmethoxy)ethyl]adenine (1 g, 3.5 mmol) was suspended in dichloromethane (10 ml) and reacted with trimethylsilyldiethylamine (3 ml) at room temperature for an hour and concentrated to dryness. The residue was dissolved in dichloromethane (10 ml), to which were added dimethylformamide (0.05 ml) and oxalyl chloride (0.9 ml). The mixture was reacted under ice-cooling for an hour, then at room temperature for an hour. After solvent was distilled off, the residue was dissolved in pyridine (20 ml) and reacted with 2-methoxyethanol (0.76 g) at room temperature for 12 hours. After concentration to dryness, the residue was dissolve in chloroform, adsorbed on silica gel column, eluted with 5% methanol/chloroform to give the title compound (0.3 g, 22%).

m.p.: 90–93° C. (ethyl acetate/hexane)

1H-NMR (CDCl3, δ) : 3.35 (s, 6H) 3.55 (d, J=4.6 Hz, 4H) 3.86 (d, J=8.2 Hz, 2H) 3.95 (t, J=4.9 Hz, 2H) 4.16–4.19 (m, 4H) 4.40 (t, J=4.9 Hz, 2H) 5.67 (br, 2H) 7.98 (s, 1H) 8.35 (s. 1H)

Example 15
Production of 9-[[2-bis(2-phenoxyethyl) phosphonylmethoxy]ethyl]adenine (compound No. 323 in Table 1)

The procedure in Example 11 was repeated, except that 2-phenoxyethanol was used instead of 2-methoxyethanol, to obtain the title compound.

m.p.: 112–115° C. (hexane)

1H-NMR (CDCl3, δ): 3.88 (t, J=4.8 Hz, 2H) 3.95 (d, J=8.0 Hz, 2H) 4.07 (t, J=4.4 Hz, 4H) 4.21–4.26 (m, 4H) 4.30 (t, J=4.8 Hz, 2H) 5.55 (br, 2H) 6.85–6.92 (m, 6H) 7.26 (t, J=7.4 Hz, 4H) 8.06 (s, 1H) 8.12 (s. 1H)

Example 16
Production of 9-[[2-bis(2-benzyloxyethyl) phosphonylmethoxy]ethyl]adenine (compound No. 331 in Table 1)

The procedure in Example 11 was repeated, except that 2-benzyloxyethanol was used instead of 2-methoxyethanol to obtain the title compound.

m.p.: 45–48° C. (hexane)

1H-NMR (CDCl3, δ) : 3.61 (d, J=4.6 Hz, 4H) 3.81 (d, J=8.1 Hz, 2H) 3.84 (t, J=5.0 Hz, 2H) 4.17–4.23 (m, 4H) 4.30 (t, J=5.0 Hz, 2H) 4.51 (s, 4H) 5.49 (br, 2H) 7.29–7.33 (m, 10H) 7.91 (s, 1H) 8.35 (s, 1H)

Example 17
Production of 9-[[2-bis(2-acetoxyethyl) phosphonylmethoxy]ethyl]adenine (compound No. 343 in Table 1)

The procedure in Example 11 was repeated, except that 2-acetoxyethanol was used instead of 2-methoxyethanol, to obtain the title compound.

m.p.: 68–70° C. (ethyl acetate/hexane)

1H-NMR (CDCl3, δ): 2.08 (s, 6H) 3.84 (d, J=8.3 Hz, 2H) 3.95 (t, J=4.9 Hz, 2H) 4.22–4.26 (m, 8H) 4.42 (t, J=4.9 Hz, 2H) 5.63 (br, 2H) 7.94 (s, 1H) 8.36 (s. 1H)

Example 18
Production of 9-[[2-bis(2-valeryloxyethyl) phosphonylmethoxy]ethyl]adenine (compound No. 349 in Table 1)

The procedure in Example 11 was repeated, except that 2-valeryloxyethanol was used instead of 2-methoxyethanol to obtain the title compound.

m.p.: oil

1H-NMR (CDCl3, δ): 0.91 (t, J=7.5 Hz, 6H) 1.36 (qt, J=7.5 Hz, 4H) 1.60 (tt, J=7.5 Hz, 4H) 2.33 (t, J=7.5 Hz, 4H) 3.83 (d, J=8.1 Hz, 2H) 3.95 (t, J=5.0 Hz, 2H) 4.21–4.25 (m, 8H) 4.41 (t, J=5.0 Hz, 2H) 5.73 (br, 2H) 7.94 (s, 1H) 8.35 (s. 1H)

Example 19
Production of 9-[2-bis(2,2,2 -trifluoroethyl) phosphonylmethoxy]ethyl]-2-iodoadenine (compound No. 359 in Table 1)

The procedure in Example 11 was repeated, except that 2,2,2-trifluoroethanol and 9-[(2-phosphonylmethoxy)ethyl]-2-iodoadenine were used instead of 2-methoxyethanol and 9-[(2-phosphonylmethoxy)ethyl]adenine, respectively, to obtain the title compound.

m.p.: 179° C. (CHCl$_3$)

1H-NMR (Me2SO-d6, δ): 3.88 (t, J=5.0 Hz, 2H) 4.13 (d, J=8.0 Hz, 2H) 4.28 (t, J=5.0 Hz, 2H) 4.56–4.70 (m, 4H) 7.63 (br, 2H) 7.99 (s, 1H)

Example 20
Production of 9-[2-bis(2,2,2-trifluoroethyl) phosphonylmethoxy]ethyl]guanine (compound No. 259 in Table 1)

The procedure in Example 1 was repeated, except that 6-O-benzylguanine, which can be synthesized by the known method, was used instead of adenine, to obtain 9-[2-[bis(2,2,2-trifluoroethyl)phosphonylmethoxy]ethyl]-6-O-benzylguanine.

The compound (2.21 g, 4.07 mmol) was dissolved in ethanol (20 ml), to which were added cyclohexene (20 ml) and 20% palladium hydroxide carbon (1.5 g), and the mixture was reacted under reflux for 2 hours. After palladium hydroxide carbon was removed by filtration, the solution was concentrated to dryness. The residue was dissolved in chloroform, adsorbed on a silica gel column and eluted with 5% methanol/chloroform to obtain the title compound (1.01 g, 55%).

m.p.: 214° C. (ethanol)

1H-NMR (Me2SO-d6, δ): 3.86 (t, J=5.1 Hz, 2H) 4.13 (d, J=8.1 Hz, 2H) 4.17 (t, J=5.0 Hz, 2H) 4.58–4.70 (m, 4H) 6.61 (br, 2H) 8.06 (s, 1H) 10.88 (br, 1H)

Example 21

Production of 7-[2-[bis(2,2,2-trifluoroethyl) phosphonylmethoxy]ethyl]guanine (compound No. 260 in Table 1)

Guanosine (1 g, 3.53 mmol) was suspended in dimethylacetaminde (10 ml), to which was added 2-[bis(2,2,2-trifluoroethyl)phosphonylmethoxy]ethyl iodide (1.7 g), and the reaction was carried out at 100° C. for 2 hours. The reaction solution was concentrated to dryness, and the residue was dissolved in 30% methanol/water, adsorbed on an octadecyl silica gel column, eluted with 30% methanol/water to give the title compound (0.1 g, 6.3%).

m.p.: 255° C.(H$_2$O)

1H-NMR (Me2SO-d6, δ) 3.89 (t, J=5.0 Hz, 2H) 4.10 (d, J=8.0 Hz, 2H) 4.40 (t, J=5.0 Hz, 2H) 4.57–4.70 (m, 4H) 6.34 (br, 2H) 8.09 (s, 1H) 10.95 (br, 1H)

Example 22

Production of 9-[2-bis(2,2,2-trifluoroethyl) phosphonylmethoxy]ethyl]adenine-1-N-oxide (compound No. 780 in Table 2)

The compound in Example 1 (8.12 g, 18.6 mmol) was dissolved in chloroform (150 ml), to which was added m-chloroperbenzoic acid (15 g), and reacted at 50° C. for 2 hours. The separated precipitate was removed by filtration, then adsorbed on a silica gel column and eluted with 5% methanol/chloroform to give the title compound (3.42 g, 42%).

m.p.: 186° C. (ethyl acetate)

1H-NMR (Me2SO-d6, δ) 3.88 (t, J=5.0 Hz, 2H) 4.10 (d, J=8.0 Hz, 2H) 4.36 (t, J=5.0 Hz, 2H) 4.52–4.66 (m, 4H) 8.18 (s, 1H) 8.56 (s, 1H)

Example 23

Production of 9-[2-[bis(2,2,2-trifluoroethyl) phosphonylmethoxy]ethyl]-6-thioguanine (compound No. 609 in Table 1)

The compound in Example 3 (800 mg, 1.7 mmol) was dissolved in ethanol (15 ml), to which was added thiourea (157 mg) and reacted under reflux for 4 hours. After reaction was over, the mixture was cooled to room temperature and concentrated to dryness. The residue was dissolved in chloroform, adsorbed on a silica gel column and eluted with 5% methanol/chloroform to give the title compound (252 mg, 32%).

m.p.: 144° C. (ethanol)

1H-NMR (Me2SO-d6, δ): 3.80 (t, J=5.1 Hz, 2H) 4.06–4.16 (m, 4H) 4.49–4.68 (m, 4H) 6.73 (br, 2H) 7.76 (s, 1H)

Example 24

Production of 9-[2-[bis(2,2,2-trifluoroethyl) phosphonylmethoxy]ethyl]-2-amino-6-p-toluylthiopurine (compound No. 1,030 in Table 6)

The compound in Example 3 (9.4 mg, 20 mmol) was dissolved in DMF (90 ml). p-Thiocresol (5.23 g) and triethylamine (2.8 ml) were added at room temperature, and the mixture was reacted at 100° C. for 4 hours. After reaction was over, the reaction mixture was cooled to room temperature and concentrated to dryness. The residue was dissolved in chloroform, adsorbed on a silica gel column and eluted with chloroform to give the title compound (9.8 g, 88%).

m.p.: oil

1H-NMR (CDCl3, δ): 2.40 (s, 3H) 3.89–3.96 (m, 4H) 4.26 (d, J=5.1 Hz, 2H) 4.39–4.47 (m, 4H) 4.79 (br, 2H) 7.23 (d, J=9.8 Hz, 2H) 7.31 (d, J=9.8 Hz, 2H) 7.71 (s, 1H)

Example 25

Production of 9-[2-[bis(2,2,2-trifluoroethyl) phosphonylmethoxy]ethyl]-2-hydroxy-6-p-toluylthiopurine (compound No. 1,055 in Table 7)

The compound in Example 21 (6.9 mg, 12.3 mmol) was dissolved in 50% aqueous acetic acid (120 ml). Sodium nitrite (12 g) was added thereto, and the mixture was reacted at 50° C. for 1 hour. After reaction was over, the reaction mixture was cooled to room temperature and concentrated to dryness. The residue was partitioned between chloroform and aqueous sodium bicarbonate, and the chloroform layer was dried on magnesium sulfate and filtered. The filtrate was concentrated to dryness, crystallized from ether to give the title compound (2.31 g, 34%).

m.p.: 176° C. (ether)

1H-NMR (Me2SO-d6, δ) :2.33 (s, 3H) 3.85 (t, J=5.1 Hz, 2H) 4.01 (d, J=8.0 Hz, 2H) 4.25 (d, J=5.1 Hz, 2H) 4.53–4.69 (m, 4H) 7.24 (d, J=8.1 Hz, 2H) 7.43 (d, J=8.1 Hz, 2H) 8.05 (s, 1H) 11.58 (br, 1H)

Example 26

Production of 9-[2-[bis(2,2,2-trifluoroethyl) phosphonylmethoxy]ethyl]-1-methylguanine (compound No. 1,005 in Table 5)

The compound in Example 20 (500 mg, 1.1 mmol) was dissolved in DMF (7 ml), and reacted with potassium carbonate (150 mg), molecular sieves (0.4 nm, 100 mg) and methyl iodide (203 mg) at room temperature for 2 hours. The reaction solution was filtered and concentrated to dryness. The residue was dissolved in chloroform, adsorbed on a silica gel column and eluted with 5% methanol/chloroform to give the title compound (30 mg, 5.8%).

m.p.: oil $^1$H-NMR (Me$_2$SO-d$_6$, δ): 3.27 (s, 3H) 3.80 (d, J=5.0 Hz, 2H) 4.05–4.11 (m, 4H) 4.52–4.68 (m, 4H) 6.98 (br, 2H) 7.59 (s, 1H)

Reference Example 1

Production of 9-[[2-bis(2-acetamidethyl) phosphonylmethoxy]ethyl]adenine

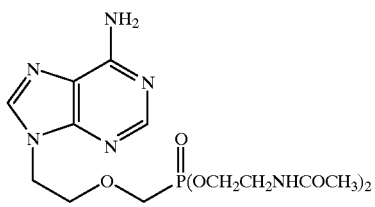

The procedure in Example 11 was repeated, except that 2-acetamide ethanol was used instead of 2-methoxyethanol, to obtain the title compound.

m.p.: oil

1H-NMR (CDCl3, δ): 2.02 (s, 6H) 3.41–3.53 (m, 4H) 3.81 (d, J=8.5 Hz, 2H) 3.94 (t, J=4.9 Hz, 2H) 3.97–4.21 (m, 4H) 4.43 (t, J=4.9 Hz, 2H) 6.18 (br, 2H) 6.77 (br, 2H) 8.00 (s, 1H) 8.34 (s. 1H)

Reference Example 2

Production of 9-[[2-bis(2-hydroxyethyl)phosphonylmethoxy]ethyl]adenine

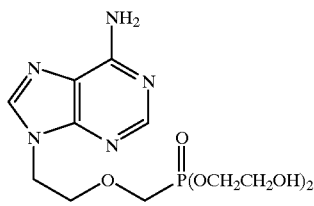

The compound obtained from Example 13 (1 g, 1.9 mmol) was dissolved in ethanol, 10% palladium-carbon (0.1 g) was added and reacted at 60° C. for 7 hours under hydrogen atmosphere. After palladium-carbon was removed by filtration, the solution was concentrated to dryness. The residue was dissolved in chloroform, adsorbed on a silica gel column, eluted with 5% methanol/chloroform to give the title compound (0.38 g, 55%).

m.p.: 102–104° C. (ethyl acetate)

1H-NMR (Me2SO-d6, δ) 3.50 (q, J=3.9 Hz, 4H) 3.86–3.96 (m, 8H) 4.32 (t, J=5.1 Hz, 2H) 4.85 (t, J=5.6 Hz, 2H) 7.21 (br, 2H) 8.09 (s, 1H) 8.13 (s. 1H)

Experiment 1

Inhibition of HBV growth

HB611 cells (recombinant human lever cancer cell producing HBV, $2 \times 10^4$) was incubated on Dulbecco ME medium containing bovine fetal serum, streptomycin (100 mg/ml), penicillin (100 IU/ml) and G-418 (0.2 mg/ml) at 37° C. On the 2nd and 5th days of cultivation, the medium was changed, then the media containing specimens at final concentration of 10 mM were substituted on the 8th, 11th and 14th days. On 17 days of cultivation, DNA of the cell was recovered. The amount of HBV-DNA was measured by southern blotting, and inhibition of HBV-DNA synthesis in the cell was determined. In addition, the concentration of the compound required for 50% death of the HB611 cells was determined. The results are shown in the following Table 8.

TABLE 8

| Compound | Inhibition of HBV-DNA Synthesis (%) | LD$_{50}$ of HB611 cell (µM) |
|---|---|---|
| Example 1 | 91.5 | >1000 |
| Example 2 | 99.9 | 840 |
| Example 3 | 99.9 | 399 |
| Example 5 | 97.2 | — |
| Example 12 | 86.3 | >1000 |
| Example 13 | 100 | >1000 |
| Example 14 | 55.0 | >1000 |
| Example 15 | 59.7 | 174 |
| Example 16 | 57.8 | 178 |
| Example 17 | 66.2 | >1000 |
| Example 18 | 73.4 | 47 |
| Example 20 | 99.9 | — |
| Example 21 | 71.3 | — |
| Example 22 | 76.2 | — |
| Example 23 | 86.1 | — |
| Example 24 | 99.9 | — |
| Example 25 | 99.9 | — |
| Example 26 | 99.9 | — |
| Reference Example 1 | — | >1000 |
| Reference Example 2 | 31.0 | >1000 |

Experiment 2

Inhibition of HBV growth in rat or mouse serum upon oral administration

Groups of rats (3 rats per group) were received single oral dose of specimen (1 g/kg or 0.5 g/kg), bled at 1 hour after administration and serum was prepared. Separately, groups of mice (3 mice per group) were received single oral dose of specimen (0.3 g/kg), bled at 30 minutes after administration and serum was prepared.

HB611 cells ($2 \times 10^4$) were incubated on Dulbecco ME medium containing 10% bovine fetal serum, streptomycin (100 mg/ml), penicillin (100 IU/ml) and G-418 (0.2 mg/ml) at 37° C. On the 2nd and 5th days of cultivation, the medium was changed, then substituted with a medium containing 5% of the above serum (rat or mouse serum after oral administration of the specimen) on the 8th, 11th and 14th day, and DNA of the cell was recovered on the 17th days of cultivation. The amount of HBV-DNA was measured by southern blotting, and intracellular HBV-DNA synthesis inhibition was determined. For reference, the same experiment was conducted on PMEA. The results are shown in the following Table 9.

TABLE 9

| Compound | Subject | Oral Dosage (g/kg) | HBV-DNA Synthesis Inhibition (%) |
|---|---|---|---|
| Example 1 | Rat | 1 | 89.9 |
| Example 2 | Rat | 1 | 71.9 |
| Example 3 | Mouse | 0.3 | 99.9 |
| Example 4 | Mouse | 0.3 | 36.3 |
| Example 5 | Mouse | 0.3 | 87.2 |
| Example 12 | Rat | 1 | 92.9 |
| Example 13 | Rat | 1 | 77.7 |
| Example 14 | Rat | 0.5 | 25.4 |
| Example 15 | Rat | 0.5 | 38.5 |
| Example 16 | Rat | 0.5 | 43.6 |
| Example 18 | Rat | 0.5 | 61.4 |
| Example 20 | Mouse | 0.3 | 99.9 |
| Example 22 | Mouse | 0.3 | 15.2 |
| Reference Example 1 | Rat | 0.5 | 0 |
| Reference Example 2 | Rat | 0.5 | 0 |
| PMEA | Rat | 1 | 35.5 |

What is claimed is:

1. A phosphonate-nucleotide ester compound of the following formula (I):

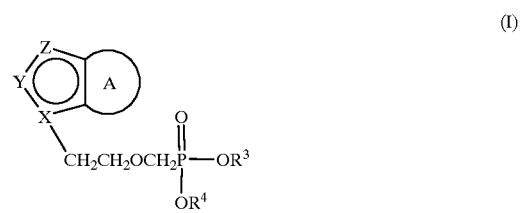

wherein ring A represents

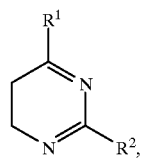

wherein $R^1$ represents halogen, hydroxyl, mercapto, tolylthio or amino; $R^2$ represents hydrogen or amino; $R^3$ represents ethyl having one or more fluorine substituents; $R^4$ represents ethyl having one or more fluorine substituents; X, Y and Z independently represent methyne or nitrogen atom; or a pharmaceutically acceptable salt thereof.

2. The compound according to claim 1, wherein $R^1$ is tolylthio.

3. The compound according to claim 1, wherein $R^2$ is amino.

4. The compound according to claim 1, wherein $R^3$ is 2,2,2-trifluoroethyl.

5. The compound according to claim 1, wherein $R^4$ is 2,2,2-trifluoroethyl.

6. The compound according to claim 1, wherein X and Z are nitrogen atoms, X and Y are nitrogen atoms, or X, Y and Z are nitrogen atoms.

7. A pharmaceutical composition which comprises a compound of claim 1 and a pharmaceutically acceptable carrier.

* * * * *